US009052324B2

(12) United States Patent
Liu et al.

(10) Patent No.: US 9,052,324 B2
(45) Date of Patent: *Jun. 9, 2015

(54) COMPOUNDS AND ASSAYS FOR CONTROLLING WNT ACTIVITY

(75) Inventors: Dakai Liu, South Setauket, NY (US); Xiaofeng Li, Farmington, CT (US); Richard Jin, Pennington, NJ (US); Yuaxin Liang, South Setauket, NY (US); Wei Cheng, Seaford, NY (US); Riddhi Bhattacharyya, West Babylon, NY (US); Guangrong Zhang, Shrewsbury, MA (US)

(73) Assignee: Enzo Biochem, Inc., New York, NY (US)

( * ) Notice: Subject to any disclaimer, the term of this patent is extended or adjusted under 35 U.S.C. 154(b) by 224 days.

This patent is subject to a terminal disclaimer.

(21) Appl. No.: 12/454,765

(22) Filed: May 22, 2009

(65) Prior Publication Data
US 2010/0298200 A1 Nov. 25, 2010
US 2012/0322717 A9 Dec. 20, 2012

Related U.S. Application Data

(63) Continuation-in-part of application No. 12/228,757, filed on Aug. 15, 2008, which is a continuation-in-part of application No. 12/221,863, filed on Aug. 7, 2008, which is a continuation-in-part of application No. 11/598,916, filed on Nov. 14, 2006, which is a continuation-in-part of application No. 11/097,518, filed on Apr. 1, 2005, which is a continuation-in-part of application No. 11/084,668, filed on Mar. 18, 2005, which is a continuation-in-part of application No. 10/849,067, filed on May 19, 2004.

(51) Int. Cl.
| A61K 31/538 | (2006.01) |
| G01N 33/68 | (2006.01) |
| C40B 30/02 | (2006.01) |
| C07D 265/28 | (2006.01) |
| C07D 265/38 | (2006.01) |
| C07D 265/34 | (2006.01) |
| A61K 31/536 | (2006.01) |

(52) U.S. Cl.
CPC .......... *G01N 33/6845* (2013.01); *A61K 31/538* (2013.01); *C07D 265/38* (2013.01); *C07D 265/28* (2013.01); *C07D 265/34* (2013.01); *A61K 31/536* (2013.01); *C40B 30/02* (2013.01); *G01N 2800/36* (2013.01)

(58) Field of Classification Search
CPC ............... C40B 30/02; G01N 2800/36; G01N 33/6845; A61K 31/538; A61K 31/536; C07D 265/28; C07D 265/38
See application file for complete search history.

(56) References Cited

U.S. PATENT DOCUMENTS

| 5,070,083 | A | 12/1991 | Barlet et al. |
| 5,340,825 | A | 8/1994 | Horwell et al. |
| 5,969,095 | A | 10/1999 | Dong et al. |
| 6,204,270 | B1 | 3/2001 | Ron et al. |
| 6,844,422 | B1 | 1/2005 | Niehrs et al. |
| 7,220,754 | B2 | 5/2007 | Dijkstra et al. |
| 8,461,155 | B2 * | 6/2013 | Wu et al. ............. 514/229.8 |
| 8,637,506 | B2 * | 1/2014 | Wu et al. ............. 514/229.8 |
| 2003/0138848 | A1 | 7/2003 | Moarefi et al. |
| 2003/0165500 | A1 | 9/2003 | Rhee |
| 2003/0181660 | A1 | 9/2003 | Todd et al. |
| 2004/0009535 | A1 | 1/2004 | Brunkow |
| 2004/0023356 | A1 | 2/2004 | Krumlauf et al. |
| 2004/0038860 | A1 | 2/2004 | Allen |
| 2004/0235728 | A1 | 11/2004 | Stoch |
| 2005/0043385 | A1 | 2/2005 | Guy |
| 2005/0084494 | A1 | 4/2005 | Prockop |
| 2005/0196349 | A1 | 9/2005 | Wu et al. |
| 2005/0244826 | A1 | 11/2005 | Niehrs et al. |
| 2005/0261181 | A1 | 11/2005 | Wu et al. |
| 2006/0030523 | A1 | 2/2006 | Wu et al. |
| 2006/0127393 | A1 | 6/2006 | Li et al. |
| 2006/0257892 | A1 | 11/2006 | Cohen et al. |
| 2007/0196872 | A1 | 8/2007 | Bex et al. |
| 2008/0119402 | A1 | 5/2008 | Zheng et al. |

(Continued)

FOREIGN PATENT DOCUMENTS

| WO | WO 02/076397 A2 * | 10/2002 |
| WO | WO02/092015 | 11/2002 |

(Continued)

OTHER PUBLICATIONS

Dostal et al. 1982, "Acid-base equilibriums of some 7-(dimethylamino)-3-phenoxazone derivatives." Collection of Czechoslovak Chemical Communications, vol. 47 (6), pp. 1588-1596.*
Rawadi et al. 2005, "Wnt signaling pathway: a new target for the treatment of osteoporosis." Expert Opinion Ther. Targets, vol. 9(5), pp. 1063-1077.*
Westendorf et al. 2004, "Wnt signaling in osteoblasts and bone diseases." Gene, vol. 341, pp. 19-39.*
Kroot et al. 2000, "Bone mass in rheumatoid arthritis." Clinical and Experimental Rheumatology, 18 Suppl. 21, pp. S12-S15.*
2001 NIH Consensus Conference Development Panel on Osteoporosis Prevention, Diagnosis and Therapy. JAMA 285:785-795.

(Continued)

Primary Examiner — Kara R McMillian
(74) Attorney, Agent, or Firm — Anna D. DiGabriele Petti

(57) ABSTRACT

The present invention relates to the field of therapeutic methods to screen for compounds on the basis of their ability to influence Wnt activity. The screening process is applied to both a physical library of a series of compounds and a virtual library of compounds that affect Wnt activity. In one aspect, the virtual screening process could be carried out where a permutational library of small peptides is substituted for the small organic molecules. The inventive methods may be used to empirically test for effects on Wnt activity and may also be applied to any pair of proteins involved in protein-protein interactions.

1 Claim, 48 Drawing Sheets

(56) References Cited

U.S. PATENT DOCUMENTS

2008/0318838 A1 12/2008 Bauer et al.
2010/0298308 A1 11/2010 Wu et al.
2011/0105606 A1 5/2011 Rabbani et al.

FOREIGN PATENT DOCUMENTS

WO WO03/106657 12/2003
WO WO2004/084949 10/2004

OTHER PUBLICATIONS

Axford, John S. Glycobiology & Medicine: A Millenial Review, Jul. 11-12, 2000 lecture at 5th Jenner Symposium held at Royal Society of Medicine, London, UK, http://www/glycoscience.com/glycoscience/document_viewer.wm?FILENAME=D006.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002, N Engl J Med 346(20):1513-21.
Capelluto et al. 2002, Nature 419(6908):726-9.
Cheyette et al. 2002, Dev Cell, vol. 2, 449-461.
Clark et al. 2002, J. Mol. Graph.
Culi et al. 2003, Cell 112:343-54.
Dale et al. 1998, 329:209-223.
Daniels et al 2002, 10(3):573-84.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.
Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.
Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lilien, Ryan H. et al., Mar. 4, 2004 Dartmouth Computer Science Dept. Technical Report No. TR2004-492 at http://www.cs.dartmouth.edu/reports/reports.html.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, 2001, Mol Cell 7:801-9.
Monaghan 1999, Mech Dev 87:45-56.
Moon RT et al, 1997, Cell, vol. 88, 725-728.
Nusse 2001, Nature 411:255-6.
Pandur et al, 2001, Bioessays 23;207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424;969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al., 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(S):1251-60.
Wong et al, 2000, Nat Struct Biol. 7(12):1178-84.
Xing Y et al, 2003, Genes Dev. Nov. 15, 2003;17(22):2753-64.
Wang et al., Am Chem Society, 2004.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116; 2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al, 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Logan et al, Annu. Rev. Cell Dev. Biol 20; 781-810.
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1;279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24: 263-280.
Tian et al. 2003 NEJM 349: 2483-2494.
Oshima et al., 2005 Blood 106: 3160-3165.
Toomes et al, 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Chilosi et al., 2003, Am J. Pathol. 162: 1495-1502.
Cheon et al., 2002 Proc. Nat, Acad. Sci. (USA) 99: 6973-6978.
Miyaoka et al., 1999 Schizophr. Res, 38:1-6.
Symolon et al. 2004 J. Nutr. 134: 1157-1161.
Chen H. et al. Cell 84: 491-495, 1996.
Lee G.H. Nature 379: 632-635, 1996.
Nusse and Varmus 1982, Cell 31:99-109.
Couso et al., 1995 Development 120: 621-636.
Mukhopadhyay et al., 2001 Dev Cell 1:423-434.
Li et al., 2005 Nature Genetics 37:945-952.

(56) References Cited

OTHER PUBLICATIONS

Mukhopadhyay et al., 2006 Development 133:2149-2154.
Pinson et al., 2000 Nature 407:535-538.
Magoori et al., 2003 J Biol Chem 278;11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381:667-673.
Abrami et al., 2003 J. Cell Biol 160:321-328.
Bradley et al., 2001, Nature 414 225-229.
Scobie et al., 2003 Proc Nat Acad Sci USA 100;5170-5174.
Molloy et al., 1992 J. Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol Chem. 277:3006-3010.
Rosovitz et al., 2003 J. Biol Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moaycri et al., 2006 Antimicrob Agents and Chemotherapy 50:2658-2665.
Schepetkin et al., 2006 J. Med. Chem. 49:5232-5244.
Goldman et al., 2006 BMC Pharmacology 6:8-15.
Panchal et al., 2004 Nat Struct Mol Biol 11:67-72.
Forino et al., 2005 Proc Nat Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.
Komiyama et al., 2005 Antimicrob Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.
Figueroa et al., 2000 J. Histochem & Cytochem, 48(10):1357-1368.
Sen et al., 2000 Proc Nat Acad Sci USA 2791-2796.
Nakamura et al., 2005 Am J Path 167:97-105.
Gustafson and Smith 2006 J. Biol Chem 281:9507-9516.
Cawthorn et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Andl et al., 2002 Developmental Cell 2:643-653.
Sick et al., 2006 Science 1447-1450.
Tamamura et al., 2005 J. Biol Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Swiatek et al., 2006 J Biol Chem 281:12233-12241.
Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000 Curr Biol 16:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells, *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-l and beta-catenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia, *Cell* 89, 773-9 (1997).
Otto, F. et al. Cbfa1, a candidate gene for cleidocranial dysplasia syndrome, is essential for osteoblast differentiation and bone development. *Cell* 89, 765-71 (1997).
Komori, T. et al. Targeted disruption of Cbfa1 results in a complete lack of bone formation owing to maturational arrest of osteoblasts. *Cell* 89, 755-64 (1997).
Ducy, P., Zhang, R., Geoffroy, V., Ridall, A. l. & Karsenty, G. Osf2/Cbfa1: a transcriptional activator of osteoblast differentiation. *Cell* 89, 747-54 (1997).
Pandur, P., Lasche, M., Eisenberg, I. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and *Xenopus* axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small non-peptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).
Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and The Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).
Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
DTP Datawarehouse Index Results, from http://dtp.nci.nih.gov/dtpstandard/servlet/dwindex?searchtype=NSC&outputformat=html&searchlist=366218 accessed Dec. 3, 2007.
In Vivo Models, http://dtp.nci.nih.gov/docs/invivo/invivomodels.html, accessed Dec. 3, 2007, p. 33 only of 55 provided.

(56) References Cited

OTHER PUBLICATIONS

NCI Communication re InVivo screening: email From: Daniel Zaharevitz[zaharevitz@dtpax2.ncicrf.gov], Sent: Tuesday, Dec. 4, 2007 5:37 PM, To: Garnett, Daniel C., Subject: Re: In vivo screen data, p. 1 of 1.
NCI In Vivo Screening Data http://dtp.nci.nih.gov/dtpstandard/servlet/InvivoScreen?testshortname=tumor+PS . . . Accessed Dec. 3, 2007.
U.S. Appl. No. 08/574,443, filed Dec. 15, 1995, Rabbani et al.
U.S. Appl. No. 09/356,294, filed Jul. 16, 1999, Rabbani et al.
C.I. Acid Blue 41-Compound Summary, obtained on Oct. 23, 2008 from http://pubchem.ncbi.nlm.nih.gov/summary/summary.cgi?cid-24200264&loc-ac__rcs.
Clark, Robert D., "Consensus Scoring for Ligand/Protein Interactions," *Journal of Molecular Graphics and Modeling*, vol. 20, pp. 281-296 (2002).
Dale, Trevor C., "Signal Tranduction by the Wnt Family of Ligands," *Biochem. J.*, vol. 329, pp. 209-223 (1998).
Daniels, Danette L., "ICAT inhibits beta-catenin binding to Tcl/Lef-family transcription factors . . . ," *Molecular Cell*, vol. 10, pp. 573-584 (2002).
Davidson, G., "Casein kinase 1 couples wnt receptor activation to cytoplasmic sugnal transduction," *Nature*, vol. 438, No. 8, pp. 867-872 (2005).
Day et al., "Wnt/β-Catenin Signaling in Mesenchymal Progenitors Controls Osteoblast and Chondrocyte Differentiation during Vertebrate Skeletogenesis," *Developmental Cell.*, vol. 8, pp. 739-750 (2005).
Delise et al., "Cellular interactions and signaling in cartilage development," *Osteoarthritis and Cartilage*, vol. 8, pp. 309-334 (2000).
Gregory, Carl, "The Wnt signaling inhibitor Dickkopf-1 is required for reentry into the cell cycle of human adult stem cells from bone marrow," *Journal of Biological Chemistry*, vol. 278, No. 30, pp. 28067-28078 (2003).
Grotewold et al., "Bmp, Fgf, and Wnt signaling in programmed cell death and chondrogenesis during vertebrate imb-development: the role of Dickopf-1," *Int. J. Dev. Biol.*, vol. 46, pp. 943-947 (2002).
Kelly, Olivia G., "The Wnt Co-Receptors LRP5 and LRP6 are Essential for Gastrulation in Mice," *Development*, vol. 131, pp. 2803-2815 (2004).
Kim et al., "Sox17 Dependence Distinguishes the Transcriptional Regulation of Fetal from Adult Hematopoietic Stem Cells," *Cell*, vol. 130, pp. 470-483 (2007).
Kitagaki et al., "Activation of beta-catenin-LEF/TCF signal pathway in chrondrocytes stimulates ectopic endochondral ossification," *Osteoarthritis and Cartilage*, vol. 11, pp. 36-43 (2003).
Logan et al., "The Wnt Signaling Pathway in Development and Disease," *Annu. Rev. Cell. Dev. Biol.*, vol. 20, pp. 781-810 (2004).
Mao, "LDL-receptor-related protein 6 is a receptor for Dickkopf proteins," *Nature*, vol. 411, pp. 321-325 (2001).
Mi et al., "Role of the Intracellular Domains of LRP5 and LRP6 in Activating the Wnt Canonical Paryway," *Journal of Cellular Biochemistry*, vol. 95, pp. 328-338 (2005).
Mi, K., "The low density lipoprotein receptor-related protein 6 Interacts . . . ," *The Journal of Biological Chemistry*, vol. 281, No. 8, pp. 4787-4794 (2006).
Otto et al., "Tomorrow's skeleton staff: mesenchymal stem cells and the repair of bone and cartilate," *Cell Prolif.*, vol. 37, pp. 97-110 (2004).
Papakonstantinou, E., "Matrix metalloproteinases of epithelial origin in facial seburn in patients with acne . . . ," *J. Invest. Dermatol.*, vol. 125, pp. 573-584 (2006).
Suredran, "A role for Wnt-4 in renal fibrosis," *Am. J. Physiol. Renal. Physiol.*, vol. 282, pp. F431-F441 (2002).
Wang, J., "Hierarchical database screening for HIV-1 reverse transcriptase using a phamacophone model . . . ," *J. Med. Chem.*, vol. 48, No. 7, pp. 2432-2444 (2005).
Zeng, X., "A Dual-Kinase Mechanism for Wnt Co-Receptor Phosphorylation and Activation," *Nature*, vol. 438, No. 8, pp. 873-877 (2005).

Abrami et al., Anthrax toxin triggers endocytosis of its receptor via a lipid raft-mediated clathrin-dependent process, J. Cell Biol., 2003, 321-328, 160.
Basha et al., Polyvalent inhibitors of anthrax toxin that target host receptors, PNAS, 2006, 13509-13513, 103(36).
Bockamp et al., Of mice and models: improved animal models for biomedical research, Physiol Genomics, 2002, 115-132, 11.
Bradley et al., Identification of the cellular receptor for anthrax toxin, Nature, 2001, 225-229, 414.
Chauhan et al., Identification of amino residues of anthrax protective antigen involved in binding with lethal factor, Infection and Immunity, 2002, 4477-4484, 70(8).
Couso et al., The wingless signaling pathway and the patterning of the wing margin in *Drosophila*, Development, 1994, 621-636, 120.
Cunningham et al., Mapping the lethal factor and edema factor binding sites on oligomeric anthrax protective antigen, PNAS, 2002, 7049-7053, 99(10).
Deng et al., Identification of major co-receptor for primary isolates of HIV-1, Nature, 1996, 661-666, 381.
Dragic et al., HIV-1 entry into CD4 cells is mediated by the chemokine receptor CC-CKR-5, Nature, 196, 667-673, 381.
Elliot et al., A quantitative study of the interactions of *Bacillus anthracis* edema factor and lethal factor with activated protective . . . , Biochemistry, 2000, 6706-6713, 39.
Forino et al., Efficient synthetic inhibitors of anthrax lethal factor, PNAS, 2005, 9499-9504, 102(27).
Fujino et al., Low-density lipoprotein receptor-related protein 5 (LPR5) is essential for normal cholesterol metabolism . . . PNAS, 2003, 229-234, 100(1).
Glinka et al., Dickkopf-1 is a member of a new family of secreted proteins and functions in head induction, Nature, 1998, 357-362, 391.
Goldman et al., Cationic polyamines inhibit anthrax lethal factor protease, BMC Pharmacology 2006, 1-8, 6(8).
Gong et al., LDL receptor-related protein 5 (LRP5) affects bone accrual and eye development, Cell, 2001, 513-523, 107.
Johnson et al., Defective splicing of Megf7/Lrp4, a regulator of distal limb development, in autosomal recessive mulefoot disease, Genomics, 2006, 600-609, 88.
Karginov et al., Blocking anthrax lethal toxin at the protective antigen channel by using structure-inspired drug design, PNAS, 2005, 15075-15080, 102(42).
Kato et al., Cbfa1-independent decrease in osteoblast proliferation, osteopenia, and persistent embryonic . . . Journal of Cell Biol, 2002, 303-314, 157(2).
Kelly et al., The Wnt co-receptors Lrp5 and Lrp6 are essential for gastrulation in mice, Development, 2004, 2803-2815, 131.
Kocer et al., Metalloproteinase inhibitors, nonantimicrobial chemically modified tetracyclines, and ilomastat . . . Infection and Immunity, 2005, 7548-7557, 73(11).
Komiyama et al., Protection from antrax toxin-mediated killing of macrophages by the combined effects . . . Antimicrobial Agents and Chemotherapy, 2005, 3875-3882, 49(9).
Lacy et al., Structure of heptameric protective antigen bound to an anthrax toxin receptor: a role for receptor in ph-dependent pore formation, PNAS, 2004, 13147-13151, 101(36).
Lacy et al., Mapping the anthrax protective antigen binding site on the lethal and edema factors, Journal of Biol. Chemistry, 2002, 3006-3010, 277(4).
Li et al, Dkk2 has a role in terminal osteoblast differentiation and mineralized matrix formation, Nature Genetics, 2005, 945-952, 37(9).
Little et al., Production and characterization of monoclonal antibodies to the protective antigen component of *Bacillus* . . . , Infection and Immunity, 1988, 1807-1813, 56(7).
Liu et al., Characterization of the interaction between anthrax toxin and its cellular receptors, Cell Microbiol, 2007, 977-987, 9(4).
Magoori et al., Severe hypercholesterolemia, impaired fat tolerance, and advanced atherosclerosis in mice lacking . . . Journal of Biol Chemistry, 2003, 11331-11336, 278(13).
Moayeri et al., Cisplatin inhibition of anthrax lethal toxin, Antimicrobial Agents and Chemotherapy, 2006, 2658-2665, 50(8).

(56) References Cited

OTHER PUBLICATIONS

Molloy et al., Human furin is a calcium-dependent serine endoprotease that recognizes the sequence arg-x-x-arg and . . . Journal of Biol. Chemistry, 1992, 16396-16402, 267(23).

Mukhopadhyay et al., Dickkopf1 is required for embryonic head induction and limb morphogenesis in the mouse, Developmental Cell., 2001, 423-434, 1.

Mukhopadhyay et al., Dkk2 play an essential role in the corneal fate of the ocular surface epithelium, Development, 2006, 2149-2154, 133.

Nusse et al., Many tumors induced by the mouse mammary tumor virus contain a provirus integrated in the same region of the host genome, Cell, 1982, 99-109, 31.

Opal et al., Inter-alpha-inhibitor proteins are endogenous furin inhibitors and provide protection against experimental . . . , Infection and Immunity, 2005, 5101-5105, 73(8).

Panchal et al., Identification of small molecule inhibitors of anthrax lethal factor, Nature Structural & Molecular Biology, 2004, 67-72, 11(1).

Pannifer et al., Crystal structure of the anthrax lethal factor, Nature, 2001, 229-233, 414.

Petosa et al., Crystal structure of the anthrax toxin protective antigen, Nature, 1997, 833-838, 385.

Pinson et al., An LDL-receptor-related protein mediates wnt signaling in mice, Nature, 2000, 535-538, 407.

Raport et al., Molecular cloning and functional characterization for a novel human cc chemokine receptor (CCR5) for . . . Journal of Biol Chemistry, 1996, 17161-17166, 271(29).

Rosovitz et al., Alanine-scanning mutations in domain 4 of anthrax toxin protective antigen reveal residues . . . Journal of Biol Chemistry, 2003, 30936-30944, 278(33).

Schepetkin et al., Novel small-molecule inhibitors of anthrax lethal factor identified by high-throughput screening, J. Med. Chem. 2006, 5232-5244, 49.

Scobie et al., Human capillary morphogenesis protein 2 functions as an anthrax toxin receptor, PNAS, 2003, 5170-5174, 100(9).

Turk et al., The structural basis for substrate and inhibitor selectivity of the anthrax lethal factor, Nature Structural & Molecular Biology, 2004, 60-66, 11(1).

Van Amerongen et al., Knockout mousse models to study Wnt signal transduction, Trends in Genetics, 2006, 678-689, 12.

Wei et al., The LDL receptor-related protein LRP6 mediates internalization and lethality of anthrax toxin, Cell, 2006, 1141-1154, 124.

Ai et al., "Reduced Affinity to and Inhibition by DKK1 Form a Common Mechanism by Which High Bone Mass-Associated Missense Mutations in LRP5 Affect Canonical Wnt Signaling," *molecular and Cellular Biology*, vol. 25, No. 12, pp. 4946-4955 (2005).

Bafico et al., "Interaction of Frizzled Related Protein (FRP) with Wnt Ligands and the Frizzled Receptor Suggests Alternative Mechanisms for FRP Inhibition of Wnt Signaling," *The Journal of Biological Chemistry*, vol. 274, No. 23, pp. 16180-16187 (1999).

Behrens et al., "Functional Interaction of B-catenin with the transcription factor LEF-1," *Nature*, vol. 382, pp. 638-642 (1996).

Berger et al., "Isolation of a candidate gene for Norrie disease by positional cloning," *nature genetics*, vol. 1, pp. 199-203 (1992).

Berry et al., "5-Nitrofuran-2-ylmethyl group as a potential bioreductively activated pro-drug system," *J. Chem. Soc.*, Perkin Trans. 1, pp. 1147-1156 (1997).

Binnerts et al., "R-Spondin1 regulates Wnt signaling by inhibiting internalization of LRP6" *PNAS*, vol. 104, No. 37, pp. 14700-14705 (2007).

Boucher et al., "LRP and PDGF Signaling: A Pathway to Atherosclerosis," *TCM*, vol. 14, No. 2, pp. 55-60 (2004).

Brown et al., "Isolation and Characterization of LRP6, a Novel Member of the low Density Lipoprotein Receptor Gene Family," *biochemical and Biophysical Research Communications*, Vo. 248, pp. 879-888 (1998).

Cam et al., "Modulation of B-amyloid precursor protein trafficking and processing by the low density lipoprotein receptor family," *Molecular Neurodegeneration*, vol. 1, No. 8, 13 pages (2006).

Caraci et al., "The Wnt Antagonist, Dickkopf-1, as a Target for the Treatment of Neurodegenerative Disorders," *Neurochem Res*, vol. 33, pp. 2401-2406 (2008).

Carcasole et al., "Induction of Dickkopf-1, a Negative Modulator of the Wnt Pathway, Is Associated with Neuronal Degeneration in Alzheimer's Brain," *Neurobiology of Disease*, vol. 24, No. 26, pp. 6021-6027 (2004).

Caricasole et al., "The Wnt pathway, cell-cycle activation and B-amyloid: novel therapeutic strategies in Alzheimer's disease?," *Trends in Pharmacological Sciences*, vol. 24, No. 5, pp. 233-238 (2003).

Chen et al., "Isolation and characterization of a candidate gene for Norrie disease," *nature genetics*, vol. 1, pp. 204-208 (1992).

Chen et al., "Mechanisms of Signal Transduction: Structural Insight into the Mechanisms of Wnt Signaling Antagonism by Dkk," *The Journal of the Biological Chemistry*, vol. 283, No. 34, pp. 23364-23370 (2008).

Chong et al., "Vascular Injury During Elevated Glucose Can Be Mitigated by Erythropoietin and Wnt Signaling," *Curr Neurovasc Res.*, vol. 4, No. 3, pp. 194-204 (2007).

DasGupta et al., "Multiple roles for activated LEF/TCF transcription complexes during hair follicle development and differentiation," *Development*, vol. 126, pp. 4557-4568 (1999).

Eastman et al., "Regulation of LEF-1/TCF transcription factors by Wnt and other signals," *Cell Biology*, vol. 11, pp. 233-240 (1999).

Eugenin et al., "HIV-tat induces formation of an LRP-PSD-95-NMDAR-nNOS complex that promotes apoptosis in neurons and astrocytes," *PNAS*, vol. 104, No. 9, pp. 3438-3443 (2007).

Finch et al., "Purification and molecular cloning of a secreted, Frizzled-related antagonist of Wnt action," *Proc. Natl. Acad. Sci.*, vol. 94, pp. 6770-6775 (1997).

Gaultier et al., "Regulation of tumor necrosis factor receptor-1 and the IKK-NF-kB pathway by LDL receptor-related protein explains the anti-inflammatory activity of this receptor," *Blood*, vol. 111, No. 11, pp. 5316-5325 (2008).

Gruenberg et al., "A Functional Screen in Human Cells Identifies UBF2 as an RNA Polymerase II Transcription Factor That Enhances the B-Catenin Signaling Pathway," *Molecular and Cellular Biology*, vol. 23, No. 11, pp. 3936-3950 (2003).

Guo et al., "Polymorphisms of the low-density lipoprotein receptor-related protein 5 (LRP5) gene are associated with obesity phenotypes in a large family-based association study," *J. Med Genet*, vol. 43, pp. 798-803 (2006).

Hammond et al., "B Strand Peptidomimetics as Potent PDZ Domain Ligands," *Chemistry & Biology*, vol. 13, pp. 1247-1251 (2006).

Hsieh et al., "A new secreted protein that binds to Wnt proteins and inhibits their activities," *Nature*, vol. 398, pp. 431-436 (1999).

Hu, "Prodrugs: Effective Solutions for Solubility, Permeability and Targeting Challenges;" *IDrugs*, vol. 7, No. 8, pp. 736-742 (2004).

Huber et al., "Nuclear localization of B-catenin by interaction with transcription factor LEF-1," *Mechanisms of Development*, vol. 59, pp. 3-10 (1996).

Inestrosa et al., "The role of Wnt signaling in neuronal dysfunction in Alzheimer's Disease," *Molecular Neurodegeneration*, vol. 3, No. 9, 13 pages (2008).

Itasaki et al., "Wise, a context-dependent activator and inhibitor of Wnt signaling," *Development*, vol. 130, pp. 4295-4305 (2003).

Jaeger et al., "Functional Role of Lipoprotein Receptors in Alzheimer's Disease," *Current Alzheimer Research*, vol. 5, pp. 15-25 (2008).

Jin et al., "The Wnt Signaling Pathway Effector TCF7L2 and Type 2 Diabetes Mellitus," *Molecular Endocrinology*, vol. 22, No. 11, pp. 2383-2292 (2008).

Johnson et al., "Diseases in Wnt signaling," *Rev Endocr Metab Disord*, vol. 7, pp. 41-49 (2006).

Juillerat-Jeanneret, Lucienne, The targeted delivery of cancer drugs across the blood-brain barrier: chemical modifications of drugs or drug-nanoparticles?, *Drug Discovery Today*, vol. 13, No. 23/24, pp. 1099-1106 (2008).

Kazanskays et al., "R-Spondin2 is a Secreted Activator of Wnt/B-Catenin Signaling and is Required of *Xenopus* Myogenesis," *Developmental Cell*, vol. 7, 525-534 (2004).

(56) References Cited

OTHER PUBLICATIONS

Kim et al., "R-Spondin Proteins: A Novel Link to etbeta;-catenin Activation," *Cell Cycle*, vol. 5, No. 1, pp. 23-26 (2006).

Kim et al., "R-Spondin Family Members Regulate the Wnt pathway by a Common Mechanism," *Molecular biology of the Cell*, vol. 19, pp. 2588-2596 (2008).

Kim et al., "New Evidence that Nuclear Import of endogenous B-Catenin is LEF-1 Dependent, While LEF-1 Independent Import of Exogenous B-Catenin Leads to Nuclear Abnormalities" *Cell Biology International*, vol. 25, No. 11, pp. 1149-1161 (2001).

Korinek et al, "Constitutive Transcriptional Activation by a B-Catenin-Tcf Complex in APC-/- Colon Carcinoma," *Science*, vol. 275, pp. 1784-1787 (1997).

Kumar et al., "Active B-Catenin Signaling is an Inhibitory Pathway for Human Immunodeficiency Virus Replication in Peripheral Blood Mononuclear Cells," *Journal of Virology*, vol. 82, No. 6, pp. 2813-2820 (2008).

Lehman et al., "Duplication of Seven Exons in LDL Receptor Gene Caused by Alu-Alu Recombination in a Subject with Familial Hypercholesterolemia," *Cell*, vol. 48, pp. 827-835 (1987).

Li et al., "Sclerostin Binds to LRP5/6 and Anatagonizes Canonical Wnt Signaling*," *The Journal of Biological Chemistry*, vol. 280, No. 20, pp. 19883-19887 (2005).

Li et al., "LRP6 expression promotes cancer cell proliferation and tumorigenesis by altering B-catenin subcellular distribution," *Oncogene*, vol. 23, pp. 9129-9135 (2004).

Lin et al., "Wnt/B-Catenin Signaling Modulates Survival of High Glucose-Stressed Mesagial Cells," *Am Soc Nephrol*, vol. 17, pp. 2812-2820 (2006).

Liu et al., "Augmented Wnt Signaling in a Mammalian Model of Accelerated Aging," *Science*, vol. 317, pp. 803-806 (2007).

Gossen et al., "Tight control of gene expression in mammalian cells by tetracycline-responsive promoters," *Proc. Natl. Acad. Sci.*, vol. 89, pp. 5547-5551 (1992).

Gossen et al., "Transcriptional Activation by Tetracyclines in Mammalian Cells," *Science*, vol. 268, No. 5218, pp. 1766-1769 (1995).

Lips, Paul, "Epidemiology and Predictors of Fractures Associated with Osteoporosis," *Am J. Med.*, vol. 103, No. 2A, pp. 3S-11S (1997).

Llorente-Cortes et al., "LDL Receptor-Related Protein and the Vascular Wall Implications for Atherothrombosis," *Arterioscler Thromb Vasc Biol.*, vol. 25, pp. 497-504 (2005).

Luo et al., "Wnt signaling and human diseases: what are the therapeutic implications?," *Laboratory Investigation*, vol. 87, 97-103 (2007).

Maiese et al., "The Wnt signaling pathway: Aging gracefully as a protectionist?," *ScienceDirect*, vol. 18, pp. 58-81 (2009).

Mani et al., "LRP6 Mutation in a Family with Early Coronary Disease and Metabolic Risk Factors," *Science*, vol. 315, pp. 1278-1282 (2007).

Manolagas et al., "Gone with the Wnts: B-Catenin, T-Cell Factor, Forkhead Box O, and Oxidative Stress in Age-Dependent Diseases of Bone, Lipid, and Glucose Metabolism," *Molecular Endocrinology*, vol. 21, No. 11, pp. 2605-2614 (2007).

Mermelstein et al., "Wnt/B-catenin pathway activation and myogenic differentiation are induced by cholesterol depletion," *Differentiation*, vol. 75, pp. 184-192 (2007).

Peters et al., "Casein kinase I transduces Wnt signals," *Nature*, vol. 401, pp. 345-350 (1999).

Piccolo et al, "The head inducer Cerberus is a multifunctional antagonist of Nodal, BMP and Wnt signals," *Nature*, vol. 397, pp. 707-710 (1999).

Portilho et al., "A soluble and active form of Wnt-3a protein is involved in myogenic differentiation after cholesterol depletion," *FEBS Letters*, vol. 581, pp. 5787-5795 (2007).

Rautio et al., "Prodrugs: design and clinical applications," *Nature*, vol. 7, pp. 255-270 (2008).

Rubin et al., "Secreted WNT agonists as tumor suppressors: pro and con," *Frontiers in Bioscience*, vol. 11, pp. 2093-2105 (2006).

Ryu et al., "Opposing Roles of WNT-5A and WNT-11 in Interleukin-1 B Regulation of Type II Collagen Expression in Articular Chondrocytes," *J. Biol. Chem.*, vol. 281, pp. 22039-22047 (2006).

Sakanaka et al., "Casein kinase 1e in the Wnt pathway: Regulation of B-catenin function," *PNAS*, vol. 96, No. 22, pp. 12548-12552 (1999).

Schlange et al., "Autocrine WNT signaling contributes to breast cancer cell proliferation via the canonical WNT pathway and EGFR transactivation," *Breast Cancer Research*, vol. 9, 15 pages (2007).

Semenov et al., "DKK1 Antagonizes Wnt Signaling without Promotion of LRP6 Internalization and Degradation,", *J. Biol. Chem.*, vol. 283, pp. 21427-21432 (2008).

Smallwood et al., "Mutational Analysis of Norrin-Frizzled4 Recognition," *J. Biol. Chem.*, vol. 282, No. 4057-4068 (2007).

Sprinter et al., "An Extracellular B-Proeller Module Predicted in Lipoprotein and Scavenger Receptors, Tyrosine Kinases, Epidermal Growth Factor Precursor, and Extracellular Matrix Components," *J. Mol. Biol.*, vol. 283, pp. 837-862 (1998).

Streeten et al., "Quantitative Trait Loci for BMD Identified by Autosome-Wide Linkage Scan to chromosomes 7q and 21q in Men from the Amish Family Osteoporosis Study," *Journal of Bone and Mineral Research*, vol. 21, No. 9, pp. 1433-1442 (2006).

Stella et al., "Prodrug strategies to overcome poor water solubility," *ScienceDirect, Advanced Drug Delivery Reviews*, vol. 59, pp. 677-694 (2007).

Strickland et al., "Diverse roles for the LDL receptor family," *Trends in Endocrinology & Metabolism*, vol. 13, No. 2, pp. 66-74 (2002).

Swiatek et al., "Regulation of Casein Kinase 1e Activity by Wnt Signaling," *The Journal of Biological Chemistry*, vol. 279, No. 13, pp. 13011-1017 (2004).

Tamaki et al., "Insulin Facilitates the Hepatic Clearance of Plasma Amyloid B-Peptide (1-40) by Intracellular Translocation of Low-Density Lipoprotein Receptor-Related Protein 1 (LRP-1) to the Plasma Membrane in Hepatocytes," *Molecular Pharacology*, vol. 72, No. 4, pp. 850-855 (2007).

Terrand et al., "LRP1 Controls Intracellular Cholesterol Storage and Fatty Acid Synthesis through Modulation of Wnt Signaling," *J. Biol. Chem.*, vol. 284, pp. 381-388 (2009).

Uren et al., "Secreted Frizzled-related Protein-1 Binds Directly to Wingless and is a Biphasic Modulator of Wnt Signaling," *J. Biol. Chem.*, vol. 275, pp. 4374-4382 (2000).

Wan et al., "Parathyroid hormone signaling through low-density lipoprotein-related protein 6," *Genes & Development*, vol. 22, pp. 2968-2979 (2008).

Wang et al., "characterization of the Kremen-binding Site on Kkk1 and Elucidation of the Role of Kremer in Dkk-mediated Wnt Antagonism," *J. Biol. Chem.*, vol. 283, 23371-23375 (2008).

Wang et al., "Frzb, a Secreted Protein expressed in the Spemann Organizer, Binds and Inhibits Wnt-8," *Cell*, vol. 88, pp. 757-766 (1997).

Wehrli et al., "arrow encodes an LDL-receptor-related protein essential for Wingless signaling," *Nature*, vol. 407, pp. 527-530 (2000).

Wei et al., "R-spondin1 is a High Affinity Ligand for LRP6 and Induces LRP6 Phosphorylation and B-Catenin Signaling," *J. Biol. Chem.*, vol. 282, pp. 15903-15911 (2007).

Wild et al., "Global Prevalence of Diabetes," *Diabetes Care*, vol. 27, No. 5, pp. 1047-1053 (2004).

Wright et al., "Wnt10b Inhibits Obesity in ob/ob and Agouti Mice," *Diabetes*, vol. 56, pp. 295-303 (2007).

Xu et al., "Vascular Development in the Retina and Inner Ear: control by Norrin and Frizzled-4, a High-Affinity Ligand-Receptor pair," *Cell*, vol. 116, pp. 883-805 (2004).

Yang et al., "Tyrosine Phosphorylation of the LDL receptor-related protein (LRP) and activation of the ERK pathway are required for connective tissue growth factor to potentiate Myofibroblast differentiation," *The FASEB Journal*, vol. 18, 20 pages (2004).

Zhang et al., "Small-molecule synergist of the Wnt/B-catenin signaling pathway," *PNAS*, vol. 104, No. 18, pp. 7444-7448 (2007).

Zurhove et al., "γ-Secretase Limits the Inflammatory Response Through the Processing of LRP1," *Science Signaling*, vol. 1, Issue 47, 12 pages (2008).

Miyauchi et al., *Histochem Cell bio*, vol. 116, pp. 57-62 (2001).

Verma et al., *Nature*, vol. 389, pp. 239-242 (1997).

(56) References Cited

OTHER PUBLICATIONS

Wei et al., "The LDL Receptor-Related Protein LPR6 Mediates Internalization and Lethality of Anthrax Toxin," *Cell*, vol. 124, pp. 1141-1154 (2006).
Dostal et al., "Acid-Base Equilibria of Some 7-Dimethylamino-3-Phenoxazone Derivatives," *Collection Czechoslavak Chem. Commun.*, vol. 47, pp. 1588-1596 (1982).
Barker and Clevers 2006, Nature Reviews: Drug Discovery, vol. 5, pp. 997-1014.
NSC668036—Substance summary, http://pubchem.ncbi.nim.nih.gov/summary/summary.cgi?sid-512577&loc-nc_rcs; viewed Oct. 30, 2008).
Reya and Clevers 2005, Nature, vol. 434, pp. 843-850.
Suzuki et al., 2004, Nature Genetics, vol. 36, pp. 417-422.
Wong et al., Mol. Cell Nov. 2003 vol. 12, No. 5, pp. 1251-1260.

* cited by examiner

M117-M136

| | | | |
|---|---|---|---|
| M117 n= 0 | m122 n= 5 | M127 n= 10 | M132 n= 15 |
| M118 n= 1 | M123 n= 6 | M128 n= 11 | M133 n= 16 |
| M119 n= 2 | M124 n= 7 | M129 n= 12 | M134 n= 17 |
| M120 n= 3 | M125 n= 8 | M130 n= 13 | M135 n= 18 |
| M121 n= 4 | M126 n= 9 | M131 n= 14 | M136 n= 19 |

M137-M156

| | | | |
|---|---|---|---|
| M137 n= 0 | m142 n= 5 | M147 n= 10 | M152 n= 15 |
| M138 n= 1 | M143 n= 6 | M148 n= 11 | M153 n= 16 |
| M139 n= 2 | M144 n= 7 | M149 n= 12 | M154 n= 17 |
| M140 n= 3 | M145 n= 8 | M150 n= 13 | M155 n= 18 |
| M141 n= 4 | M146 n= 9 | M151 n= 14 | M156 n= 19 |

M157-M175

| | | | |
|---|---|---|---|
| M157 n= 1 | m162 n= 6 | M167 n= 11 | M172 n= 16 |
| M158 n= 2 | M163 n= 7 | M168 n= 12 | M173 n= 17 |
| M159 n= 3 | M164 n= 8 | M169 n= 13 | M174 n= 18 |
| M160 n= 4 | M165 n= 9 | M170 n= 14 | M175 n= 19 |
| M161 n= 5 | M166 n= 10 | M171 n= 15 | |

M176-M193

| | | | |
|---|---|---|---|
| M176 n= 2 | m181 n= 7 | M186 n= 12 | M191 n= 17 |
| M177 n= 3 | M182 n= 8 | M187 n= 13 | M192 n= 18 |
| M178 n= 4 | M183 n= 9 | M188 n= 14 | M193 n= 19 |
| M179 n= 5 | M184 n= 10 | M189 n= 15 | |
| M180 n= 6 | M185 n= 11 | M190 n= 16 | |

M194-M210

| | | | |
|---|---|---|---|
| M194 n= 3 | M199 n= 8 | M204 n= 13 | M209 n= 18 |
| M195 n= 4 | M200 n= 9 | M205 n= 14 | M210 n= 19 |
| M196 n= 5 | M201 n= 10 | M206 n= 15 | |
| M197 n= 6 | M202 n= 11 | M207 n= 16 | |
| M198 n= 7 | M203 n= 12 | M208 n= 17 | |

M211-M226

| | | | |
|---|---|---|---|
| M211 n= 4 | M216 n= 9 | M221 n= 14 | M226 n= 19 |
| M212 n= 5 | M217 n= 10 | M222 n= 15 | |
| M213 n= 6 | M218 n= 11 | M223 n= 16 | |
| M214 n= 7 | M219 n= 12 | M224 n= 17 | |
| M215 n= 8 | M220 n= 13 | M225 n= 18 | |

M376

M377

M378

M379

M380

M381

M382

M383

M384

A) i.p. Administration

B) Administration by gavage

Effects of GCA compounds on mice on high caloric diet

A) Blood glucose levels

B) Glucose tolerance

C) Insulin tolerance

Effects of GCA compounds on db/db mice

HPLC Profile of GCA Preparation

GCA-Pool, GCA-F3 and GCA-F4

GCA-F1 and GCA-F2

Gallocyanine prototype

GCA-F3

GCA-F4

Core Structure X

Core Structure I

Core Structure IX

Analogues based on Gallocyanine

Synthesis of M228 and M230

Synthesis of M251, M333, M335, M338 and M339

M228 and M230

M251, M333 and M335

M338 and M339

Synthesis of M365 and M358

HPLC Profiles of M358 and M361

M358-Pool and M358-F1

M358-F2 and M358-F3

Synthesis of M361DT

Synthesis of M361T

Synthesis of M376DT, M361DT, M376T and M361T

M361DT-Pool, M361DT-F0 and M361DT-F1

M361DT-F2 and M361DT-F3

M361T-Pool, M361T-F0 and M361T-F1

Synthesis of M380

Synthesis of M381

Synthesis of M380 and M381

M380, M381-F1 and M381-F2

Selected "enzo" series compounds enzo530 enzo531 enzo540 enzo551 enzo552 enzo562 enzo522 enzo560 enzo558

Selected "enzo" series compounds enzo172, 173 and 174 enzo188, 191 and 192 enzo195, 197 and 198 enzo201, 517 and 525 enzo527, 530 and 531 enzo539, 540 and 551 enzo552 and 562 enzo522, 558 and 560

Synthesis of biotinylated gallocyanine

Variations on attachment site of Compound 5 products

AlkPhos activity after binding of LRP to immobilized gallocyanine

Effects of R-Spondin on Wnt activity and Sclerostin suppression

Sclerostin Binding Assay

COMPOUNDS AND ASSAYS FOR CONTROLLING WNT ACTIVITY

CROSS-REFERENCE TO RELATED U.S. APPLICATIONS

This application is a Continuation-in-Part of U.S. patent application Ser. No. 12/228,757, filed Aug. 15, 2008, which is a Continuation-in-Part of U.S. patent application Ser. No. 12/221,863 filed Aug. 7, 2008, which is a Continuation-in-Part of U.S. patent application Ser. No. 11/598,916 filed Nov. 14, 2006, which is a Continuation-in-Part of U.S. patent application Ser. No. 11/097,518 filed Apr. 1, 2005, which is a Continuation-in-Part of U.S. patent application Ser. No. 11/084,668 filed Mar. 18, 2005, which is Continuation-in-Part of U.S. patent application Ser. No. 10/849,067, filed May 19, 2004, the contents of all of which are incorporated herein by reference.

FIELD OF THE INVENTION

The present invention relates to the field of therapeutic methods, compositions and uses thereof, for modulating pathophysiological processes including but not limited to glucose metabolism, lipid metabolism, triglyceride metabolism, adipogenesis, initiation and growth of tumors, neurological diseases, viral infections and bone-related activity such as treatment of bone fractures, bone disease, bone injury, and bone abnormalities.

BACKGROUND OF THE INVENTION

Although the Wnt signal pathway was first determined in terms of developmental pathways during embryogenesis, further research has established that it continues to be a factor in adults as well. Consequently, increased or decreased levels of activity of various members of the Wnt pathway have been associated with a number of different disease conditions. For reviews on the relationship between the Wnt pathway and disease see Moon et al., 2004 Nature Rev. Genet. 5; 691-701, Manolagas and Almeida, 2005 Molec. Endrocrin. 21; 2605-2614, Johnson and Rajamannan, 2006 Rev. Endocr. Metab. Disord. 7; 41-49, Luo et al., 2007 Lab. Invest. 87; 97-103, Maiese et al., 2008 Pharmacology & Therapeutics 118; 58-81. As discussed in these reviews, diseases that have been associated with Wnt pathway elements include cancer, diabetes, osteoporosis, neurodegenerative diseases such as Alzheimers as well as vascular disease and cardiac dysfunction. Although these diseases are very disparate in terms of the nature of their pathologies, they are united in having one or more members of the Wnt signal pathway involved in the disease. The role of the Wnt signaling system is best known for its significance in cancer. However, there are other diseases involving Wnt that are of tremendous importance to healthcare. For example, diabetes is a disease whose prevalence is experiencing tremendous growth worldwide. While an increased life span may account for part of this growth, other factors such as diet, lifestyle and environment also likely play significant roles. Regardless of the causative agents, it was estimated that there were 16 million affected individuals in the United States alone and 171 million cases of diabetes worldwide in 2000; in addition there was an expectation that the latter number would rise to 366 million people in 2030 (Wild et al., 2000 Diabetes Care 27; 1047-1053).

One of the members of the Wnt signaling system, low density lipoprotein receptor-related protein 5 (LRP5), was initially isolated and characterized (Hey et al., 1998 Gene 216; 103-111) due to its proximity to IDDM4, a putative marker for diabetes. Expression patterns of LRP5 in macrophages, Vitamin A system cells and Islets of Langerhorns reinforced the idea of connectivity between LRP5 and diabetes (Figueroa 2000 J. Histochem. Cytochem. 48; 1357-1368). When low density lipoprotein receptor-related protein 6 (LRP6) was identified soon after, it was postulated that due the similarity with LRP5, it might also be involved in diabetes (Brown et al., 1998 Biochem. Biophys. Res. Commun. 248; 879-888). It was only later that LRP5 and LRP6 were recognized as being involved in the Wnt signaling system (Tamai et al., 2004 Nature 407; 530-535, Pinson et al., 2004 Nature 407; 535-538). Subsequently, Fujino et al. (2003 Proc. Nat. Acad. Sci. (USA) 100; 229-234) investigated the metabolic consequences of a genetic ablation of LRP5 and concluded that LRP5 is essential for both normal cholesterol metabolism and glucose-induced insulin secretion. The presence of an LRP5 deficiency in either homozygous (LRP5−/−) or even heterozygous (LRP5+/−) mice resulted in a significant increase in plasma cholesterol levels when the animals were fed a high-fat diet. Although fasted blood glucose and insulin levels were normal in the mutant strains, they showed a defect in glucose tolerance when challenged. These animals also showed impaired clearance of chylomicron remnants and also impaired glucose-induced insulin secretion from the pancreatic islets. The effect of a lack of LRP5 was also tested in a double mutation situation where the mice lacked not only LRP5, but also apoE (Magoori et al. 2003). Although neither condition alone led to changes in cholesterol levels with a normal diet, the double condition led to 60% higher plasma cholesterol levels. At 6 months of age, the double-null mice had also developed severe atherosclerotic lesions that were three times larger than those in knockout mice missing only apoE. The connection between LRP molecules and metabolism is also evidenced by the discovery that certain polymorphisms in the LRP5 gene have been correlated with obesity phenotypes in a family based study (Guo et al., 2006 J. Med. Genet. 43; 798-803) and intronic variants of LRP5 have been associated with obesity. Lastly, a mutation in LRP6 has been correlated to an autosomal dominant defect that results in the expression of phenotypic features associated with metabolic syndrome: hyperlipidemia, hypertension and diabetes (Mani et al., 2007 Science 315; 1278-1282. Other members of the Wnt signaling system such as TC7FL2 (also known as TCF-4) have also been associated with a risk for the development of diabetes (Jin and Liu 2008 Molec. Endocrin. 22; 2383-2392).

Reflecting its role in bone development during embryogenesis, the Wnt pathway continues to be involved in osteogenic processes such as healing of bone as well as bone degeneration diseases such as osteoporosis. Osteoporosis is a major public health problem, and it is especially prevalent in aging populations (NIH Consensus Conference Development Panel on Osteoporosis Prevention 2001 JAMA 285; 785-795, Kannus et al., 2000 Osteoporos. Int. 11; 443-448, Lips 1997 μm. J. Chem. Med. 103; 35-85). The majority of fractures that occur in people over the age of 65 are due to osteoporosis (Kannus 2000, Zuckerman 1996 N. Eng. J. Med. 334; 1519-1525). Peak bone mass is a determining factor in establishing the risk of osteoporotic fracture (Heaney et al., 2000 Osteoporos. Int. 11; 985-1009), and studies indicate that genetic factors contribute significantly to the variance in peak bone mass.

One of the genes that regulate bone mass has recently been identified via positional cloning. Loss of function mutations in LRP5, a co-receptor for the canonical Wnt signaling pathway (Nusse 2001 Nature 411; 255-256), were found to be associated with Osteoporosis-Pseudoglioma Syndrome (OPPG), an autosomal recessive disorder which shows a reduction of bone density in humans (Gong et al., 2001 Cell 107; 513-523). In addition, two independent kindreds that manifest familial High Bone Mass (HBM) phenotypes were found to harbor a Gly171 to Val substitution mutation (G171V) in LRP5 (Boyden et al., 2002 New. Engl. J. Med. 346; 1513-1521, Little et al., 2002 µm. J. Hum. Genet. 70; 11-18). More recently, additional HBM mutations were reported in the same structural domain of the G171V mutation (van Wesenbeeck et al., 2003 µm. J. Hum. Genet. 72; 763-771). Moreover, mice in which the LRP5 genes were inactivated by gene targeting showed phenotypes similar to those of OPPG patients (Kato et al., 2002 J. Cell Biol. 103; 303-314), and transgenic expression of LRP5G171V in mice resulted in HBM (Babij et al., 2003 J. Bone Res. 18; 960-974). Furthermore, mouse primary osteoblasts showed reduced responsiveness to Wnt in the absence of LRP5 (Kato et al., 2002), while Wnt (Gong et al., 2001) or activated beta-catenin (Bain et al., 2003 Biochem. Biophys. Res. Commun. 301; 84-91) stimulated the canonical Wnt signaling activity and induced the production of the osteoblast marker alkaline phosphatase (AP) in osteoblast-like cells. Together, these pieces of evidence indicate that the canonical Wnt signaling pathway plays an important role in the regulation of bone development.

Wnt

The Wnt family of secretory glycoproteins is one of the major families of developmentally important signaling molecules and has been shown to regulate a wide range of biological and pathophysiological processes that include glucose metabolism, bone remodeling, adipogenesis, neurogenesis, stem cell biology, and tumorigenesis. Until recently, the canonical Wnt signaling pathway was believed to start when Wnt bound to Frizzled (Fz) proteins. The seven transmembrane domain-containing Fz proteins suppress the Glycogen synthase kinase 3 (GSK3)-dependent phosphorylation of beta-catenin through ill-defined mechanisms involving Disheveled proteins. This suppression leads to the stabilization of beta-catenin. In turn, beta-catenin may then interact with transcription regulators, including lymphoid enhancing factor-1 (LEF-1) and T cell factors (TCF), to activate gene transcription (Dale, 1998 Biochem. J. 329; 209-223, Gumbiner et al., 1998 Curr. Opin. Genetics Devel. 8; 430-435, Wodarz and Nusse, 1998 Annu. Rev. Cell Dev. 14; 59-88). Recently, genetic and biochemical studies have provided solid evidence to indicate that co-receptors are required for canonical Wnt signaling in addition to Fz proteins (Nusse, 2001, Pandur and Kuhl, 2001 Bioessays 23; 207-210). The fly ortholog of LRP5 or LRP6, Arrow, was found to be required for the signaling of Wg, the fly ortholog of Wnt-1 (Wehri et al., 2000 Nature 407; 527-530). LRP5 and LRP6 are close homologues which basically function the same way, yet exhibit different expression patterns. In addition, LRP6 was found to bind to Wnt1 and regulate Wnt-induced developmental processes in Xenopus embryos (Tamai et al., 2000 Nature 407; 530-535). Moreover, mice lacking LRP6 exhibited developmental defects that are similar to those caused by deficiencies in various Wnt proteins (Pinson et al., Nature 407; 535-538). Furthermore, LRP5, LRP6 and Arrow were found to be involved in transducing the canonical Wnt signals by binding Axin and leading to Axin degradation and beta-catenin stabilization (Mao et al., 2001 Mol. Cell. 7; 801-809, Tolwinski et al., 2003 Dev. Cell 4; 407-418). The LRP5 or LRP6-mediated signaling process does not appear to depend on Dishevelled proteins (Li et al., 2002 J. Biol. Chem. 277; 5977-5981, Schweizer and Varmus 2003 BMC Cell Biol. 4; 4). In addition, a chaperon protein, Mesd, was identified as required for LRP5 or LRP6 transport to the cell surface (Culi et al., 2003, Cell 112; 343-354, Hsieh et al., 2003 Cell 112; 355-367).

As expected for such an important signaling pathway, the Wnt pathway is subject to a number of controls on the expression and activity of various components of this system. Examples of naturally occurring antagonists include the Dickkopf (Dkk) family of polypeptides, Sclerostin, WISE and sFRPs. Contrariwise, activators of Wnt activity have also been described such as R-Spondin, Norrin and Casein Kinase 1ε.

The involvement of the Wnt pathway in inducing repression or expansion of bone growth was demonstrated in a number of publications that described the various effects of mutations in LRP5 upon skeletal structures that served to give rise to low bone mass (Gong et al., 2001, Streeten et al., 2006 J. Bone Miner. Res. 21; 1433-1442) or increased bone mass (Little et al. 2002, Boyden et al., 2002, van Wesenbeeck et al., 2003). There is even a genetically modified mouse model for osteoporosis, where disruption in both chromosomal copies of LRP5 (a LRP5−/− knockout) generates a low bone mass phenotype (Kato et al. 2002). However, it should be noted that even though the above mentioned references are in regard to LRP5, it should be obvious that intervention in other points along the Wnt signaling pathway could also benefit from administration of compound that have been identified through the processes of the present invention. For recent reviews of the interconnections between the Wnt pathway and bone growth, see cited references Johnson et al., 2004 J. Bone Miner. Res. 19; 1749-1757, Krane 2005 J. Exp. Med. 201; 841-843, Krishnan et al., 2006 J. Clin. Invest. 116; 1202-1209.

LRP5/6

LRP5 and LRP6 are commonly referred to as LRP5/6 in the literature due to a number of shared features-how they are involved in the canonical Wnt system and the sharing of a 70% homology on the amino acid level. As discussed above, LRP5/6 have been identified as co-receptors for Wnt with the various domains of the LRP5/6 proteins likely serving different functions in signal transduction. As described in related U.S. patent application Ser. No. 10/849,067, prediction of the structure of LRP5/6 has allowed the identification of molecules that may bind to YWTD repeat domain III through a virtual screening process followed by verification with biological assays on Wnt activity. A further series of molecules were tested and identified using these processes in related U.S. patent application Ser. No. 11/598,916. Effects that may be tested as being affected by such binding agents may be effects on Wnt signaling itself or effects based on influencing other proteins that are known to interact with LRP5/6. Examples of the latter are effects on repressors of Wnt signaling such as Dkk and Sclerostin.

Control of Wnt Activity

As expected for such an important signaling pathway, the Wnt pathway is subject to a number of controls on the expression and activity of various components of this system. Examples of naturally occurring antagonists include the Dickkopf (Dkk) family of polypeptides, Sclerostin, WIF-1, WISE and sFRPs. In contrast, activators of Wnt activity have also been described such as R-Spondin, Norrin and Casein Kinase 1ε.

Dkk

Dickkopf (Dkk-1) was initially discovered as a Wnt antagonist in Xenopus which plays an important role in head formation during embryogenesis. Thus far, four members of Dkk have been identified in mammals: Dkk1, Dkk2, Dkk3 and Dkk4 (for a review, see Niehrs 2006 Oncogene 25; 7469-

7481). Dkk1 and Dkk2 are believed to inhibit canonical Wnt signaling by simultaneously binding to LRP5 or LRP6 and a single transmembrane protein Kremen. It has also been reported that the LRP5 HBM G171V mutation described above appears to attenuate Dkk1-mediated antagonism to the canonical Wnt signaling. The third YWTD repeat domain of LRP5 have previously been identified as being required for Dkk-mediated antagonism of Wnt signaling (Zhang et al., 2004 Mol. Cell. Biol. 24 4677-4684). In addition, the Dkk-binding cavity and key residues within the cavity have been delineated by site-directed mutagenesis (see related pending U.S. patent application Ser. No. 10/849,067). This cavity is located at the large opening of the barrel-like structure of the YWTD repeat domain that is made of six beta-propellers. Importantly, the two most important residues in the interaction with Dkk, residues Glu721 and Trp780 are located at the bottom of this cavity in the third YWTD domain, suggesting that small molecules that bind to this cavity may be able to disrupt the Dkk-LRP5 interaction by blocking the access to this key residue. Accordingly, as disclosed in related U.S. patent application Ser. No. 10/849,067, a library of compounds was used in a virtual screening process using the structure of LRP5 in conjunction with key residues to estimate binding abilities. A number of different compounds were identified by this process and later shown to have effects upon Wnt activity.

It is expected that many of the compounds that were selected for an ability to bind to LRP5 should also be able to interact with the LRP6 receptor as well, due to the high level of similarity noted above. In general, the areas comprising the YWTD repeat domains of the LRP5 or LRP6 receptor share sufficient amino acid homology with each other that similar structures are formed by each of these domains, but they are dissimilar enough that they vary in some of the dimensions of the pockets formed and have differences in some of the amino acids that are likely to be important in protein/protein interactions. Although predictions of the structure of Dkk have been described previously from the amino acid sequence (Aravind and Koonin 1998 Current Biology 8; R477-R478), this is only a rough estimate of the particular shape that Dkk assumes in its natural state. A purified active preparation of the carboxy CRD domain of Dkk1 was used to obtain precise physical measurements through NMR (Chen et al., 2008 JBC 283; 23,364-23,370) and it was verified that Dkk1 has some physical similarity to colipase. However, the NMR study determined the special positions of the amino acids in a more precise manner, and this structure was used in combination with information from mutagenesis studies to predict the nature of a complex formed between Dkk1 and LRP5/6. As expected, the most stable complex was formed between Dkk1 and the third YWTD domain. The binding of Dkk1 to the other domains (first and second) was capable of occurring but with lower affinities.

The exact mechanism of how Dkk binding to LRP5/6 leads to inhibition of Wnt activity is unclear. One of the earlier studies on the relationship between Dkk and LRP has described the binding of LRP5/6 with Dkk and Kremen resulting in the formation of a complex that undergoes rapid endocytosis thereby decreasing the amount of functional LRP5/6 on the cell surface (Mao et al., 2002 Nature 417; 664-667). Although this provided a potentially simple explanation for Dkk inhibition, more recent studies (Wang et al., 2008 JBC 283; 23,371-23,375) have shown that a dependency upon Kremen for Dkk inhibition was only seen under artificial conditions where both Kremen and LRP6 were over-expressed. Under more normal conditions it was found that even mutants that had lost an ability to bind Kremen were still able to inhibit Wnt activity. Another study examined endogenous levels of LRP6 and showed that treatment with Dkk1 did not lead to LRP down-regulation from the cell surface or affected the rate of internalization of LRP6 (Semenov et al., 2008 JBC 283; 21,427-21,432). Together, these suggest that in addition to LRP removal, a more direct mechanism is involved in Dkk inhibition of Wnt activity.

Other Wnt Inhibitors

In common with Dkk, there are other inhibitors of Wnt activity that may bind to LRP5/6. For instance, a Wnt antagonist called WISE (Itasaki et al., 2003 Development 130; 4295-4305) appears to be a context-dependent regulator of Wnt signaling; it may inhibit or stimulate Wnt signaling in different assays in Xenopus. WISE was also shown to bind to LRP6 and compete with Wnt8 for binding to LRP6. WISE shares 38% amino acid identity with Sclerostin, the gene product of the SOST gene. Loss of function mutations of SOST are responsible for an autosomal recessive Sclerostin skeletal disorder. Previous studies have shown that Sclerostin was highly expressed in osteocytes and that it might act as a bone morphogenic protein (BMP) antagonist, but another study suggested that Sclerostin might not be a functional BMP antagonist and speculated that it might modulate Wnt signaling. Recently, the relationship with Wnt has been clarified by the discovery that Sclerostin binds to LRP5/6 (Li et al., 2005 J. Biol. Chem. 280; 19,883-19,887, Semenov et al., J. Biol. Chem. 280; 26,770-26,775, Ellies et al., 2006 J. Bone Mineral Research). More interestingly, it has been found that Sclerostin most likely binds to the YWTD domains I and II of LRP5/6 (Li et al., 2005). In line with this, it has been disclosed in related U.S. patent application Ser. No. 11/084,668 that compounds initially identified as being able to disrupt interactions between Dkk and LRP5/6 through binding to a YWTD repeat of LRP5/6 are also efficacious at interfering binding between Sclerostin and LRP5/6, as judged both by Wnt dependent assays as well as direct binding studies with an AlkPhos/Sclerostin fusion protein. Although not tested, a similar effect may also possibly be found for Connective-Tissue Growth Factor (CTGF), a Wnt inhibitor that also binds to these regions on LRP5/6 (Mercurio et al., 2004 Development 131; 2137-2147).

Another category of Wnt inhibitors acts more directly by binding to Wnt proteins themselves. For instance, the sFRP family (secreted Frizzled related protein) consists of a series of proteins resembling the Frizzled receptor. While these proteins retain the ability to interact with members of the Wnt family, they are incapable of transmitting the transmembrane signal carried out by Frizzled since they are secreted proteins (Finch et al., 1997 Proc. Nat. Acad. Sci. USA 94; 6770-6775, Leyns et al., 1997 Cell 88; 747-756; Uren et al., 2000 J. Biol. Chem. 275; 4374-4382). As such, they may compete with Frizzled for binding of Wnt molecules and function as competitive inhibitors. It has also been shown that sFRP may bind directly to Frizzled, thereby forming non-functional complexes which may also result in attenuation of Wnt signal (Wang et al., 1987 Cell 88; 757-766; Bafico et al., 1999 J. Biol. Chem. 274; 16,180-16,187). In either case, sFRPs may act by preventing binding of Wnt to its receptor. Other such proteins are WIF-1 (Hsieh et al., 1999 Nature 398; 431-436) and Cerberus (Piccolo 1999, Nature 397; 707-710) both of which also seem to function by preventing Wnt from binding to Frizzled.

Wnt Activators

As expected with such a sophisticated system, proteins have also been identified that act as activators of the Wnt system, including R-Spondin, Norrin and Casein Kinase 1ϵ. R-Spondin (Kazanskaya et al., 2004 Developmental Cell 7;

525-534; Kim et al, 2006 Cell Cycle 5; 23-26) has been shown to stimulate Wnt activity. Further research has shown that there are four different forms of R-Spondin in the mammalian cell, each of which is capable of stimulating Wnt activity, although at different levels, with RSpo2+ RSpo3>RSpo1>RSpo4 (Kim et al., 2008 Mol. Biol. Cell 19; 2588-2596). Although R-Spondin is regarded as an activator of the Wnt pathway, it is not a substitute for Wnt since it requires the presence of Wnt for its activity (Binnerts et al., 2007 Proc. Nat. Acad. Sci. (USA) 104; 14,700-14,705). It therefore enhances the ability of Wnt to generate a signal. A potential mechanism for the synergistic action of R-Spondin has been postulated with regard to the internalization of LRP receptors after Dkk binding, where the presence of R-Spondin has been shown to reduce the extent of this process (Binnerts et al., 2007). However, this mechanism is still a matter of controversy as some groups claim that there is direct binding of R-Spondin to LRP receptors (Nam et al., 2006 JBC 281; 13,247-13,257 and Wei et al., 2007 JBC 282; 15,903-15,911), whereas other groups believe it is an indirect effect of binding through Kremen rather than LRP itself (Binnerts et al., 2007). However, similar to the effects with Dkk, Wnt activity in the presence of R-Spondin may also be suppressed by Sclerostin, a protein that is not known to involve interaction with Kremen. R-Spondin is believed to interact with Frizzled as well (Nam 2006, Wei 2007).

Another activator of the Wnt system was discovered through studies of a congenital blindness defect, Norrie Disease (pseudoglioma), where it was found to be due to mutations linked to a protein of unknown function, which was named "Norrie Disease Protein" or "Norrin" (Berger et al., 1992 Nat. Genet. 1; 199-203; Chen et al., 1992 Nat. Genet. 204-208). Subsequent work has shown that Norrin is involved in the Wnt signaling system (Xu et al., 2004 Cell 116; 883-895) and more specifically linked to binding to the CRD portion of the Frizzled receptor, Norrin seems to function as a Wnt analogue requiring both Frizzled and LRP5/6 for activation of the Wnt pathway (Xu et al, 2004) even though it is unrelated to the Wnt family. A high level of specificity is seen where Norrin binds to Frz-4 but none of the other 14 mammalian Frizzled and sFRP CRD domains (Smallwood et al., J. Biol. Chem. 282 4057-4068). Interestingly, Bex and Bhat (U.S. Patent Application No. 20070196872 published Aug. 23, 2007) showed that after transfection with Norrin, LRP5 and Fz4 plasmids, Wnt reporter activity could be suppressed if Dkk was added as well, indicating that Wnt activity derived from Norrin activation was still susceptible to Dkk binding to LRP5.

Another activator of the Wnt system is Casein Kinase 1ε (Peters et al., 1999 Nature 401; 345-350; Sakanaka et al., 1999 Proc. Nat. Acad. Sci. USA 96; 12,548-12,552). This activator is involved in a complex series of reactions. For instance, there is an interaction between Casein Kinase 1ε (CK-1ε) and Wnt—the addition of Wnt leads to activation of CK-1ε and withdrawal of Wnt leads to inactivation of CK-1ε (Swiatek et al., 2004 J. Biol. Chem. 279; 13,011-13,017). In addition, it has been noted that CK-1ε binds to LRP5/6 and phosphorylates LRP5/6 in at least three different sites, events that might lead to increased activity (Swiatek et al., 2006 J. Biol. Chem. 281; 12,231-12,241).

Also, a recent development has shown that a complex formed between Parathyroid Hormone (PTH) and its receptor (PTH1R) may bind to LRP6 and stimulate Wnt activity (Wan et al., 2008 Genes & Development 22; 2968-2979). Although it was not tested in this study, it is likely that a related protein, Parathyroid Hormone related Peptide (PTHrP), may also induce this effect since it is similar to PTH and binds to the same receptor. This stimulation may be similar to that of Norrin in that it didn't seem to require the addition of exogenous Wnt to provide a substantial boost in the TCF/LEF reporter activity.

As described previously in related pending U.S. patent application Ser. No. 10/849,067, knowledge of the structure of a protein involved in a protein-protein interaction allows for a virtual screening for molecules that may interfere with that interaction by binding to a "hot spot" involved in the interaction, thereby potentially affecting the Wnt signal system. Also, as described in related pending U.S. patent application Ser. No. 11/598,916, identification of a molecule that binds to such a locus on a Wnt related protein may also have utility when the target protein has functions outside of the Wnt pathway as well.

Virtual screening programs used for this purpose enjoy scale versatility that extends from small molecules to macromolecules. For instance, amino acids, oligopeptides, polypeptides and intact proteins may all be evaluated in terms of their ability to be "docked" onto a site of a target protein. For example, as was discussed above, the determination of the structure of the Dkk CRD domain allowed a prediction for the structure of a complex between Dkk and LRP as well as evaluations of binding of Dkk to the various YVVTD domains of LRP5/6. Thus, the only limitation of a candidate molecule being screened for an ability to bind to a target molecule is solely based on the availability of its structure and the computational power devoted to the analysis. As such, as described in these applications, a wide variety of material may be used as a source of a virtual library including small molecules, cyclic molecules, heterocyclic organic molecules, lipids, charged lipids, polar lipids, non-polar lipids, sugars, glycolipids, peptides, oligopeptides, polypeptides, proteins, glycoproteins, lipoproteins, nucleic acids, chemical, as well as fragments or analogues of the foregoing. Examples of small molecules that may bind to the Dkk binding site of LRP5/6 and affect Wnt signaling are disclosed in related pending U.S. patent application Ser. Nos. 10/849,067, 11/084,668 and 11/598,916. A similar study was undertaken with regard to Dishevelled, another member of the Wnt signal pathway in related pending U.S. patent application Ser. No. 11/097,518 where a small molecule that was essentially a peptide analogue with substitution of two ether bonds in place of two peptide bonds was selected by a virtual screening process for binding to the PDZ domain of Dishevelled and later shown to block Wnt signaling.

One of the consequences of the identification of molecules that may affect Wnt activity is their potential role in the treatment of diabetes and other metabolic diseases, since it has been noted that increasing Wnt activity has positive effects upon glucose metabolism. For instance, animals that have genetic modifications such that they overexpress Wnt10b may be challenged with high fat diets and show a reduced level of triglycerides, a lower bodyweight, hyperinsulinemia and improved glucose homeostasis compared to their normal counterparts (Aslanidi et al., 2007). Administration of Wnt proteins may also be undertaken in vivo and show effects on glucose metabolism. For instance, experiments with ob/ob and agouti mice have shown that exogenous Wnt 10b may provide glucose tolerance and an increased sensitivity to insulin (Wright et al. 2007 Diabetes 56; 295-303). Wnt protein may also offer cells a protection from apoptosis derived from high glucose levels (Lin et al. 2006, J. Am. Soc. Nephrol. 17; 2812-2820, Chong et al., 2007 Curr. Neourovasc. Rev. 4; 194-204). Interaction of Wnt signaling with cholesterol metabolism has also been seen in studies where cholesterol levels were artificially depleted resulting in activation of the Wnt pathway signaling system and induction of myogenic differentiation (Mermelstein et al. 2007 Differentiation 75; 184-192; Portilho et al., 2007 FEBS Letters 581; 5787-5795).

As discussed above, in previous related pending applications we have described the use of virtual screening to identify non-naturally occurring molecules that could be used to artificially manipulate the effects of protein/protein interactions in the Wnt signaling system as well as protein interactions that may not be involved with Wnt but do interact with the LRP family. The application of small molecules that have been previously demonstrated to increase Wnt activity are in concordance with the diabetes results discussed above. For instance, Example 13 of related pending U.S. patent application Ser. No. 11/598,916 demonstrated that when compounds which were identified by virtual screening were tested with mice on a high caloric intake, they were able to affect glucose metabolism by: (a) decreasing the glucose levels to almost normal levels ($IC_{15}$, IIIC3 and M01); (b) decreasing serum triglyceride levels (IC15 and M01); and (c) even decreasing serum cholesterol levels (M01). A further discovery was that when one of these compounds (IIIC3) was tested in a diabetic model (the db/db mouse), it was also able to show a significant drop in plasma insulin levels as well as a better response in a glucose tolerance test. The connection between Wnt pathway elements and sugar metabolism was also found in studies of mice lacking one or both copies of Dkk2: the double (Dkk−/Dkk−) mutant had much lower fasting glucose levels compared to the wildtype mice (Dkk+/Dkk+) and the heterozygous mice (Dkk+/Dkk−) had levels that were intermediate between the double mutant and wild type strains (Example 6 of related pending U.S. patent application Ser. No. 12/221,863). Thus it appears that a characteristic of pharmacological agents that have been discovered to raise Wnt activity is the potential utility in treatment of conditions such as diabetes.

DETAILED DESCRIPTION OF THE INVENTION

Figure 1:
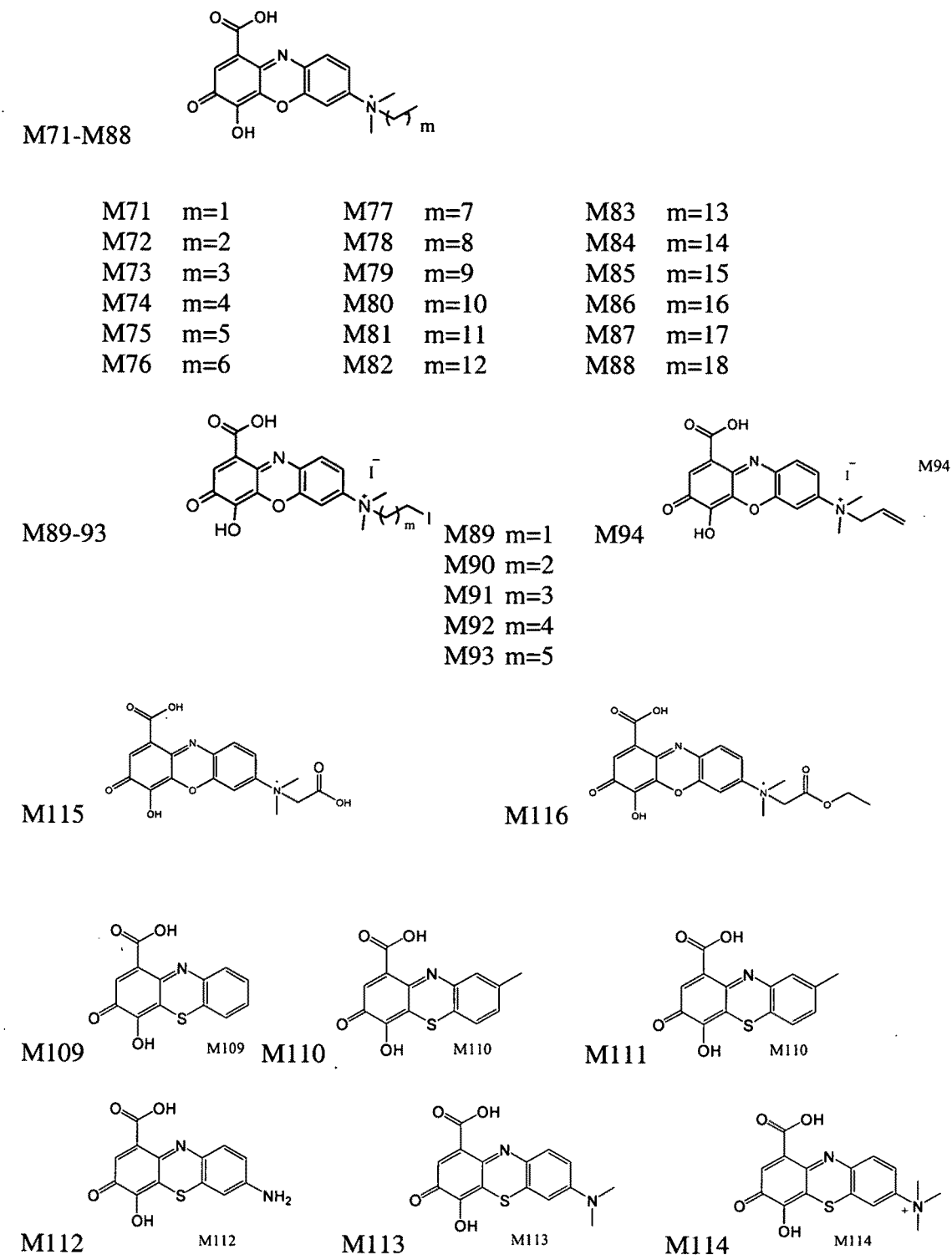
FIG. 1. Structures of M71-M94 and M109-M116.

The present invention describes a number of compounds (or analogues of compounds) that have been screened on the basis of their ability to bind to LRP5/6 and subsequently influence Wnt activity in biological assays. Such properties should find application in the treatment of a number of diseases that are affected by the activities of members of the Wnt pathway. Compounds identified by this process may be able to raise Wnt activity either by directly increasing Wnt activity itself or by indirectly blocking suppression of Wnt activity by components such as Dkk or Sclerostin. As described above, some of the compounds that have been identified in previous related pending applications as being able to raise Wnt activity have been demonstrated to be able to produce effects that would provide health benefits in diseases that are related to defects in glucose metabolism/homeostasis, such as diabetes. The present invention demonstrates that other compounds that have been selected for this ability enjoy effectiveness in controlling glucose metabolism, thereby confirming the concept that this characteristic is generally applicable to diseases such as diabetes.

The administration of compounds disclosed in the present invention may take place by the use of prodrugs. A prodrug is a pharmacological substance (drug) that is administered in an inactive (or significantly less active) form. Once administered, the prodrug is metabolized in vivo into an active metabolite. The rationale behind the use of a prodrug is generally for absorption, distribution, metabolism and excretion (ADME) optimization. Prodrugs are designed to improve oral bioavailability, with poor absorption from the gastrointestinal tract being the limiting factor. Prodrugs have one or more groups appended to their structures such that after administration of the prodrug to a subject, native metabolic pathways convert the prodrug into an active compound. Such modifications may provide increased stability, higher solubility, enhanced uptake or targeting capabilities prior to the prodrug reaching its intended site of action; groups that may provide these benefits while being capable of allowing a conversion event are known to those skilled in the art. Commonly used modifications include the use of ester, amide, carbonate, carbamate, azo and glycosidic bonds. (Illustrative examples of such processes are included in U.S. Pat. No. 5,070,082, U.S. Pat. No. 5,340,825; U.S. Pat. No. 7,220,754, U.S. Patent Application No. 200602055674, WO/2004/084949, Berry et al., 1997 J. Chem. Soc. Perkin. Trans. 1; 1147-1156, Hu 2004 IDrugs 7; 736-742, Stella et al., 2007 Adv. Drug Deliv. Rev. 59; 677-694, Juillerat-Jeannert 2008 Drug Discovery Today 13; 1099-1106, Rautio et al., 2008 Nat. Rev. Drug Discov. 7; 255-270, (all of which are incorporated herein by reference).

In one particular embodiment, the present invention discloses a series of new compounds able to induce effects upon Wnt activity. In the present invention, the screening process described in previous related applications has been applied to both a physical library of a series of compounds and a virtual library of compounds that were designed according to results described in previous related applications, thereby disclosing new compounds that also affect Wnt activity. A physical library allowed immediate access to compounds of interest for biological assays. The virtual library gave more flexibility to the nature of groups appended to a "core structure" but required a series of chemical reactions to synthesize compounds for assays. This approach has enjoyed success since a number of different compounds were identified from both the physical and virtual libraries that were later shown to have various effects on Wnt activity. As described in related U.S. application Ser. No. 11/598,916, compounds that have been selected through a screening process designed to identify compounds that bind to LRP5/6 may produce a variety of different effects upon Wnt activity. In accordance with this, it should be noted that the compounds that were selected for LRP5/6 binding in the present invention have been shown to demonstrate the variety of effects that may be expected to ensue from binding where the invention discloses Wnt inhibitors, Wnt stimulators and compounds that block the action of Wnt suppressors such as Dkk.

Another aspect of the present invention is addressed towards the design of peptides within a region that bind to the interaction sites of LRP5/6 and Dkk. As previously discussed, a virtual screening process could be carried out where a permutational library of small peptides is substituted for the small organic molecules. In contrast, since the interaction sites are known, peptides that make up these regions or key amino acids may be derived from the sequences of appropriate portions of either binding partner. With this latter method, the virtual screening step may be used or a small physical library of Dkk or LRP5/6 sub-sequences may be tested empirically for effects on Wnt activity. Although this approach is discussed in terms of LRP5/6 and Dkk as binding partners, it should be understood that the same methodology may also be applied to any pair of proteins involved in protein-protein interactions, especially with regard to proteins involved in the Wnt signaling system or with LRP5/6 in non-Wnt based interactions. After identification of a suitable peptide, a compound may be derived from an artificial equivalent of such a peptide. Examples of such artificial equivalents may comprise but not be limited to the peptide mimetics described in related pending U.S. patent application Ser. No. 11/097,518, the substitution of the dextro isomers instead of the normal levo forms, and peptidomimetics such as those described in Hammond et al., 2006 Chem. & Biol. 13; 1247-1251. Other examples of analogs that may find use with the present invention are "unnatural amino acids" where it is understood that in the context of the present invention the term "unnatural amino acids" refers to amino acids that are not genetically encoded: they are not represented by a nucleotide triple codon. This would include the dextro isomers discussed above as well as other amino acids such as Aib (amino-isobutyric acid), bAib (3-aminoisobutyric acid), Nva (norvaline), β-Ala, Aad (2-amino-adipic acid), bAad (3-aminoadipic acid), Abu (2-aminobutyric acid), Gaba (γ-aminobutyric acid), Acp (6-aminocaproic acid), Dbu (2,4-diaminobutyric acid), TMSA (trimethylsilyl-Ala), alle (allo-Isoleucine), Nle (Norleucine), tert.Leu, Cit (Citrulline), Orn, Dpm (2,2'-diaminopimelic acid), Dpr (2,3-diaminopropionic acid), α- or β-Nal, Cha (cyclohexyl-Ala), hydroxy-proline, Sar (Sarcosine) etc., cyclic amino acid units and $N^\alpha$-alkylated amino acid units, e.g. MeGly ($N^\alpha$-Methyl-glycine), EtGly ($N^\alpha$-ethylglycine) and EtAsn ($N^\alpha$-ethyl-asparagine).

The role of LRP5/6 in Wnt signaling in a number of different processes has been well established. For example, it has been recently shown that proteins involved in cholesterol metabolism are involved in direct binding to LRP6 (Wan et al., 2008 Genes 22; 2968-2979) thereby providing an explanation of previous results that demonstrated an interaction between cholesterol and Wnt signaling. In this study, it was shown that while neither parathyroid hormone (PTH) or the PTH receptor alone bound to LRP6, the complex of PTH and its receptor would bind to the extracellular portion of LRP6. Presumably, the binding event generated allosteric changes in either the structure of PTH, the PTH receptor (that presented a surface that would bind to LRP6) or the composite surface derived from the PTH/Receptor complex. The present invention enjoys the advantage that: a) proposed structures for the paraththyroid related peptide (PTHrP)/receptor and PTH/receptor complex have been published (Gensure et al., 2001 JBC 276; 28,650-28,658; Gensure et al., 2005 BBRC 328; 666-678); and b) the binding of this complex to LRP6 makes it likely that the binding site is one of the YWTD derived β-propeller structures because it stimulates Wnt signaling. Also, as described in these references, numerous mutations and their effects have been noted. Due to the similarity of PTHrP to PTH in terms of binding to the PTH receptor, this protein may also be used in a similar manner. Thus, a computer simulation may be obtained that describes the structures of the surfaces of the complex that interact with LRP6 and a series of peptides may be designed that mimic these binding points in the same way described above for Dkk.

As previously described, such peptides may be normal amino acids or they may comprise amino acid analogues: they may be "unnatural" in the sense of being amino acids that are not genetically encoded. For example, a series of non-naturally occurring amino acids have also been used to design peptides derived from the sequence of the first 34 amino acids of PTH since this portion of the protein was known to be involved in receptor binding (see U.S. Pat. No. 5,969,095 and U.S. Patent Application No. 20080318838, both of which are incorporated herein by reference). As such, amino acid analogues that may be of use in this aspect of the invention as well as other previously disclosed embodiments involving virtual screening may include, but not be limited to "unnatural amino acids" such as the D isomers of the natural levo isomers of amino acids described previously, as well as Aib (aminoisobutyric acid), bAib (3-aminoisobutyric acid), Nva (norvaline), β-Ala, Aad (2-amino-adipic acid), bAad (3-aminoadipic acid), Abu (2-aminobutyric acid), Gaba (γ-aminobutyric acid), Acp (6-aminocaproic acid), Dbu (2,4-diaminobutyric acid), TMSA (trimethylsilyl-Ala), aIle (allo-Isoleucine), Nle (Norleucine), tert.Leu, Cit (Citrulline), Orn, Dpm (2,2'-diaminopimelic acid), Dpr (2,3-diaminopropionic acid), α- or β-Nal, Cha (cyclohexyl-Ala), hydroxy-proline, Sar (Sarcosine) etc., cyclic amino acid units and $N^\alpha$-alkylated amino acid units, e.g. MeGly ($N^\alpha$-Methyl-glycine), EtGly ($N^\alpha$-ethylglycine) and EtAsn ($N^\alpha$-ethyl-asparagine). Also included are amino acids in protected form, where an amino acid in protected form is meant to be a natural or unnatural amino acid containing, for example, a side chain including an heteroatom such as O, S or N which may be protected with an O-, S- or N-protecting group.

Although many of the compounds in the present invention, as well as other ones described in previous related applications, have been selected on the basis of a predicted binding potential derived from a virtual screening process, biological assays should be carried out to measure the effects of such potential binding events. Assays that have been used for this purpose have included Wnt activity as measured by a Wnt-dependent luciferase assay as well as assays having biological markers such as insulin response and glucose response, cytokine assays, as well as assays exhibiting potential growth inhibition in the case of transformed cell lines. Another biological assay that has utility in characterizing compounds includes binding assays. These may be used to identify the ability of a compound to bind to a target, or the ability of a compound to prevent binding by some other component. In regard to the former approach of binding ability identification, related pending U.S. patent application Ser. No. 10/849,067 disclosed a series of compounds that were predicted to bind to the third YWTD Domain of LRP5 by the virtual screening process and subsequently tested for the ability to affect binding of an AlkPhos/Dkk fusion protein. In Table I of the '067 application a number of the compounds selected by the virtual screening process were seen to directly interfere with the ability of Dkk to bind to cells that had been transfected with an LRP5 expression vector.

Specificity of the binding to the intended target may be measured in such a binding assay by a parallel assay where the LRP5 protein is lacking YWTD Domain III, as described in the '067 application. In another embodiment of the present invention, an assay is also described where a panel is used comprising other proteins carrying YWTD derived β-propellers. These proteins may include LRP6 as well as the other members of the LRP family including LRP1, LRP1B, LRP2, LRP4, LDLR, VLDLR, LRP8 and LR11/sorLA-1. Non-LRP proteins also comprising a YWTD derived β-propeller such as nidogen, osteonitogen, EGF precursor, and "sevenless" may also be used. Thus, the ability of a compound of interest to be able to specifically bind to a particular YWTD derived β-propeller may be ascertained.

The various proteins with a YWTD derived β-propeller comprise a set of receptors that interact with a large number of different ligands. Consequently, these proteins should be involved in a variety of metabolic functions and potentially contribute to disease processes. It is apparent then, that compounds that bind to these proteins and alter their functionality can potentially provide relief from symptoms or conditions that these proteins are associated with. The connection between LRP5/6 and various diseases have been discussed above, but other proteins with a YVVTD derived β-propeller have also been shown to be involved in pathological processes such as Alzheimer's (Cam and Bu 2006 Molec. Neurodegen. 1; 8, Jaeger and Pietrzik 2008 Curr. Alzheimer Res. 5; 15-25), atherosclerosis (Llorente-Cortes and Badimon 2005 Arterioscler. Thromb. Vasc. Biol. 5; 497-504, Boucher and Gotthardt 2004 Trends in Cardiovascular Med. 14; 55-60), chronic fibrosis (Yang et al., 2004 FASEB Journal 18; 1920-1921), hypercholesterolemia (Lehrman et al., 1987 Cell 48; 827-835), inflammation (Zurhove et al., 2008 Sci. Signal 1; ra15, Gaultier et al., 2008 Blood 111; 5316-5325), diabetes (Tamaki et al., 2007 Molecular Pharmacol. 72; 850-856) and neuronal death due to HIV infection (Eugenin et al., 2007 Proc. Natl. Acad. Sci. (USA) 104; 3438-3443).

It is another aspect of the present invention to provide in vitro systems for carrying out binding assays. In one such system, an assay is disclosed where a first member of an interacting protein binding pair is attached to a solid surface such as a bead or a plate and measuring the binding ability of a labeled version of a second member of the binding pair is measured. In the context of the present invention such binding pairs may be members of the Wnt signaling system or they may be selected from proteins with YWTD derived β-propellers and their appropriate binding partners (Wnt or non-Wnt). By carrying out such assays in the presence of compounds of interest, these compounds may be physically characterized in terms of effects they may exert on the ability of a binding pair to interact. Thus, the method previously described for a cell based assay with LRP5/6 as a target may be replaced by an in vitro system where LRP5/6 (and/or other members of the LRP family) may be attached to a surface and used in conjunction with the Alkphos/Dkk fusion protein described previously. Such a system may also be used with directly labeled proteins but more sensitivity will be achieved by the use of an enzyme labeled binding partner. On the other hand, the identity of the constituents used in the described assay may be reversed and a protein such as sclerostin or Dkk may be attached to the solid support and a binding partner such as an enzyme linked-LRP5/6 molecule may be used as the probe. Such a system is exemplified in Example 19 of the present invention. Consequently, it is understood that either partner of a protein/protein interaction involved in the Wnt signal pathway may be used with such assays as well as either partner of a protein/protein interaction involving proteins with YWTD derived β-propellers. Such assays may provide fast and efficient means for assaying the effects of compounds of interest on such interactions.

Another assay that may be used is a co-immunoprecipitation assay as described in Ai et al., 2005 (Mol. Cell. Bio. 25; 4946-4955) where the LRP5/6 is incubated with DKK that has a detectable marker followed by precipitation of the LRP5/6 as well as any bound Dkk. In the method of the present invention, various amounts of a compound of interest may be present prior to immunoprecipitation to measure the effects of the compound on the association between LRP5/6 and binding partners such as Dkk or Sclerostin.

In another aspect of the present invention, molecules that have been identified as binding to a member of the Wnt pathway may be labeled in order to investigate their properties. The use of labeled moieties may employ a variety of different formats for detecting or quantifying binding abilities of the compounds. For instance, the molecule may be labeled with a fluorescent tag and tested for binding to appropriate targets that have been immobilized to a solid support. Indirect means of signal generation may also be employed. For instance, ligands such as biotin, digoxygenin or DNP may be attached by means of a linker arm and detected by means of the appropriately labeled binding partner. The converse may also be carried out where the label allows fixation of the molecule of interest to a solid support and all or a portion of a target protein labeled by some other means is bound to the support through interactions with the immobilized molecule. In this case again, there may be direct or indirect labeling of the target protein. An example of this approach is described in Examples 16 and 17.

The binding of the labeled compound to the target of interest may be carried out by a variety of means and formats. For instance, homogenous assays may be carried out where there are changes in properties associated with a binding event. An example of this method is where both the compound and its receptor are labeled and an energy transfer event can be detected. Two phase assays may also be used where the intended target is bound to a solid matrix and fixation of the labeled compound is detected.

The binding of the labeled compound to the target of interest can be carried out by a variety of means and formats. For instance, homogenous assays can be carried out where they are changes in properties associated with a binding event. An example of this method is where both the compound and its receptor are labeled and an energy transfer event can be detected. Two phase assays may also be used where the intended target is bound to a solid matrix and fixation of the labeled compound is detected.

In another aspect of the present invention, a competitive assay is described where a compound that has been found to bind to a member of the Wnt signaling system, such as those previously described as binding to LRP5 (the U.S. patent application Ser. No. 10/849,067) or to Disheveled (U.S. patent application Ser. No. 11/097,518), is included in an assay testing the characteristics of another compound. Specifically, if compound X is known to bind to LRP5/6, X and Y (a test compound) are used together to observe the effect on X. This aspect of the present invention may be applied to cell based assays such as the AlkPhos-Dkk binding assays discussed above as well as the in vitro assay methods also discussed above. Although the preceding assay methods may be used to characterize compounds after they have been selected from a virtual screening process, these assays may also be used as the primary identification method, such as for a high throughput screening processes for testing compounds, without a first selection step.

In another embodiment of the present invention, an improved methodology of testing potential pharmacological agents in biological assays on Wnt activity is described. Although the use of the LEF reporter system has allowed the generation of data concerning the effects of such molecules, it is limited in the amount of signal it provides with regard to effects on either Wnt activity or inhibitors of Wnt activity such as Dkk or Sclerostin. The present invention discloses that in addition to Wnt itself, factors that enhance Wnt activity may be included in assays to both increase the dynamic range of the assay as well as possibly providing more definitive differences between Wnt alone compared to Wnt in the presence of natural inhibitors such as Dkk or Sclerostin. Examples of such activators may include R-Spondin, Norrin Casein Kinase 1ε, PTH and PTHrP. Assays for detecting the effects of compounds of interest may then be carried out where the assays have been modified to include these activators. In some cases, a particular co-factor is part of the effect; for example, activation of Wnt activity by the addition of Norrin depends upon the interaction of Norrin with a particular species of Frizzled: Frz4. In such a case, use may be made of the endogenous levels of the co-factor, or alternatively if the levels are inadequate, the levels of such a co-factor may be raised artificially, for example by transfection with a nucleic construct coding for the co-factor. Example 18 shows the results of using R-Spondin as an activator where it may be seen that there is a dramatic effect in overall Wnt activity and an increased effect of inhibition of suppression of Wnt activity in the presence of Dkk. Even when the Wnt activity has been reduced by Dkk, the presence of R-Spondin provides sufficient stimulation. The result of this is that the signal for the Dkk suppressed Wnt signal is approximately equal to the signal produced in the absence of both Dkk and R-Spondin. These assays may then be applied to test the effects of potential pharmacological agents on Wnt activation or suppression. Such agents may have been selected through any means including but not limited to virtual screening programs and high throughput screening procedures.

Thus in one embodiment of the present invention, an assay is described that comprises the addition of: a) Wnt; b) a component that increases Wnt activity (i.e. a Wnt activator); and/or c) a compound whose effects upon Wnt activity needs to be ascertained.

When appropriate controls are provided, the effects on Wnt itself as well as the effects on the induction of Wnt activity by the activator may be ascertained. As such, carrying out this assay may involve some or all of the following: Wnt; Wnt & the test compound; Wnt & Activator; and/or Wnt & test compound & Activator. Such a test may be further expanded to include another factor that influences Wnt signaling. For instance, both Dkk and Sclerostin are known to inhibit Wnt activity, and the cited related patent applications as well as the present application have disclosed experimental data on the effects of selected compounds on Dkk and Sclerostin inhibition of Wnt activity. The assay described above may therefore be utilized by inclusion of these other Wnt factors (Factor X) as well as the Wnt Activators.

Thus in one embodiment of the present invention, an assay is described that comprises the addition of: a) Wnt; b) a Wnt Activator; c) Factor X; and/or d) a compound whose effects upon Wnt activity needs to be ascertained.

A series could therefore include any or all of the following: Wnt; Wnt & Test compound; Wnt & Activator; Wnt & Test Compound & Activator; Wnt & Factor X; Wnt & Factor X & Test Compound; Wnt & Factor X & Activator; and/or Wnt & Factor X & Activator & Test Compound.

As mentioned above, certain Wnt Activators such as R-Spondin are Wnt dependent and only augment the ability of Wnt to induce a signal, while others such as Norrin and PTH act as an analogue of Wnt, allowing them to be used as substitutes for Wnt, or in conjunction with Wnt.

Another aspect of the present invention is concerned with interactions between Dkk and Kremen. When the Dkk/Kremen complex is disrupted, Dkk activity is decreased. The formation of a complex between Dkk and Kremen has been shown to lead to endocytotic events that result in LRP5/6 being removed from the cell surface (Mao et al., 2002). More recently, Wang et al., (2008) noted that certain mutations in Dkk may reduce or eliminate binding between Dkk and Kremen while remaining functional in suppressing Wnt activity. As such, Dkk mediated suppression is presumably taking place in the absence of LRP5/6 removal since this has been shown to be dependent upon Kremen binding. Since the structure of Dkk has been determined (Chen et al., 2008) and the particular amino acids critical to Kremen binding have been establish ($Arg^{197}$, $Ser^{198}$ and $Lys^{232}$), a virtual screening program may be used for the discovery of molecules that block or disrupt Dkk/Kremen interactions. Molecules of this nature may have interesting properties since they may affect one aspect of Dkk mediated inhibition of Wnt (LRP5/6 removal) while leaving the inhibition of Wnt that is Kremen-independent intact.

Although the possibility of a search for compounds that may affect binding between Dkk and Kremen have been described by Niehrs and Mao in U.S. Patent Application No. 20050244826, they only offer a generalized method that looks for compounds that bind to either Dkk or to Kremen. Such an undirected search would find numerous compounds that bind to sites that are involved in the Dkk/Kremen interaction. In contrast, the present invention takes advantage of new information that describes the structure of the Dkk/Kremen complex thereby providing detailed information on the particular Dkk/Kremen surfaces that are involved in the interaction, as well as the identity of key amino acids that are involved in this interaction. Thus, in the present invention, the binding sites for the Dkk/Kremen interaction are the targets and are what would be used for virtual screening.

As discussed above, the discovery of effects on the Wnt pathway by various compounds derived from a virtual screening program allows an expansion of testable compounds by selectively modifying groups at various locations on what are termed "core" or "sub-core" structures. Thus, a set of related analogues with a series of methodical substitutions may be designed and tested for efficacy. A number of novel compounds were described in U.S. patent application Ser. No. 11/598,916 ("the '916 application") that were successfully identified by this type of approach. The present invention discloses an expansion on this methodology where a further series of compounds have been designed using various compounds as models and varying the identity of the side chains. In this series of compounds, M71-M94, M115 and M116 are similar to the series carried out for M01-M70 and are based on various substitutions for R15 of structure VI of the '916 application, thereby having the following structure:

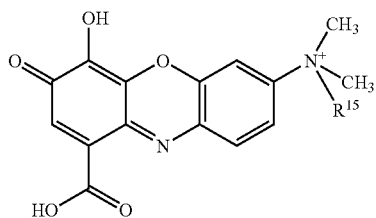

The various compounds from this series are shown in FIG. 1. It should be noted that the designs for M71, M72, M73 and M74 have the same structures as M02, M03, M05 and M09 described in the '916 application.

Since the '916 application had also shown effectiveness for what was termed a "subcore" based on the structure of gallic acid, variations of this molecule were investigated. The structure of gallic acid is:

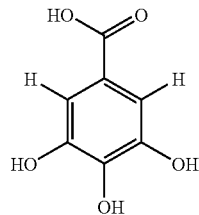

In one variation, a series of gallic acid derivatives were designed with an amine group added to one of the positions on gallic acid as follows:

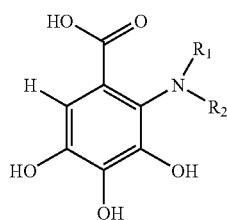

Figure 2:
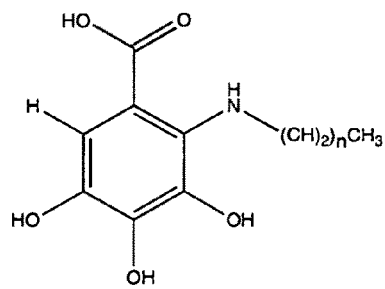
FIG. 2. Structures of M117-M156.
Figure 2:
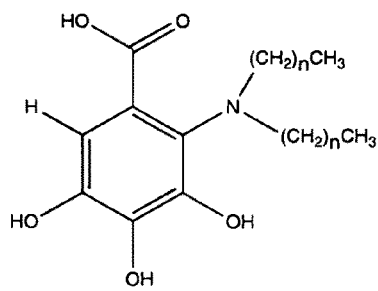
Figure 3:
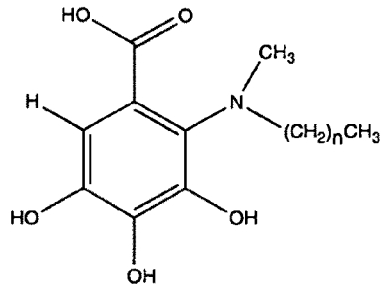
FIG. 3. Structures of M157-M193.
Figure 3:
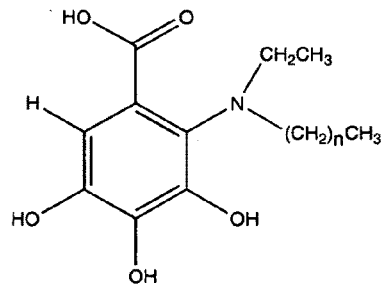
Figure 4:
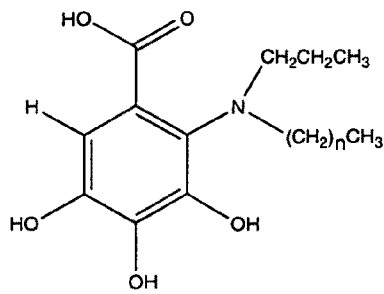
FIG. 4. Structures of M194-M226.
Figure 4:
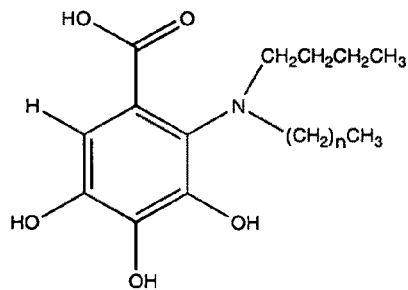

In one set (M103-M108), $R_1$ was hydrogen and $R_2$ was a variety of substituted aromatic rings (FIG. 6); in another set, (M117-136) $R_1$ was hydrogen and $R_2$ was a series of aliphatic chains (FIG. 2) and in a third series (M137-M226) both $R_1$ and $R_2$ were selected from various combinations of aliphatic chains (FIGS. 2, 3 and 4).

In another series of variations of gallic acid derivatives, the same site was modified by adding an azo group linking various aromatic rings to the gallic acid moiety to create a series with various substitutions at $R_1$ on the aromatic ring portion as follows:

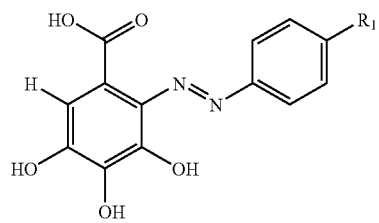

Figure 5:
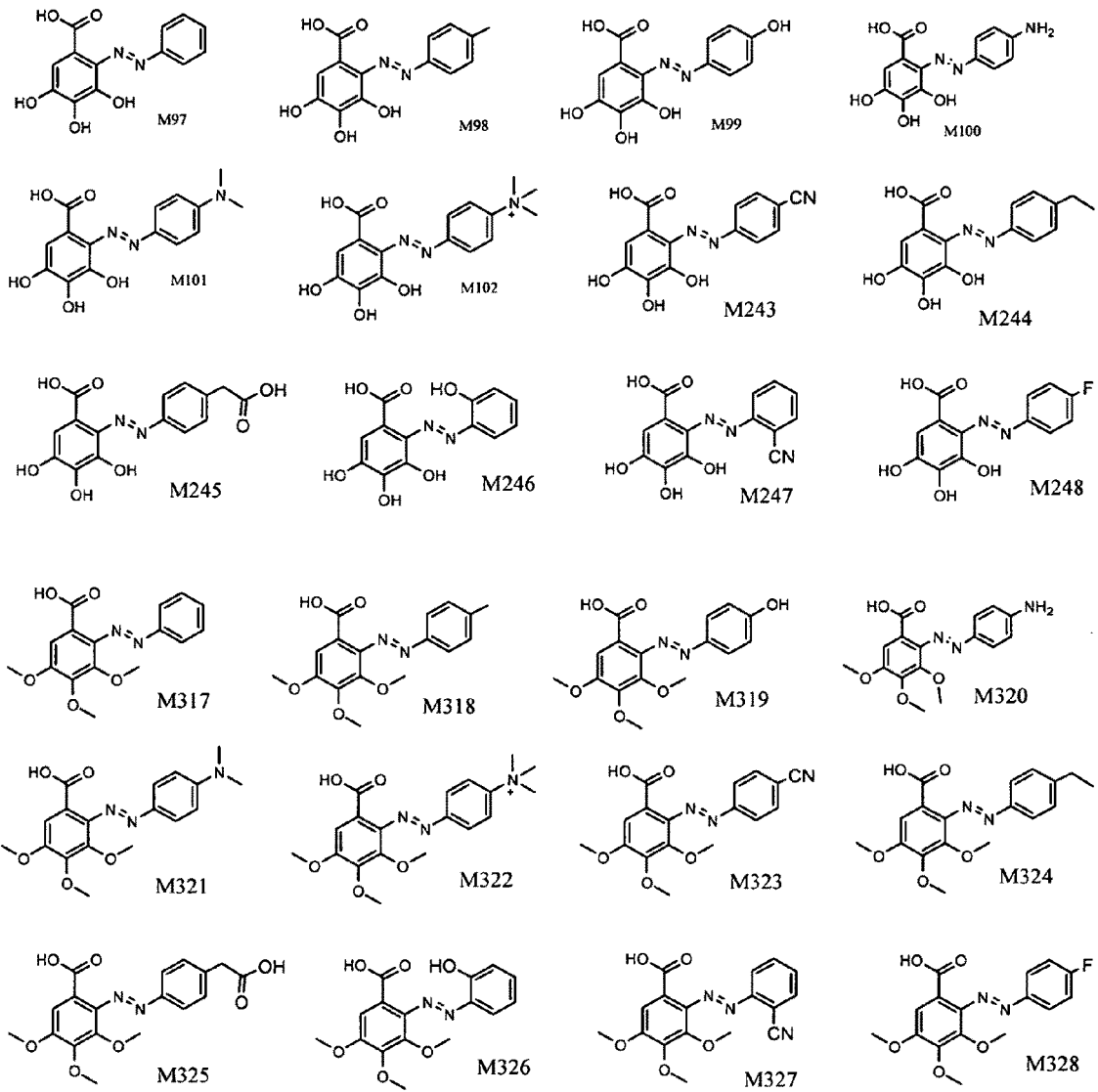
FIG. 5. Structures of M97-M102, M243-M248 and M317-M328.

This series is designated M97-M102 and M243-M248, as shown in FIG. 5.

A variation on the preceding set was also made by substituting methoxy groups for the hydroxyl groups and varying the identity of $R_1$:

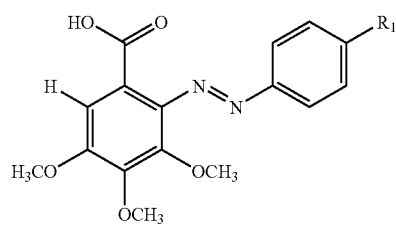

This series was designated M317-M328 and is also shown in FIG. 5.

Another set of gallic acid derivatives was designed by having an imino linkage to a heteroaromatic ring with various substituents:

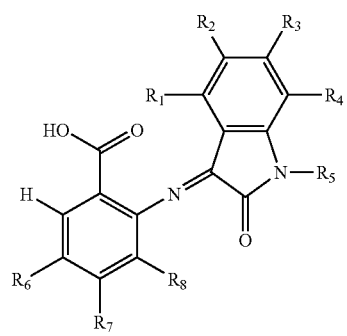

Figure 6:
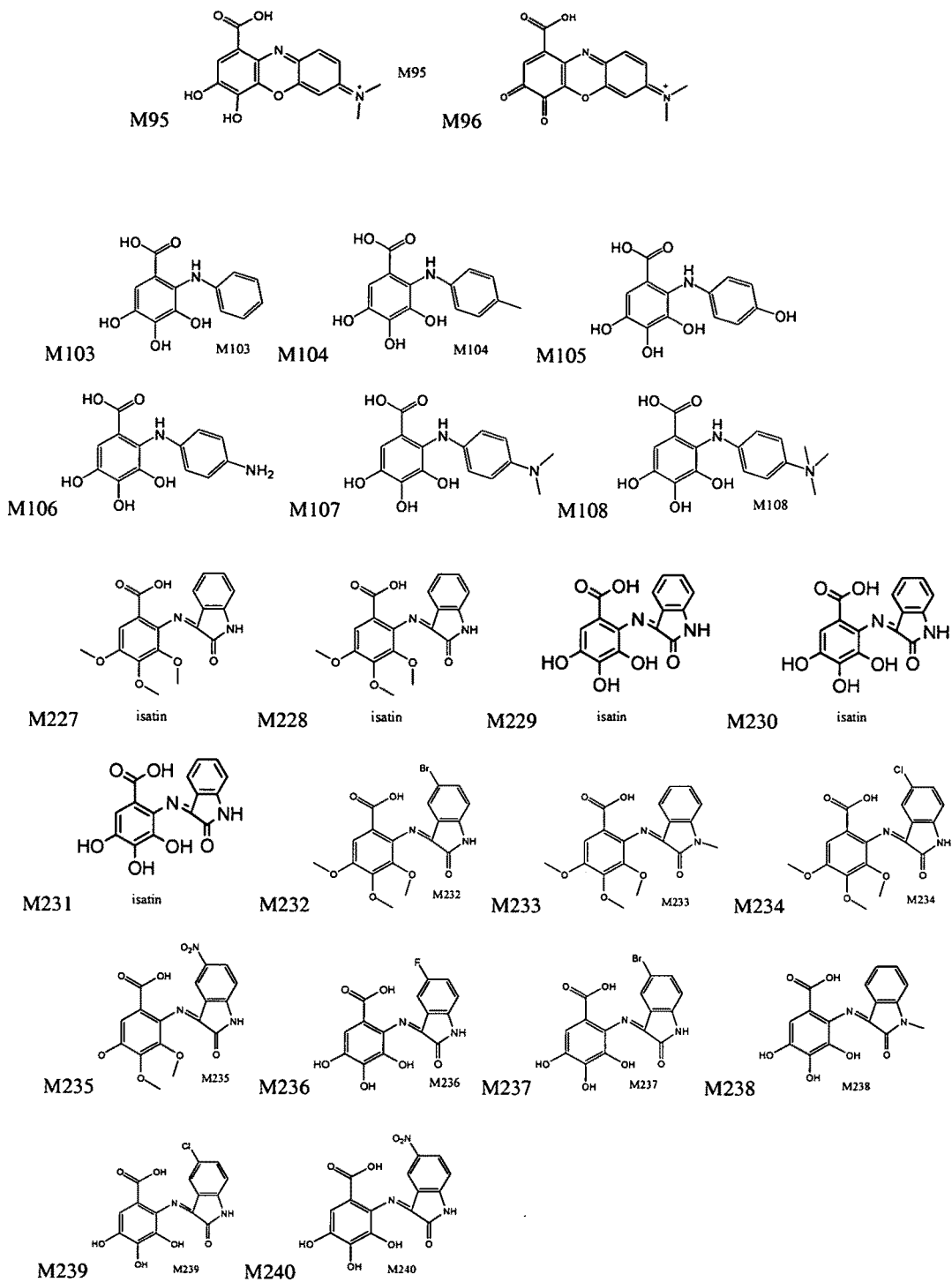
FIG. 6. Structures of M95, M96, M241, M242, M329, M330, M331, M103-108 and M227-240.

In this set, some members have $R_6$, $R_7$ and $R_8$ as hydroxyl groups and other members have $R_6$, $R_7$ and $R_8$ as methoxy groups; this set consists of compounds M227-M240 shown in FIG. 6.

Another series, M109-M114 are based upon substitution of S for O in the phenoxazine portion of molecules similar to Core Structure I of the '916 application—a set of compounds having the structure:

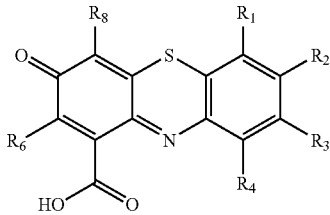

Variations in M109-M114 were made concerning the nature of the R2 and R3 groups, and their structures are shown in FIG. 1.

Another set of variants derived from Core Structure I include M241, M242, M329, M330 and M331 with the general structure depicted below:

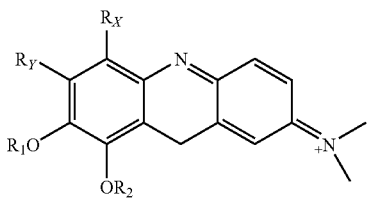

$R_X$ or $R_Y$ is a carboxyl group and $R_1$ and $R_2$ independently comprise a hydroxyl or methoxy group, as shown in FIG. 6.

Another series is based on Core Structure I of the '916 application as follows:

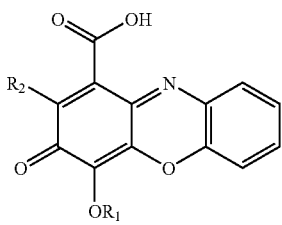

Figure 8:
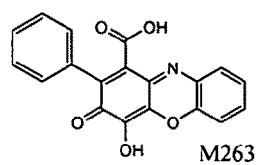
FIG. 8. Structures of M263-M280.
Figure 8:
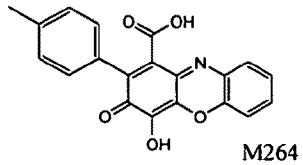
Figure 8:
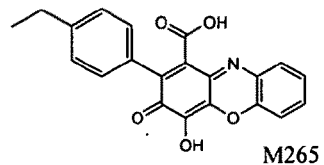
Figure 8:
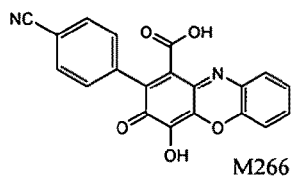
Figure 8:
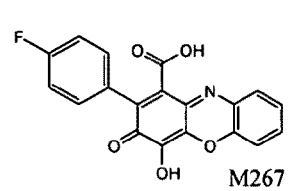
Figure 8:
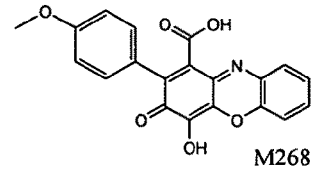
Figure 8:
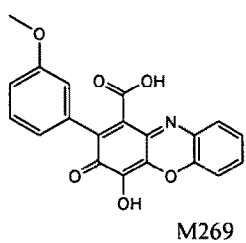
Figure 8:
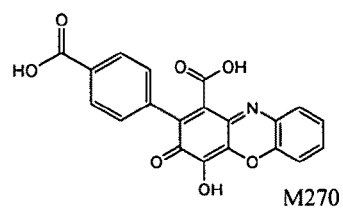
Figure 8:
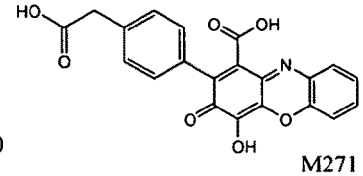
Figure 8:
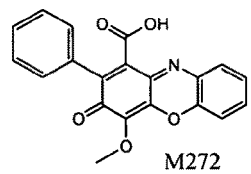
Figure 8:
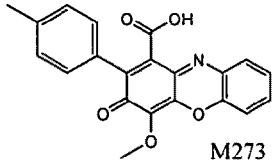
Figure 8:
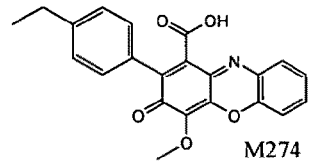
Figure 8:
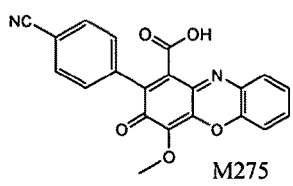
Figure 8:
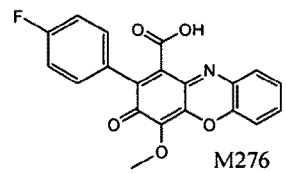
Figure 8:
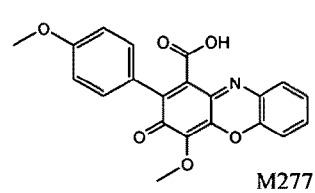
Figure 8:
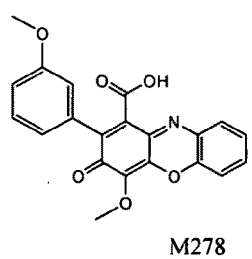
Figure 8:
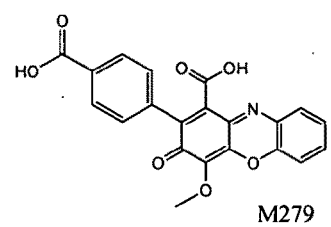
Figure 8:
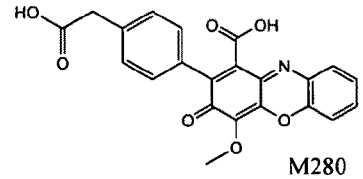

R1 comprises either a hydroxyl group or a methoxy group and R2 is a substituted or unsubstituted aromatic ring and this set is made up of compounds M263-M280, which are shown in FIG. 8.

Another group is based on the series above but with the addition of an amide group ($NR_3R_4$) with various substituents:

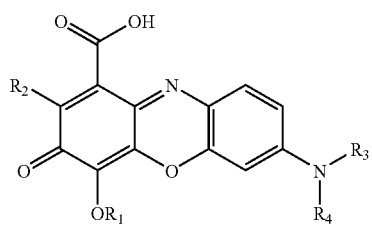

Figure 9:
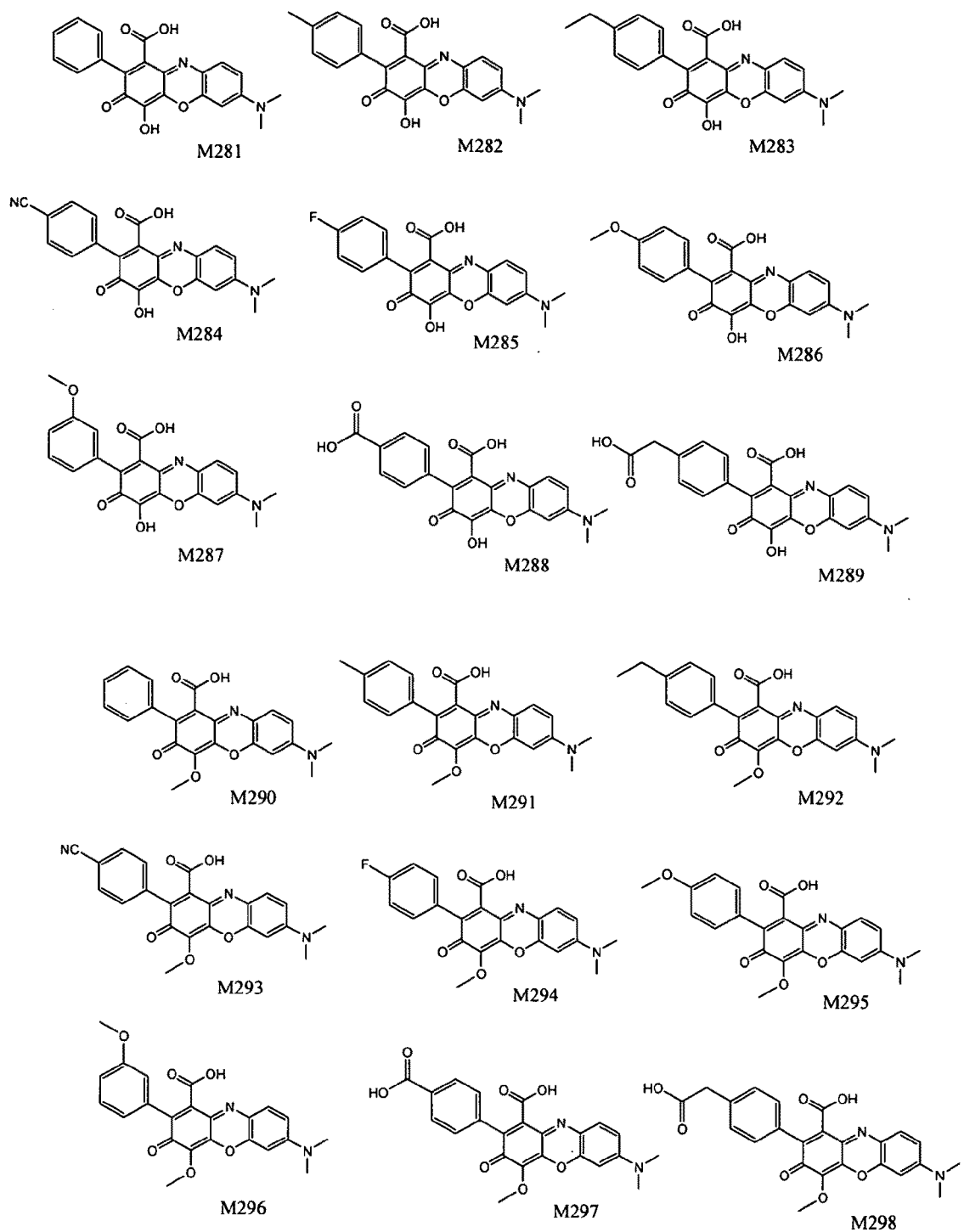
FIG. 9. Structures of M281-M298.
Figure 10:
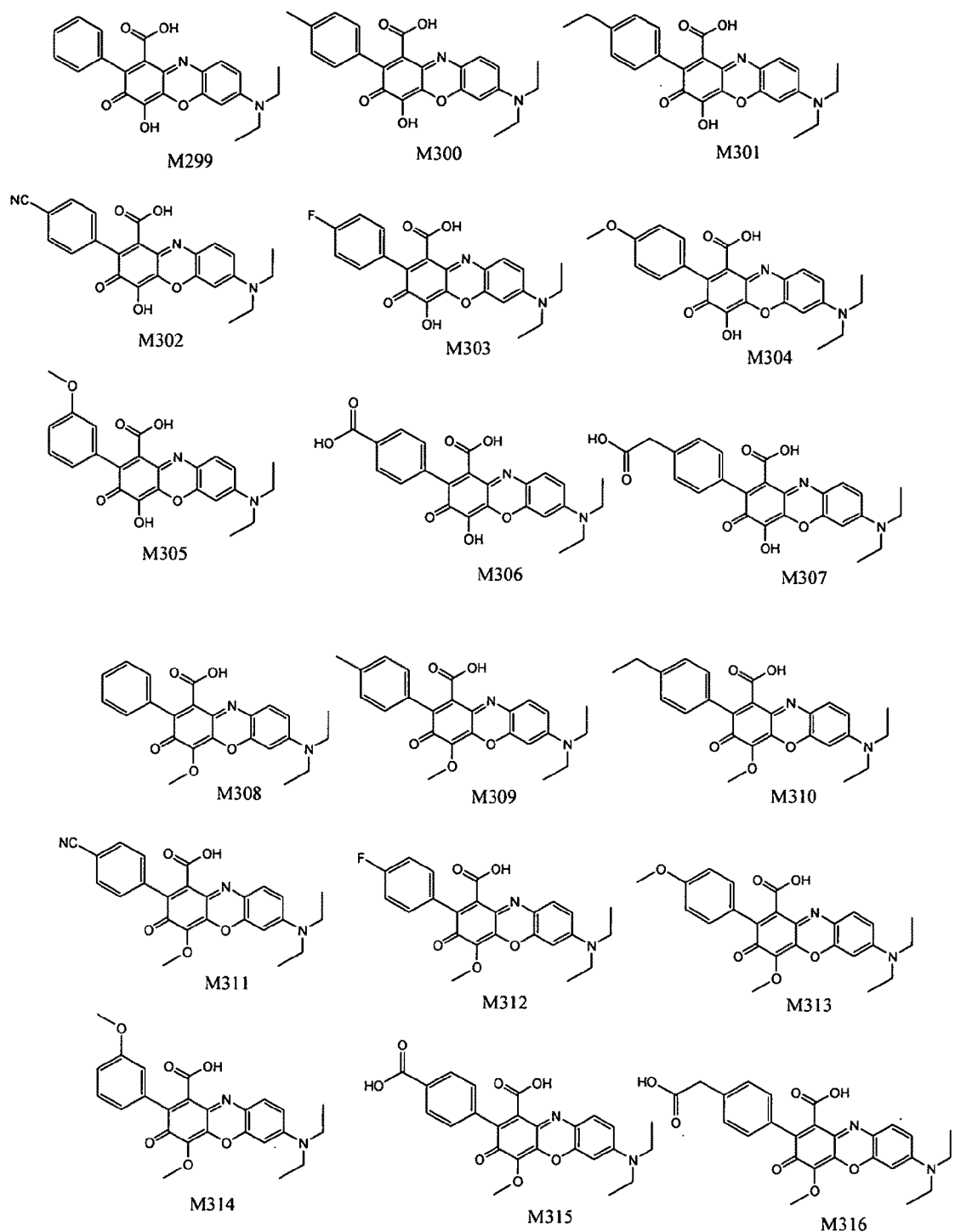
FIG. 10. Structures of M299-M316.

This group is made up of M281-316, as shown in FIGS. 9 and 10.

Another group of compounds is not based upon a phenoxazine or gallic acid template but is based upon an anthraquinone structure similar to compound IIC8 described in U.S. patent application Ser. No. 10/849,067, as follows:

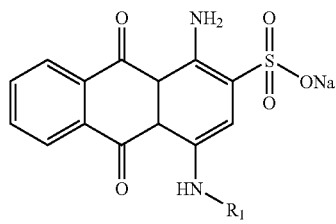

Figure 7:
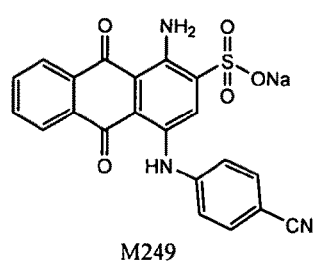
FIG. 7. Structures of M249-M262.
Figure 7:
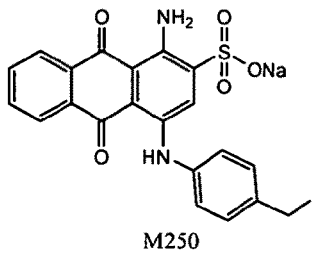
Figure 7:
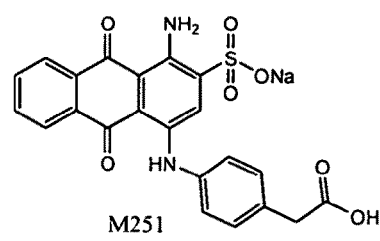
Figure 7:
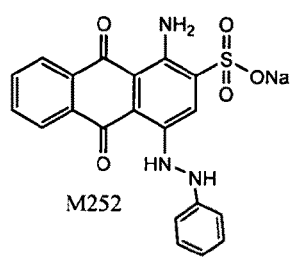
Figure 7:
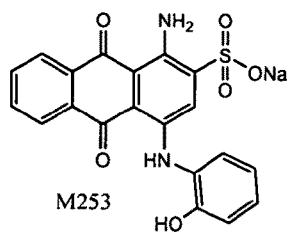
Figure 7:
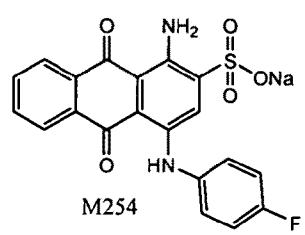
Figure 7:
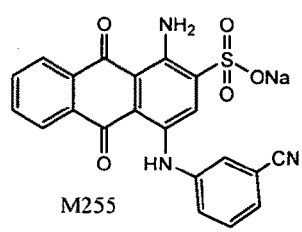
Figure 7:
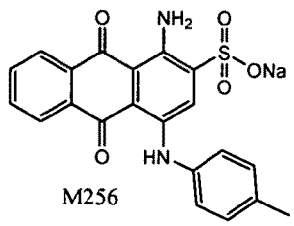
Figure 7:
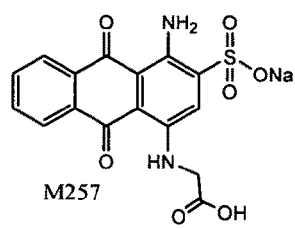
Figure 7:
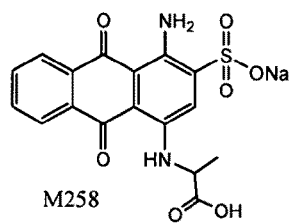
Figure 7:
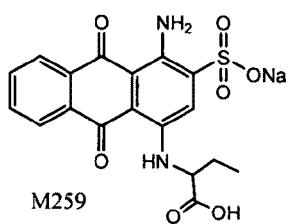
Figure 7:
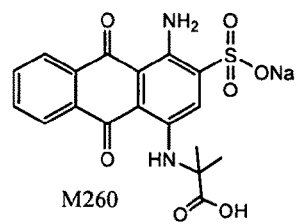
Figure 7:
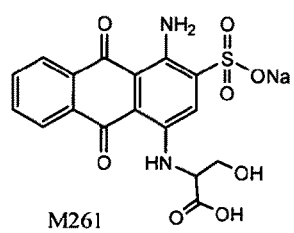
Figure 7:
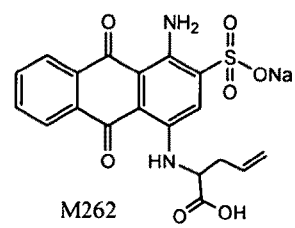
Figure 11:
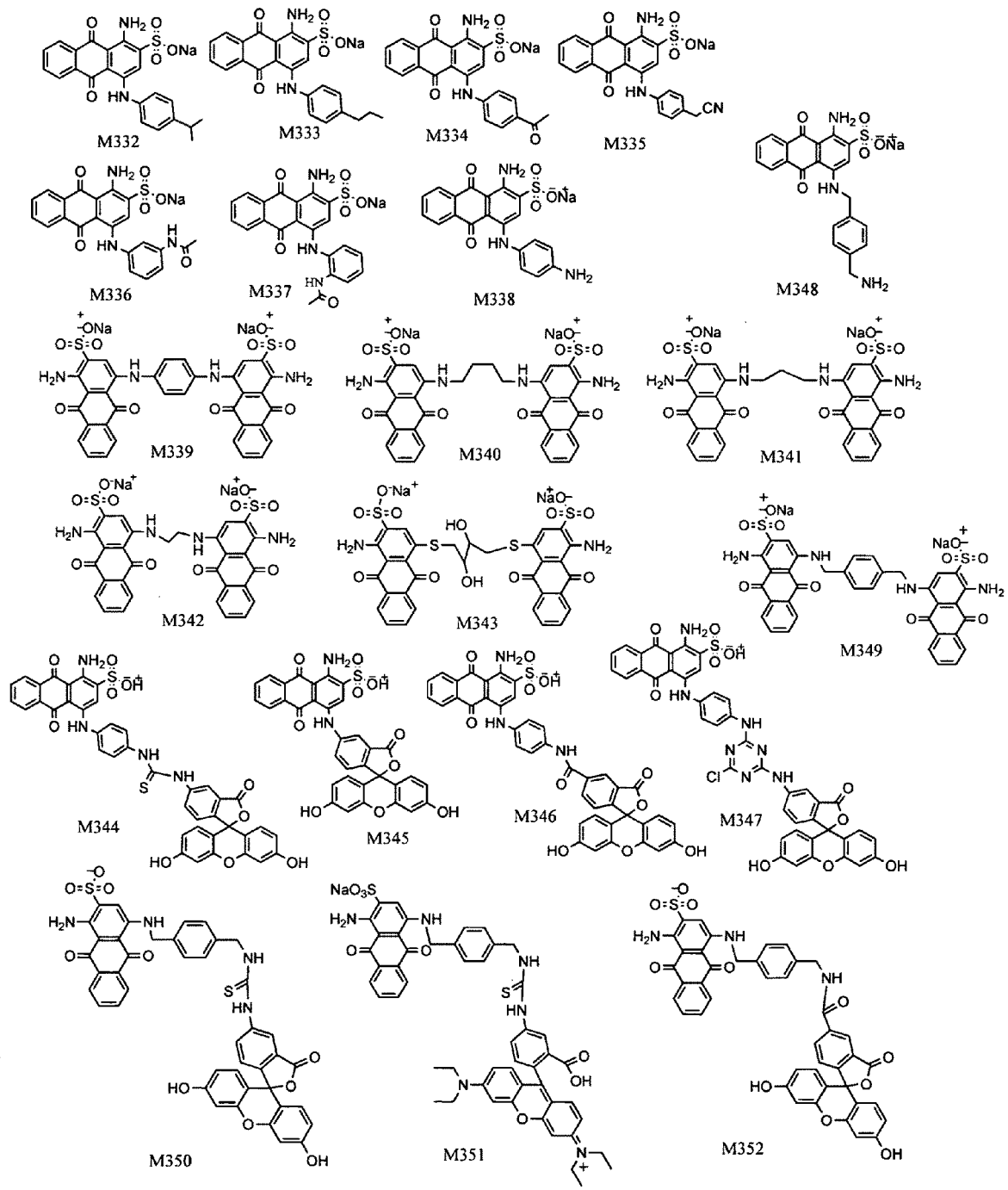
FIG. 11. Structures of M332-M352.

This set has various substituents for R1 in the structure above and these are designated as M249-M262, M332-M338 and M348, as shown in FIGS. 7 and 11.

As also disclosed in the previously cited '916 application as well as U.S. patent application Ser. No. 12/221,863 (filed Aug. 7, 2008) combinations of either the core compounds or subcores may also result in compounds that may have desirable properties. Accordingly, in one set, dimeric forms of the anthraquinone above were also designed:

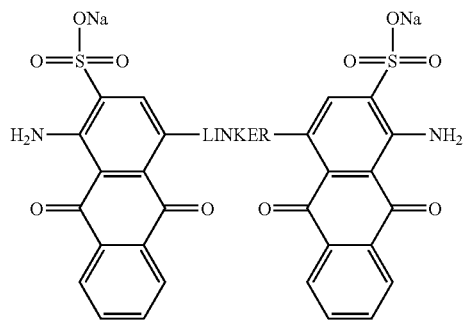

In this set a variety of different linkers were used to join the anthraquinone moieties together and this set includes compounds M339-M343 and M349, as shown in FIG. 11.

Another set of compounds are designed around an anthraquinone moiety joined to a xanthene derivative as shown for M344-M347 and M350-352, as seen in FIG. 11.

Figure 12:
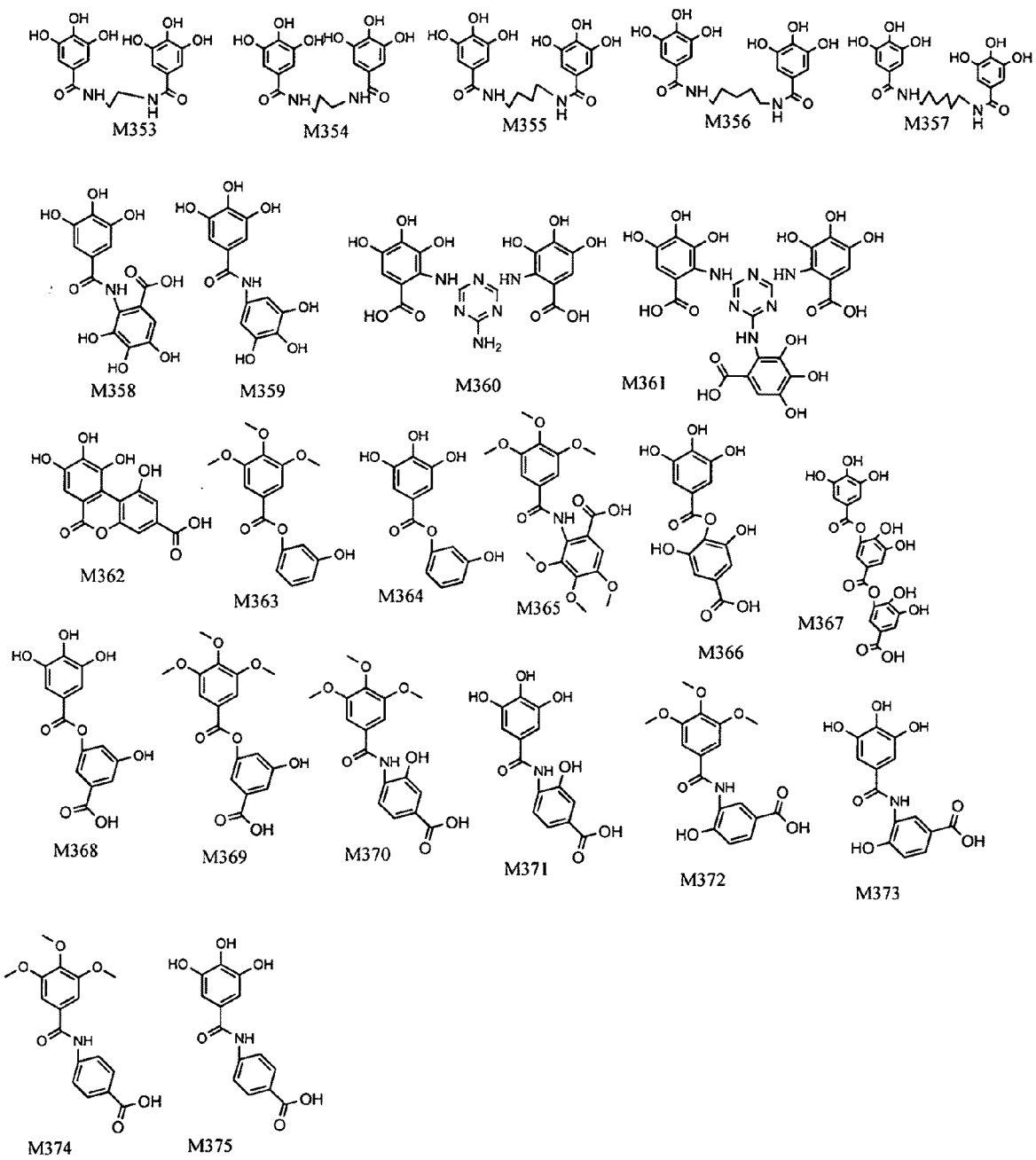
FIG. 12. Structures of M353-375.
Figure 13:
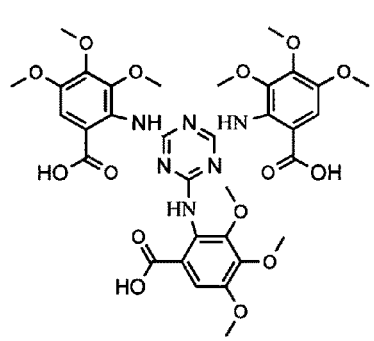
FIG. 13. Structures of M376-384.
Figure 13:
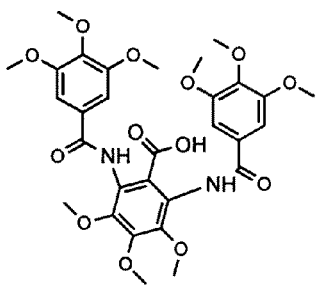
Figure 13:
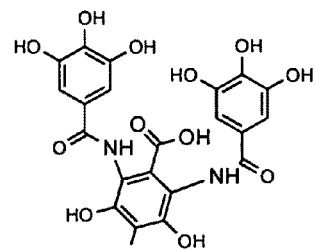
Figure 13:
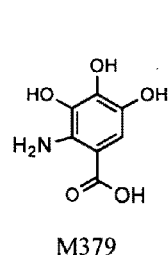
Figure 13:
Figure 13:
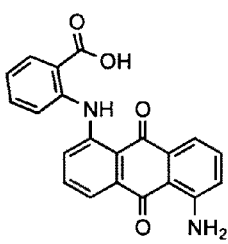
Figure 13:
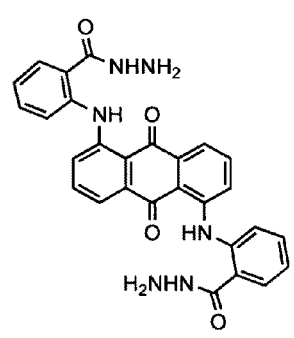
Figure 13:
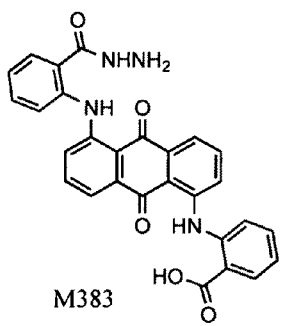
Figure 13:
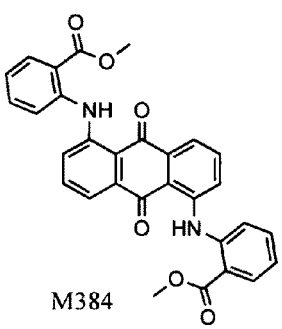

Another series of molecules were designed as a set of dimers and trimers of variously modified forms of gallic acid. This series includes compounds M353-M380, as shown in FIGS. 12 and 13.

The structures of the series of molecules described above were used in a virtual screening process to estimate effectiveness of their binding to Domain III of LRP5/6 by the methods disclosed in U.S. patent application Ser. No. 10/849,067. Compounds that had high binding scores were then synthesized and tested out in the Wnt assays described in this application. Additionally, the virtual screening process was also used to test a series of additional compounds from the NCI library and from a commercial library. The methods used to synthesize candidate compounds that later tested positively, as well as the results of the biological assays themselves, are described in the Examples section of the present patent application. The effects that were of interest at this stage of testing were effects on Wnt activity in the presence of these compounds and the influence of these compounds on the suppression of Wnt activity by Dkk.

The binding of a compound in and of itself does not predict the effects on the target protein. The compounds that are described in the Examples section demonstrate this effect where some compounds have been identified as Wnt inhibitors and others as Wnt stimulants. Furthermore some compounds showed no effects upon Wnt activity itself, but could block Wnt inhibition by Dkk molecules.

The process described above uses the discovery of effective compounds such as the previously described IC15 and IIIC3 to design analogues with variations at various sites which are replaced with selected substituents that may subsequently be tested by a virtual screening step, followed by biological assays. However, once effective compounds have been identified, analogues may also be tested empirically without going through further stages of virtual screening. The virtual screening step is only a method for enriching the pool of likely candidates and testing a small group of analogues of effective compounds may easily be carried out without the virtual screening step. In this connection, two compounds were directly tested in Examples 3-6, where each compound was a different analogue of IIIC3 (also referred to as NCI 8642 in the initial screening, and gallocyanine in the literature).

Figure 16:
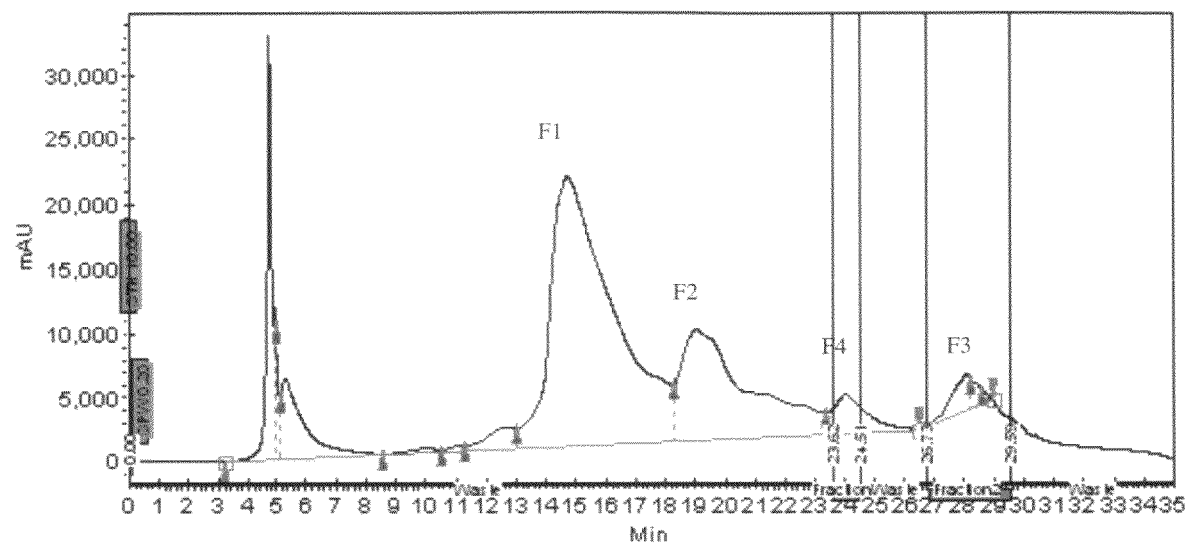
FIG. 16. HPLC profile of gallocyanine analogue preparation.
Figure 17:
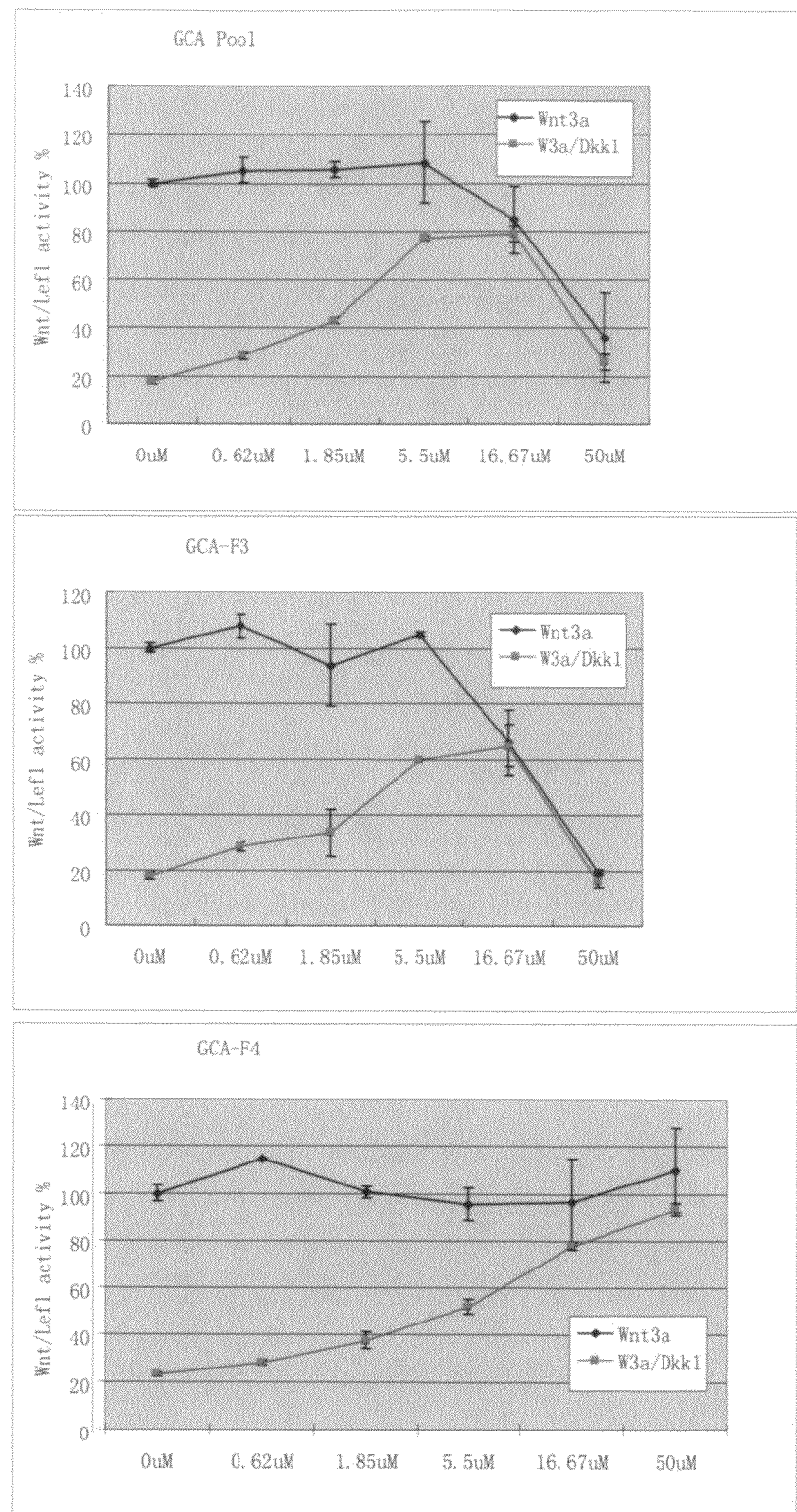
FIG. 17. Assay of effects of GCA fractions GCA-Pool, GCA-F3 and GCA-F4 on Wnt activity.
Figure 18:
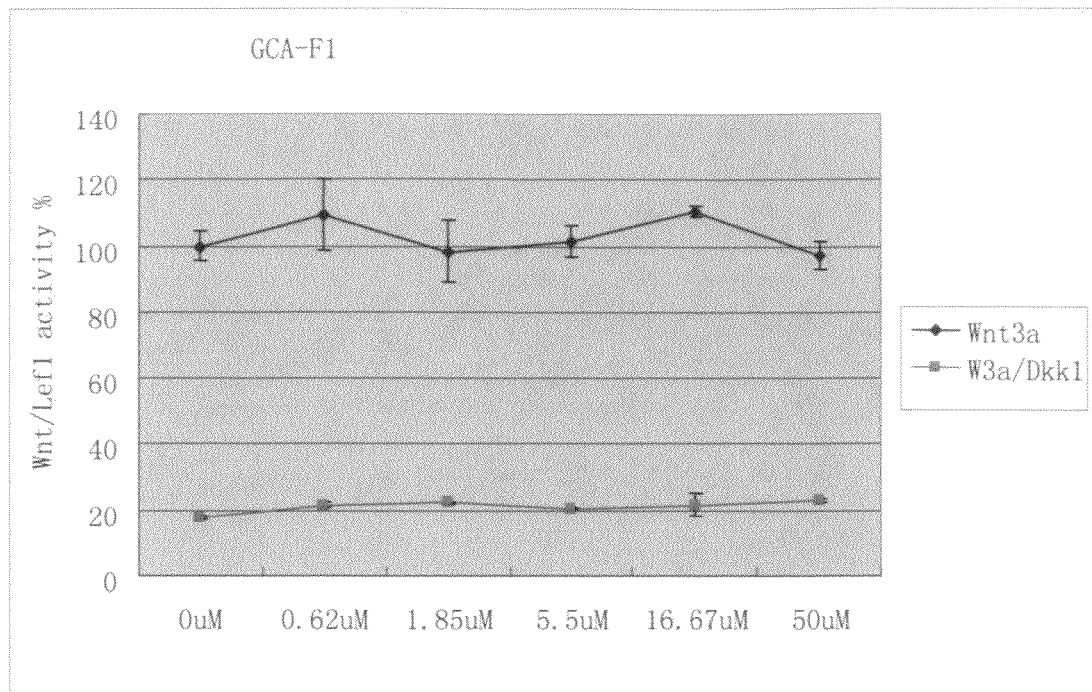
FIG. 18. Assay of effects of GCA fractions GCA-F1 and GCA-F2 on Wnt activity.
Figure 18:
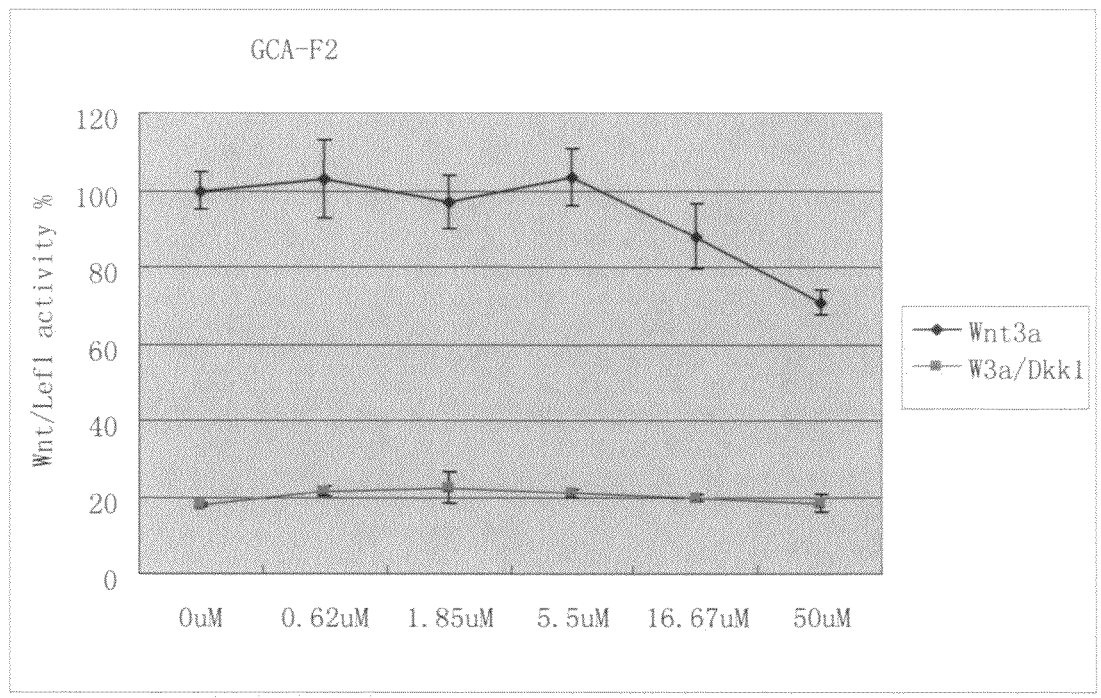

Analogues of gallocyanine were synthesized as described in Example 2 and tested with in vivo assays as described in Examples 3 and 4. Subsequent HPLC analysis demonstrated that the Gallocyanine Analogue (GCA) preparation actually separated out with at least four separate peaks, thus showing a multiplicity of compounds in this preparation. A preparative HPLC process was then carried out and the different species in the GCA mixture were individually collected as shown in FIG. 16 and described in Example 5. The individual properties of each of these species were found to be very different from each other as shown in the assay results in FIGS. 17 and 18 that were carried out as part of Example 6. It may be seen in FIG. 18 that the material from the GCA-F1 peak had no effect upon either Wnt activity or Dkk suppression of Wnt activity. Furthermore, the material from the GCA-F2 peak also had no effect on Dkk suppression and only showed effects on Wnt activity at higher concentrations (FIG. 18). Thus, although they may be derivatives of gallocyanine, the modifications GCA-F1 and GCA-F2 have resulted in a loss in the ability to affect Wnt activity. In contrast, both the GCA-F3 and GCA-F4 analogues showed substantial effects on Wnt activity, as seen in FIG. 17. With regard to Dkk suppression, GCA-F3 was able to block some of the effects of Dkk at low levels (0.62 μM and 1.85 μM) and a plateau is seen at 5.5 μM and 16.67 μM. In the absence of Dkk, no effects are seen on Wnt activity until 16.67 μM is reached where there is a decline in Wnt activity caused by the presence of GCA-F3. With 50 μM GC-F3, there is essentially no Wnt activity in either the presence or absence of Dkk. The profile of GCA-F4 is very different from that of the GCA-F3 analogue. In the absence of Dkk, Wnt activity remains constant even at the higher levels where GCA-F3 showed a marked inhibition of Wnt activity. This pattern is also seen in the presence of Dkk, where the inhibition of Dkk suppression continues at the higher levels (likely due to the continued presence of Wnt activity at these levels) such that at the highest level tested (50 μM) there is almost complete release from the effects of Dkk.

Figure 19:
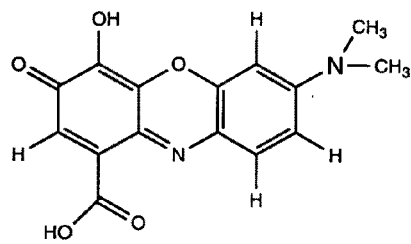
FIG. 19. Structures of gallocyanine analogues.
Figure 19:
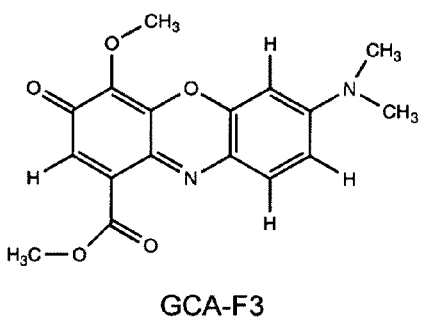
Figure 19:
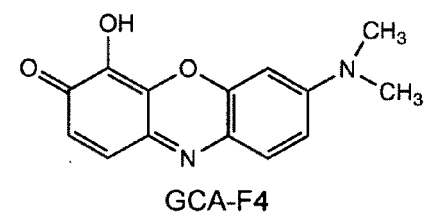
Figure 19:
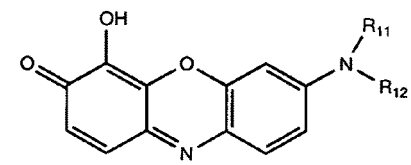
Figure 19:
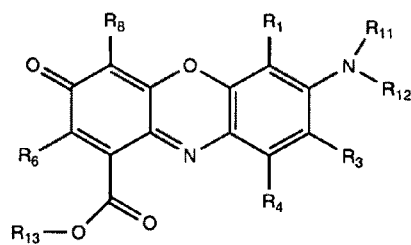
Figure 19:
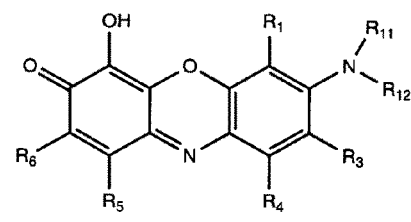

Structural determinations were carried out using NMR analysis for the active analogues of GCA-F3 and GCA-F4 and these are shown in FIG. 19. This Figure also shows a comparison of the Gallocyanine prototype as well as the core structure derived from it. As seen here, the GCA-F3 compound is a member of the compounds defined by Core Structure I in the '916 application, where $R_8$ is an O-methoxy group, $R_{11}$, $R_{12}$ and $R_{13}$ are methyl groups and the remaining R positions are hydrogens. On the other hand, the absence of a carboxyl group differentiates GCA-F4 from Gallocyanine itself. The discovery of the effectiveness of the GCA-F4 allows the establishment of new Core Structures that should allow the generation of other derivatives that may be useful in altering Wnt activity; these are shown below as Structure IX and Structure X, respectfully:

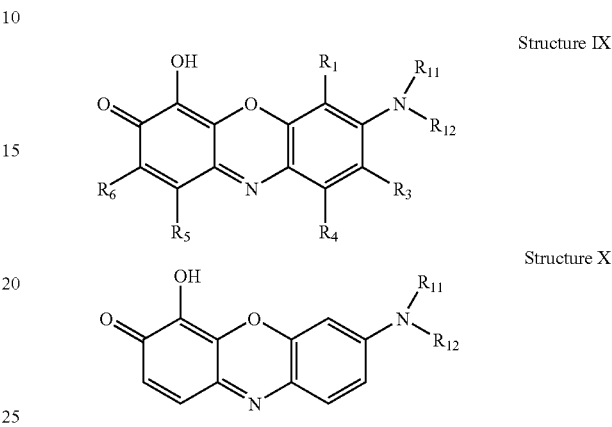

Structure IX

Structure X

At least one of $R^1$, $R^3$, $R^4$, $R^5$, $R^6$, $R^{11}$ or $R^{12}$ is a hydrogen atom and at least one of $R^1$, $R^3$, $R^4$, $R^5$, $R^6$, $R^{11}$ or $R^{12}$ comprises an atom other than a hydrogen atom. In a particular embodiment, $R^1$, $R^3$, $R^4$, $R^5$, $R^6$, $R^{11}$ or $R^{12}$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroararylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^{11}$, $R^{11}$ and $R^{12}$, $R^{12}$ and $R^3$, $R^3$ and $R^4$, $R^5$ and $R^6$ may independently be fused together to form one or more rings, or any combination of the foregoing. When the nitrogen of the amine group comprising $R^{11}$ and $R^{12}$ is charged (quarternized) and further comprises $R^{15}$, $R^{15}$ is as described previously for $R^1$, $R^3$, $R^4$, $R^5$, $R^6$, $R^{11}$ and $R^{12}$. In a particular embodiment, the compound has the Structure (X).

HPLC analysis has also shown the existence of a similar multiplicity of products with M358, M361, and M376 preparations, where the same process of separation of the individual peaks followed by characterization of the active compounds was carried out. A further complexity with regard to M361 is that the process used to synthesize this compound resulted in the presence of additional products that are unresolvable by HPLC (referred to as D and T forms (M358D & M358T, M361D & M361T, and M376 & M376T and discussed further in the Examples section). These forms were created at an early step and were continually present as each further step is carried out. As such, even after HPLC fractionation of the final product, biological assays carried out with these preparations are a result of two different (but similar) forms. Further understanding of the potential for these molecules was achieved by devising a different synthetic route where only the T forms were generated (See Example 12 for instance). Although there was still a necessity to carry out HPLC for separation into fractions, each peak collected represents only a single (T form) species.

The M series of compounds was a non-random library that was designed by using compounds identified in previous related applications and creating analogues with substitutions in various positions. Certain compounds of the M series that are described here are examples of compounds derived from core structures that had been previously described in related pending U.S. patent application Ser. No. 11/598,916. For instance, compounds M251, M333 and M335 are Core Structure III compounds that inhibit Wnt activity and compounds M338 and M339 are examples of Core Structure III compounds that stimulate Wnt activity. In addition, compound M358 fulfils the description of a Core Structure IV compound of the '916 application and GCA-F3 is an example of a Core Structure I compound.

In contrast, the "Enzo" series was a random library where compounds were selected strictly by virtual screening. However, certain candidates that were selected by virtual screening and showed effects upon Wnt activity could also be recognized as part of the core structure families of the '916 application. Thus, Enzo173 is a Core Structure IV compound, Enzo 558 is a Core Structure V compound and Enzo 517, Enzo 525, Enzo 527 and Enzo 539 are core structure III compounds. This is a further validation of the relationship of the core structures with effects on Wnt activity. The results of the "Enzo" series also permit the identification of a new family designated Core Structure XI, defined as:

Core Structure XI

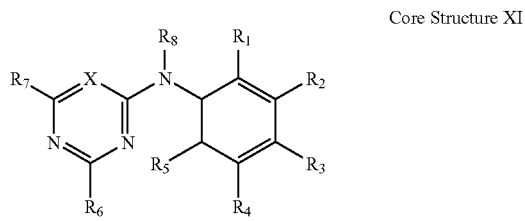

wherein X is N or C—$R^9$ and $R^1$, $R^2$, $R^3$, $R^4$, $R^5$, $R^6$, $R^7$ and $R^8$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroararylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^8$, $R^1$ and $R^2$, $R^2$ and $R^3$, $R^3$ and $R^4$, $R^4$ and $R^5$, may independently be fused together to form one or more rings, and when X=C—$R^9$, $R^7$ and $R^9$, and $R^9$ and $R^8$, may independently be fused together to form one or more rings or any combination of the foregoing. Examples of such compounds are Enzo188 and Enzo191 with X=N and Enzo192, Enzo195, Enzo198 and Enzo201 with X=C—$R^9$. M361 may be defined as a Core Structure XI compound, with X=N.

In related U.S. patent application Ser. No. 11/598,916, it was disclosed that the selection of a compound that binds to the YWTD derived β-propeller structure of LRP5/6 may also be a selection for a compound that binds to other YWTD derived β-propellers of the LRP family. Some of these may or may not be related to Wnt signaling. For instance, in the '916 application it was noted that both full length and truncated versions of LRP1 seemed to affect Wnt signaling (Zilberberg et al., 2004), but in the opposite fashion from LRP5/6 in that the truncated and intact LRP1 both seemed to repress Wnt signaling, possibly by acting as a competitive inhibitor via interaction with Fz-1. At the time, Zilberberg et al. also noted that the ability to interact with Frizzled may be shared by other members of the LRP family and predicted that they may also act as negative effectuators of Wnt signaling. However, it has been recently discovered that LRP1 may also stimulate Wnt activity (Terrand et al., 2009 JBC 284; 381-388) and that this Wnt signaling was involved in cholesterol metabolism. The differences between these studies may reflect differences in the components used. For instance, in the Zilberberg study, transfections were carried out using plasmids coding for Wnt-3a and Fz-1. In contrast, in the Terrand et al. study, Wnt5a was used and no exogenous Frizzled was added. Either of these factors may be significant, since experiments on myogenic differentiation induced by cholesterol depletion by Mermelstein et al. (2007 Differentiation 75; 184-192) have shown Fz-1 may inhibit Wnt activation and while Wnt3a induced myogenesis in this system, Wnt5a was inhibitory (Portilho et al., 2007 FEBS letters 581; 5787-5795) thereby demonstrating opposite effects between Wnt 3a and 5a in this system. Thus it should be understood that interaction of members of the LRP family with Wnt is not restricted to LRP5/6 alone and reinforces the concept that any molecule that binds to such proteins may potentially affect both Wnt as well as non-Wnt dependent processes. It also further reinforces the concept that when a compound is found to affect Wnt activity, a biological assay may provide further data concerning consequences of administration of a compound selected for LRP5/6 binding.

As such, although a Wnt dependent assay of β-catenin activity provides useful information for molecules that have been predicted to bind to the third YWTD domain of LRP5/6, such molecules may also be tested in other biological assays that measure activities that involve proteins with YWTD derived β-propeller structures. The structural conservatism of YWTD derived β-propeller structures in a number of different proteins creates a potential for binding to other proteins besides LRP5/6. Members of the LRP family (besides LRP5/6) that contain this particular YWTD derived β-propeller structure include LRP1/LRP1B, LRP2 (Megalin), LRP4 (MEGF7), LDLR, VLDLR, LRP8 (ApoER2) and LR11/sorLA-1. Non-LRP proteins that contain this motif include but are not limited to nidogen, osteonitogen, EGF precursor, and "sevenless". (For a review of the presence and arrangement of YWTD derived β-propeller structure in the foregoing proteins, see Springer 1998 J. Mol. Biol. 283; 837-862 and Strickland et al., 2002 Trends in Endocrinology & Metabolism 13; 66-74). Thus, any and all of the activities that these proteins are involved in may be suitable candidates for testing the effects of molecules selected for binding to a YWTD domain of LRP5/6.

In another embodiment, the success in using a model of YWTD repeats in a β-propeller structure in LRP5/6 to identify numerous compounds that bind to LRP5/6 in this as well as other related applications cited previously, allows the same process to be applied with high expectations of success to other amino acid sequences that form β-propellers from a series of YWTD repeats. Target candidates include members of the LRP family as well as other proteins that are not members of the LRP family. Since these sequences share a common structural motif, a virtual screening may be carried with a computer generated structure of the β-propeller containing the amino acids of the protein of interest for predictions of the ability of different compounds in a chemical library to bind to a selected β-propeller. As discussed above, this library may comprise a physical library of readily available compounds or it may comprise a virtual library of compounds that need to be synthesized at a later point. The compounds may be tested by a variety of methods. As mentioned previously in U.S. application Ser. No. 12/221,863, biological assays that are mechanism independent may be of utility. These may include glucose tolerization, insulin induction, wound healing, bone growth or inflammatory responses. Other assays may be used that utilize the particular functions that have been found to be associated with the targets of interest. It should be pointed out that even when the YWTD repeat is not directly involved in a particular function of the protein of interest, binding of a small molecule may induce allosteric shifts that will affect that function.

Another embodiment of the present invention involves identifying peptides that bind to proteins involved in the Wnt pathway that are involved in protein-protein interactions. In this method, a first member of a protein/protein pair may be immobilized to a solid matrix such as a bead or a plate and exposed to a phage library comprising various peptide sequences. After appropriate washing steps to eliminate non-specific binding of phage, the remaining bound phage can be released by a further washing step with either buffer, a soluble form of the first member or a soluble form of the second member of the protein/protein pair. For example, Sclerostin may be bound to a plate and after the binding of a phage library to Sclerostin and washing with a buffer, the mixture is collected. The phage in this mixture should be enriched for sequences that bind to the Sclerostin target and may be used to infect appropriate host bacteria. Clones may then be collected, followed by sequencing to identify the particular peptide sequences in the clone. Alternatively, the phage-containing supernatant from the Sclerostin plate can also be considered to be a first round and a further cycle enrichment can be carried out by using the first supernatant to create a second generation phage library that can again be used to bind to a Sclerostin plate followed by release, isolation and sequencing. The library that is used for such a binding selection process may be either a random library of peptide sequences or an ordered library representing fragments of key amino acids of the protein that is the binding partner of the protein immobilized to a matrix.

Peptide sequences that have been identified in this matter may be synthesized and tested in any of the assays described previously, including binding assays, Wnt-dependent reporter assays, growth assays, toxicity assays, expression array analysis, cytokine assays and metabolite measurements. In similar fashion to what has been discussed above, once a peptide sequence has been determined to be of interest, peptides can be made comprising amino acids analogues or peptide bond analogues.

In prior art, assaying for the effects of compounds on Wnt activity has entailed the transfection of constructs that express various members of the Wnt signaling system to allow the generation of a maximal signal. Although success has been achieved by these means (as witnessed by data presented in the present invention as well as in related patents cited and discussed above), the method intrinsically involves a complex methodology that requires a high level of technical skill, and suffers from problems of consistency and reproducibility. It is because of these problems that in general, transfection based assays are usually accompanied by controls such as lacZ or GFP to monitor transfection efficiency/success. As such, it is another aim of the present invention to disclose methods that may eliminate such a step by generating cell lines that allow the stable expression of Wnt signal reporters that may be used for quantitative assessments of Wnt activity. Previous art has disclosed the production of cell lines that involve individual members of the Wnt signaling pathway for research on the roles that these proteins play. Examples of such stable transformants include Wnt (Ryu and Chun 2006 J. Biol. Chem. 281; 22,039-22,047); LRP6 (Li et al., 2004 Oncogene 23; 9129-9135) and LEF-1 (Kim and Hay 2001 Cell Biology International 25; 1149-1161). Artificial constructs for reporter genes responding to Wnt signals have been used for generating transgenic mice expressing the TOPGAL (LEF dependent β-galactosidase) gene (DasGupta and Fuchs 1999 Development 126; 4557-4568), as well as cell lines expressing a TCF dependent luciferase reporter construct (Binnerts et al., 2007 Proc. Nat. Acad. Sci. (USA) 104; 14,700-14,705) and a dual system involving both LEF-1 and LEF dependent Green Fluorescent Protein (GFP) constructs (Grueneberg et al., 2003 Mol Cell Biol 23; 3936-3950). The latter cell line is useful for in vivo studies as well as in situ experiments but is relegated to a presence/absence type of signal generation due to the nature of the GFP marker.

The present invention discloses the generation and use of a stable line that expresses LEF-1 and a LEF-1 reporter gene that can be quantified by bioluminescence. The LEF-1 constructs described by Behrens et al., 1996 Nature 382 638-642, Huber et al., 1996 Mech Develop 59; 3-10, Kim and Hay (2001), Gruenberg et al., (2003) or similar such constructs may be used for this purpose for stable expression of LEF-1. LEF-1 may also be substituted by TCF1, TCF3 or TCF 4, each of which recognizes the same DNA consensus motif as LEF-1. As such, they are considered to be functional equivalents of LEF-1 in the present invention (for a review, see Eastman and Groschedl 1999 Current Opinion in Cell Biol 11; 233-240). Any of the TCF/LEF dependent bioluminescent constructs that have been described in the literature for expression may be used for providing quantitative readouts for stable expression in the present invention. Examples of luciferase reporter constructs include the TOPFLASH luciferase gene (Korinek et al. 1997 Science 275; 1784-1787) as well as the construct described by Binnerts et al., (op. cit.).

Since the continuous expression of a major control element such as LEF-1 may be deleterious, the cell lines may be designed to allow conditional expression of the LEF-1 gene. Numerous examples of methods for conditional expression are described in the literature. Two commonly used methods are the Tet-On or Tet-Off systems. In the Tet-On system, the binding of the rtTA version of the Tet transactivator activates expression from a TRE vector in the presence of deoxycycline (Dox) whereas in the Tet-Off expression system, the binding of a different version of the transactivator, tTA, allows expression only in the absence of Dox (Gossen and Bujard 1992, Proc. Nat. Acad. Sci. USA 89; 5547-5551, Gossen et al., 1995 Science 268; 1766-1769). As such, this system would also entail the introduction of an additional construct into the cell line for expression of the appropriate transactivator.

The creation of a cell line of the present invention may be carried out with a series of steps for the introduction and testing of each nucleic acid construct, or there may be cotransfection with more than one. In a similar way, the nucleic acid constructs may include a selectable marker in addition to the LEF-1, LEF/TCF dependent reporter or transactivator sequence. In contrast, cotransfection with a selectable marker on a separate nucleic acid construct may also be employed. Examples of selectable markers for eukaryotic cell lines are well known in the art and representative genes may comprise but not be limited to the expression of proteins coding for resistance to zeomycin, puromycin, neomycin, hygromycin, histidinol, mycophenolic acid, ouabain, or blasticidin S.

Once a stable cell line of this nature is created, it may be used for a variety of purposes including the testing of compounds for an ability to affect Wnt activity. Thus, for example, a cell line may be tested with various concentrations of a compound of interest in the presence, and absence, of Wnt and the bioluminescent measurements may be used for assessing the effects of the compound. Other factors may be added as well, such as a Wnt stimulator and/or a Wnt inhibitor. A number of such entities have been described in the Background of the Invention as well as in other embodiments of the present invention. The stable cell line may also offer opportunities to test the effect of mutations on various elements of the Wnt system by transfecting constructs coding for mutant proteins into the cell line. Similar cell lines may also be created from cells that have mutations in elements of the Wnt pathway, such as point mutations or deletions, as well as homozygous or heterozygous knockout mice that are lacking or have reduced LRP5, LRP6, Dkk or Kremen activity.

The present invention offers a quicker, more reliable method of assessing the effects on the Wnt pathway compared to previous methods that required individual transfections of nucleic acids for each experiment. The cell line should also allow comparisons to be made from experiment to experiment, whereas previously only internal comparisons could be made with traditional transient expression experiments.

The majority of the medical applications mentioned have apparent benefits to increasing Wnt activity. The present family of related patent applications have demonstrated that compounds that block Dkk directed inhibition of Wnt may be used for treatment of diseases associated with bone and metabolic functions. Similarly, Applicants have also previously demonstrated effects on metabolism in Dkk knockout mice, once again showing that the loss of Dkk functionality (and conversely an increase in Wnt activity) may be beneficial. Blocking Dkk inhibition of Wnt, or the direct stimulation of Wnt activity may have applications in the treatment of neurodegenerative diseases as well. For instance, it is known that the induction of Dkk1 (and therefore a decrease in Wnt activity) has been associated with the neuronal degeneration associated with development of Alzheimer's Disease (Caricasole et al; 2004, J Neuurosci 24; 6021-6027, Caraci 2008 Neurochem Res 33; 2401-2406) and accordingly, that the activation of Wnt may provide benefits for this disease (Caricasole et al., 2003 Trends in Pharmacologica Science 24; 233-238, Inestrosa and Toledo 2008 Molec. Degen 3: 9). Accordingly, either compounds that activate Wnt or that block inhibition by Dkk may be used for this purpose. Another recent finding is that the activation of Wnt signaling inhibits the replication of HIV (Kumar et al., 2008 J Virol 82; 2813-2820), suggesting that Wnt activating compounds may also find use in the treatment of viral infections as well.

However, there may be instances where beneficial results may be obtained by decreasing Wnt activity instead. For example, tremendous effort has been directed to methods of decreasing Wnt activity in order to provide treatment for cancer. As discussed in related U.S. patent application Ser. No. 11/598,916, the connection between Wnt activity and cancer is a complex issue, where for instance, Wnt5A has been shown to act as a tumor suppressor in hematopoietic cells (Liang et al, 2003 Cancer Cells 1:279-288) while promoting motility and invasiveness in melanomas (Weeraratna et al., 2002 Cancer Cell 1: 279-288). For reviews on the inter-relationship between the Wnt pathway and tumorogenesis as well as tumor maintenance, see Polakis 2000, Genes Dev 14; 1837-1851, Behrans and Lustig 2004 Int J Dev Biol 48; 477-487; Luu et al., 2004 Curr Cancer Drug Targets 4; 653-671; Bafico et al., 2004 Cancer Cell 6; 497-506, Rubins et al., 2006 Frontiers in Bioscience 11; 2093-2105 and Janssens et al., 2006 Investigational New Drugs 24; 263-280.

The paradoxical relationship between Wnt activity and cancer may also be seen in papers describing attempts to actively intervene cancer through reagents that modify Wnt activity where a factor that blocks Wnt activity, sFRP1, reduced proliferation and survival of breast cancer cells (Schlange et al., 2007 Breast Cancer Res 9; R63) and yet a compound, QS11, that enhances Wnt activity has been shown to decrease the invasiveness of breast cancer cells. (Zhang 2007 Proc. Nat. Acad. Sci. USA 104: 7444-7448). As such, although the major activity in the cancer research field has been a search for compounds that may inhibit Wnt activity, compounds that increase Wnt activity may find use in the treatment of cancers as well. In addition to cancer, it has also been recently discovered that increased Wnt activity was associated with accelerated cellular senescence (Liu et al., 2007 Science 317: 803-806), suggesting another potential useful role of Wnt inhibitors in the treatment of age-related diseases.

COMPOSITIONS

The compound(s) disclosed in the present invention may be formulated into a composition, most notably a pharmaceutical composition. Such a composition typically contains from about 0.1 to 90% by weight of a metabolic intermediate of the invention formulated in and/or with a pharmaceutically acceptable carrier or excipient. Pharmaceutical formulation is a well-established art, and is further described in Gennaro (ed.), Remington: The Science and Practice of Pharmacy, 20th ed., Lippincott, Williams & Wilkins (2000); Ansel et al., Pharmaceutical Dosage Forms and Drug Delivery Systems, 7th ed., Lippincott Williams & Wilkins (1999); and Kibbe (ed.), Handbook of Pharmaceutical Excipients American Pharmaceutical Association, 3rd ed. (2000).

Briefly, formulation of the pharmaceutical compositions of the present invention will depend upon the route chosen for administration. The pharmaceutical compositions utilized in this invention may be administered by various routes including both enteral and parenteral routes, including oral, intravenous, intramuscular, subcutaneous, inhalation, intrathecal, intraventricular, transmucosal, transdermal, intranasal, intraperitoneal, and intrapulmonary. The pharmaceutical composition may comprise one or more agents of the present invention.

Oral dosage forms may be formulated as tablets, pills, dragees, capsules, liquids, gels, syrups, slurries, suspensions, and the like, for ingestion by the patient. Solid formulations of the compositions for oral administration may contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid. Agents that facilitate disintegration and/or solubilization may be added, such as the cross-linked polyvinyl pyrrolidone, agar, alginic acid, or a salt thereof, such as sodium alginate, microcrystalline cellulose, corn starch, sodium starch glycolate, and alginic acid. Tablet binders that may be used include acacia, methylcellulose, carboxymethylcellulose, polyvinylpyrrolidone (Povidon™) hydroxypropyl methylcellulose, sucrose, starch and ethylcellulose. Lubricants that may be used include magnesium stearates, stearic acid, silicone fluid, talc, waxes, oils, and colloidal silica. Fillers, agents that facilitate disintegration and/or solubilization, tablet binders and lubricants, including the aforementioned, may be used singly or in combination. Solid oral dosage forms need not be uniform throughout. For example, dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention also may include push-fit capsules made of gelatin, as well as soft, sealed capsules made of gelatin and a coating, such as glycerol or sorbitol. Push-fit capsules may contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Additionally, dyestuffs or pigments may be added to the tablets or dragee coatings for product identification or to characterize the quantity of active compound, i.e., dosage.

Liquid formulations of the pharmaceutical compositions for oral (enteral) administration are prepared in water or other aqueous vehicles and may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

The pharmaceutical compositions of the present invention may also be formulated for parenteral administration. Formulations for parenteral administration may be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, may be dissolved and administered in a pharmaceutical excipient such as Water-for-Injection, 0.9% saline, or 5% glucose solution. Alternatively, a suitable insoluble form of the compound may be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions may also contain substances that increase the viscosity of the suspension, such as sodium carboxymethyl cellulose, sorbitol, or dextran. Non-lipid polycationic amino polymers may also be used for delivery. Optionally, the suspension may also contain suitable stabilizers or agents that increase the solubility of the compounds to allow for the preparation of highly concentrated solutions.

Pharmaceutical compositions of the present invention may also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release may be controlled. Examples of other biodegradable polymers include poly(orthoesters) and poly(anhydrides). Depot injectable formulations are also prepared by entrapping the drug in microemulsions that are compatible with body tissues.

Inhalation formulations may also readily be formulated. For inhalation, various powder and liquid formulations may be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention may be in powder form for reconstitution in the appropriate pharmaceutically acceptable carrier at the time of delivery.

The pharmaceutically active compound in the pharmaceutical compositions of the present invention may be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

The therapeutically effective dose of the compound(s) used in the present invention may be estimated initially by in vitro tests, such as cell culture assays, followed by assays in model animals, usually mice, rats, rabbits, dogs, or pigs. The animal model may also be used to determine an initial preferred concentration range and route of administration. For example, the $ED_{50}$ (the dose therapeutically effective in 50% of the population) and $LD_{50}$ (the dose lethal to 50% of the population) may be determined in one or more cell culture of animal model systems. The dose ratio of toxic to therapeutic effects is the therapeutic index, which may be expressed as $LD_{50}/ED_{50}$. Pharmaceutical compositions that exhibit large therapeutic indices are preferred.

The data obtained from cell culture assays and animal studies are used in formulating an initial dosage range for human use, and preferably provide a range of circulating concentrations that includes the $ED_{50}$ with little or no toxicity. After administration, or between successive administrations, the circulating concentration of active agent varies within this range depending upon pharmacokinetic factors well known in the art, such as the dosage form employed, sensitivity of the patient, and the route of administration.

The exact dosage will be determined by the practitioner, in light of factors specific to the subject requiring treatment. Factors that may be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. In a particular embodiment, the daily dosage is about 0.01 mg to 30 mg/kg of body weight of the patient (e.g., 1 mg/kg to 5 mg/kg). The pharmaceutical formulation may be administered in multiple doses per day, if desired, to achieve the total desired daily dose.

Conventional methods, known to those of ordinary skill in the art of medicine, may be used to administer the pharmaceutical formulation(s) of the present invention to the patient. The pharmaceutical compositions of the present invention may be administered alone, or in combination with other therapeutic agents or interventions. Specifically, the compositions of the present invention may further comprise a plurality of agents of the present invention. The treatment of a disease in any of the described methods results in a change in the number or function of regulatory, immune-regulatory or NKT cells. This change encompasses a reduction, inhibition, or decrease in the number or function of the cells. This inhibition may be caused by the competitive displacement of activating elements from the CD1d molecule. A change may also include a stimulation or increase in the number or function of the cells. This stimulation may be caused by increased binding of the activating elements from the CD1d molecule.

The present invention is directed towards the identification and use of compounds that affect the Wnt signal system. As such, any physiological process that involves elements of the Wnt signal system may find use with the present invention. Accordingly, administration of the compounds of the present invention may be effective in the treatment of a variety of diseases including bone fractures, bone disease, bone injury, bone abnormality, tumors, growths or viral infections as well as for modulating pathophysiological processes including but not limited to glucose metabolism, lipid metabolism, triglyceride metabolism, adipogenesis, tumorigenesis, neurogenesis and bone-related activity. For a review of diseases related to Wnt, see Moon et al., 2004 Nature Rev. Genet. 5; 691-701, Manolagas and Almeida 2005 Molec. Endrocrin. 21; 2605-2614, Johnson and Rajamannan, 2006 Rev. Endocr. Metab. Disord. 7; 41-49, Maiese et al., 2008 Pharmacology & Therapeutics 118; 58-81).

EXAMPLE 1

Virtual Screening

The designs of the various compounds that comprise a virtual library are shown in FIGS. 1-13 and are designated as compounds M71-M364. Another series of compounds were derived from the NCI database/chemical library as well as commercial database/chemical libraries from ChemDiv, Inc. (San Diego, Calif.), Chembridge Corporation (San Diego, Calif.) and Life Chemicals USA (Orange, Conn.). This series is referred to as Enzo001-Enzo438. Compounds derived from the M71-M364 series are novel compounds of a virtual library that require synthesis before testing in a biological assay. On the other hand, the Enzo001-Enzo438 series represents a physical library—a series of compounds that have already been synthesized and are readily available for testing. These compounds were screened as described previously in related pending U.S. patent application Ser. No. 10/849,067 and candidates were selected on the basis of a predicted binding to Domain III of LRP5/6.

Although a combination of UNITY™ and FlexX™ were used as a docking program in the virtual screening of this process, other similar programs are available and may be used if so desired. Examples of such programs include, but are not limited to DOCK, SANDOCK, FlexiDock, ICM, EUDOC, GOLD, LUDL CATALYST and PRO_LEADS. Similarly, although CScore was used as a scoring program for ordering the results, other similar programs are also available. These may include, but are not limited to ChemScore, AMBER, OPLS and CHARMM.

EXAMPLE 2

Synthesis of Gallocyanine Analogues

One compound that has been of interest in the related patent applications is IIIC3, otherwise known as Gallocyanine and NCI 8642. A number of the compounds described in Example 1 are analogues of this compound and as described above, underwent a virtual screening step to select the best candidates. However, as mentioned in the text, analogues of compounds that show effectiveness may also be tested in the absence of such a screening step. Thus, a synthesis was carried out that produced at least two different IIIC3 analogues that were tested directly without the screening step. In this process, a mixture of 100 mg (0.33 mMoles) of gallocyanine (chloride free), 50 ml of methanol, 38 µl (0.33 mMoles) of 2,6-lutidine and propyliodide (0.5 ml) were placed in a 150 ml pressure vessel with a stirrer. The mixture was stirred and heated at approximately 110° C. for 4 days. After concentration in vacuo, the residue was washed with 5 ml of ethanol. Solid products were recovered by filtration. When tested, biological assays of this preparation showed significant activities on Wnt activities (data shown and discussed in Example 6). Additional batches of this preparation were made with this procedure and used in various experiments.

EXAMPLE 3

Effects of Gallocyanine Analogues on Mice Placed on a High Caloric Diet

Figure 14:
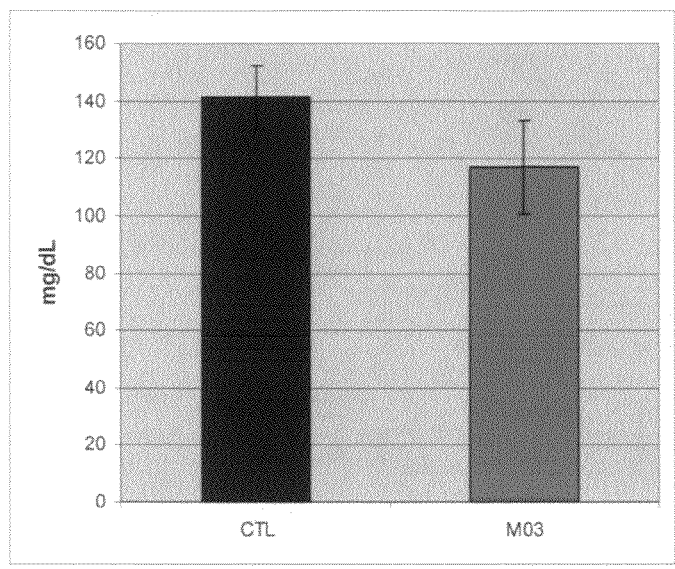
FIG. 14. Effects of gallocyanine analogues on blood glucose with mice placed on high caloric diet.
Figure 14:
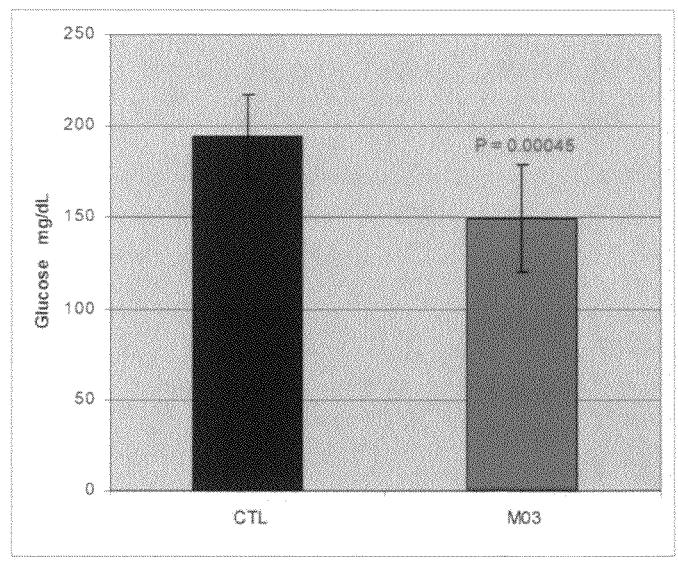

This experiment was carried out essentially as described previously with IC15, IIIC3 and M01 in related pending U.S. patent application Ser. No. 11/598,916 with the exception of using the gallocyanine analogue preparation from Example 2 above. 8 week old C57/BL6J mice were placed on a high fat diet for 60 days and then treated on a daily basis starting at day 50 with the M03 preparation from Example 2 (1 mg/kg/day) either by intraperitoneal injection or by oral gavage. On day 60, blood glucose levels were measured after overnight fasting. As shown in FIG. 14, with intraperitoneal administration, the control mice (N=15) had an average of 141.2 mg/dL of glucose while the mice (N=10) treated with the preparation from Example 2 had an average level of 116.8 g/dL. After administration by oral gavage, a similar effect was seen in the treated mice compared to the controls.

EXAMPLE 4

Effects of Gallocyanine Analogues from Example 2 on Db/Db Mice

This experiment was carried out as previously described with IIIC3 in related U.S. patent application Ser. No. 11/598,916, using the preparation from Example 2 above as the test compound. The db/db mice served as a model for diabetes and were used to test the effectiveness of the preparation made in Example 2. These mice are similar to the ob/ob mice described previously in the '916 application, with the exception that the ob/ob mice used in the '916 application were missing leptin while the db/db mice used in this example were missing the leptin receptor.

Figure 15:
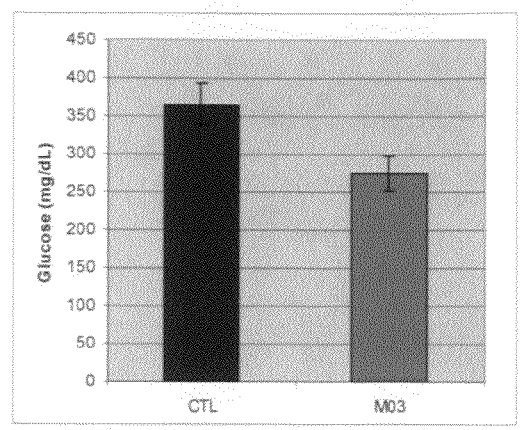
FIG. 15. Effects of gallocyanine analogues on db/db mice.
Figure 15:
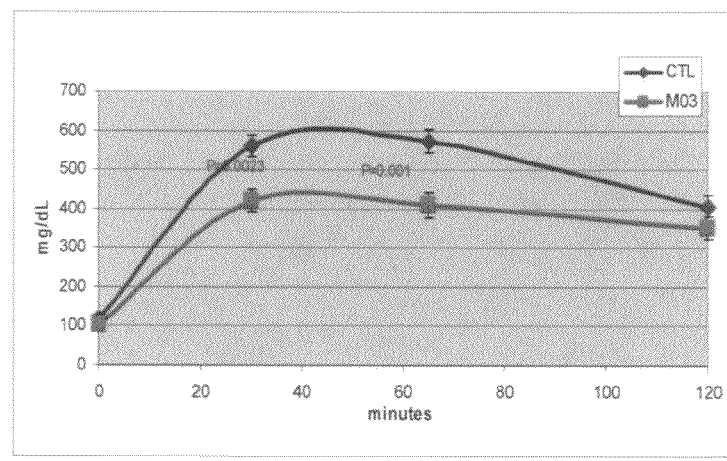
Figure 15:
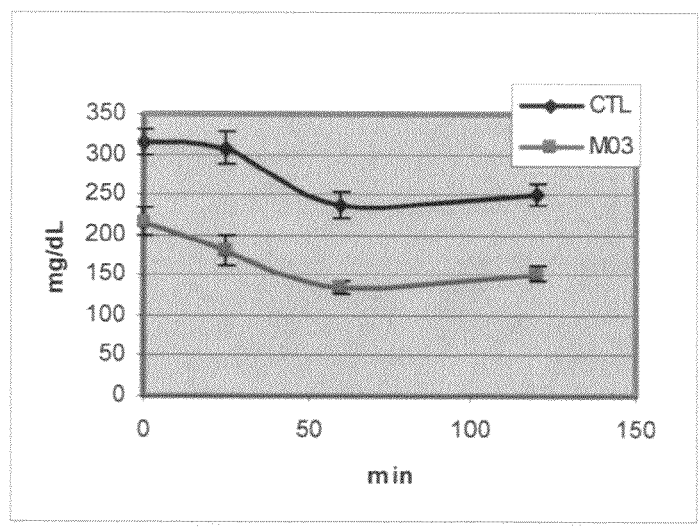

A) Glucose Levels 8 week old db/db mice were treated with either the preparation (1 mg/kg/day) from Example 2, or a control, for 120 days. Glucose levels were measured after 16 hours of overnight fasting. The results are shown in FIG. 15A.

B) Glucose Tolerance 6 week old db/db mice were injected intraperitoneally with either the control, or the preparation (1 mg/kg/day) of Example 2 for 12 days. After fasting for 16 hours overnight, the mice were subjected to a glucose tolerance test. The measurements of glucose levels at various time points are shown in FIG. 15B.

C) Insulin Tolerance 6 week old db/db mice were injected intraperitoneally with either the control or the preparation (1 mg/kg/day) from Example 2 for 10 days followed by insulin injection (1 IU/kg) on the last day intraperitoneally. The measurements of glucose levels at various time points are shown in FIG. 15C.

EXAMPLE 5

HPLC Analysis of Gallocyanine Analogue Preparation

The preparation from Example 2 was analyzed by HPLC and found to consist of a mixture of at least four different compounds. Although the preparation itself was very effective, the actual contribution made by each component was an unknown factor. Consequently, the Gallocyanine analogue preparation made according to the method of Example 2 was resolved on a preparative HPLC column where fractions were collected as GCA-F1, GCA-F2, GCA-F3 and GCA-F4, as seen in the diagram of FIG. 16.

EXAMPLE 6

Assays on HPLC Fractions

Each of the isolated fractions from Example 5 were tested separately for effects on Wnt activity as well as the suppression of Dkk activity using the Wnt dependent luciferase assay described in U.S. patent application Ser. No. 10/849,067. In FIG. 17, it can be seen that fractions GCA-F3 and GCA-F4 both display high levels of blockage of Dkk mediated Wnt suppression. The results with the unfractionated GCA pool from Example 2 is also shown as a comparison. It can be seen that the profiles of the unfractionated pool and GCA-F3 are similar, especially with regard to inhibiting Wnt in the absence of Dkk when higher levels of the compounds were used. On the other hand, the GCA-F4 fraction differs from GCA-F3 in that as the concentration of GCA-F4 is raised there is no evidence of inhibition of Wnt activity whereas GCA-F3 has a drop in Wnt activity such that it returns to a baseline at 50 μM. In a similar fashion, blockage of the inhibition of Wnt activity by Dkk is seen at the lower levels of GCA-F3 but this is lost at the higher levels, presumably since at these levels GCA-F3 itself is blocking Wnt activity. In contrast, the level of Dkk resistant Wnt activity in the presence of GCA-F4 continues to rise even at the highest concentration of GCA-F4, presumably because of the lack of Wnt inhibition caused by the compound itself. It can also be seen in this Example that two of the fractions (GCA-F1 and GCA-F2) are essentially inactive (as seen in FIG. 18) and consequently the results previously described for the gallocyanine analogue preparation used in Examples 3 and 4 are likely derived from the GCA-F3 and GCA-F4 compounds in the unfractionated pool. NMR studies were then carried out to determine the nature of the structure of GCA-F3 and GCA-F4 to evaluate their exact structures. Structures were not determined for the GCA-F1 and GCA-F2 compounds since these Gallocyanine derivatives did not seem to influence Wnt activity. A comparison of the structures of the Gallocyanine analogues GCA-F3 and GCA-F4, as well as the original gallocyanine prototype is shown in FIG. 19. It can be seen here that in GCA-F3, the gallocyanine starting product was modified by the addition of methyl groups to create an O-methyl substitution and transform the carboxyl group into a methyl ester. Thus, GCA-F3 corresponds to a Core Structure I compound as shown in this Figure. (Core structure designations are from related pending U.S. patent application Ser. No. 11/598,916.) In contrast, the GCA-F4 analogue differs from the Gallocyanine prototype in lacking the carboxyl group of the latter—a structure sufficiently different to allow definition of two new core structures (Structure IX and Structure X), also shown in FIG. 19. The discovery of the effectiveness of this analogue may allow the generation of an entirely new series of compounds that may have application in treating diseases related to Wnt activity.

EXAMPLE 7

Synthesis of M76, M77, M94, M115 and M116

Synthesis of M76, M77, M94, M115 and M116.

These compounds were selected on the basis of the virtual screening and are related to M03 in having a similar design:

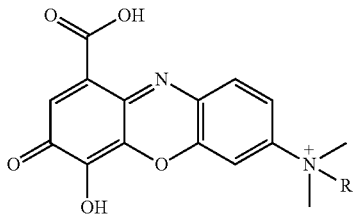

except instead of the propyl group of M03, R is a heptanyl, octanyl, or propenyl group for M76, M77 and M94 respectively, and

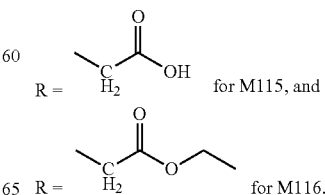

These compounds were not tested but they can be synthesized in the same manner described previously for M01, M02 and M03 in related U.S. patent application Ser. No. 11/598,916, with the exception of substituting the appropriate alkyl iodide for the quarternization step.

EXAMPLE 8

Synthesis and Assays of Compounds M228 and M230

Synthesis of M228.
A mixture of 200 mg of 2-amino-3,4,5,trimethoxy-gallic acid (0.88 mMoles), 142 mg of 5-methylisatin (0.88 mMoles) and 8 ml of water was heated at 110° C. overnight. TLC showed an almost complete reaction. After decanting the aqueous portion from the mixture, the residue was dissolved in dichloromethane (3 ml) and precipitated from hexane. Repeated hexane precipitation yielded 150 mg of M228 product. This was then used for the synthesis of M230.

Figure 20:
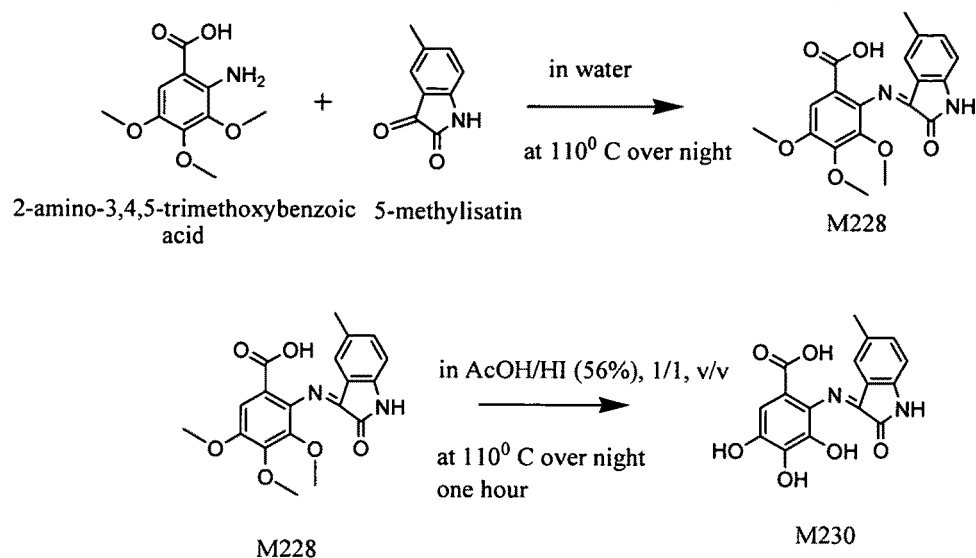
FIG. 20. Synthetic Pathway for M228, M230, M251, M333, M335, M338 and M339.
Figure 20:
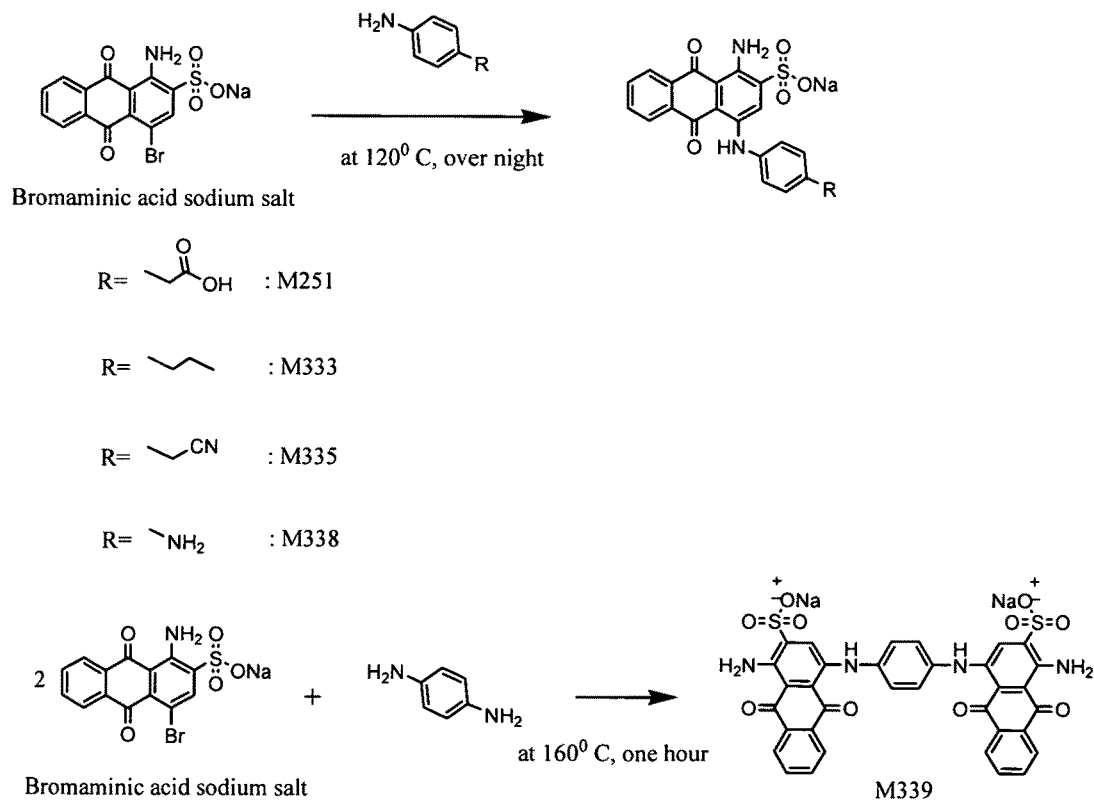

Synthesis of M230.
The synthetic pathways for the synthesis of these compounds are shown in FIG. 20. A mixture of 120 mg of M228 (0.32 mMoles) and 2 ml of 1:1 (v:v) acetic/HI was heated in a 12 ml pressure tube at 110° C. for one hour. The mixture was then poured into 20 ml of water. The resulting precipitate was collected by filtration and washed in water/ethanol. Ninety (90) mg of M230 product was recovered.

Figure 21:
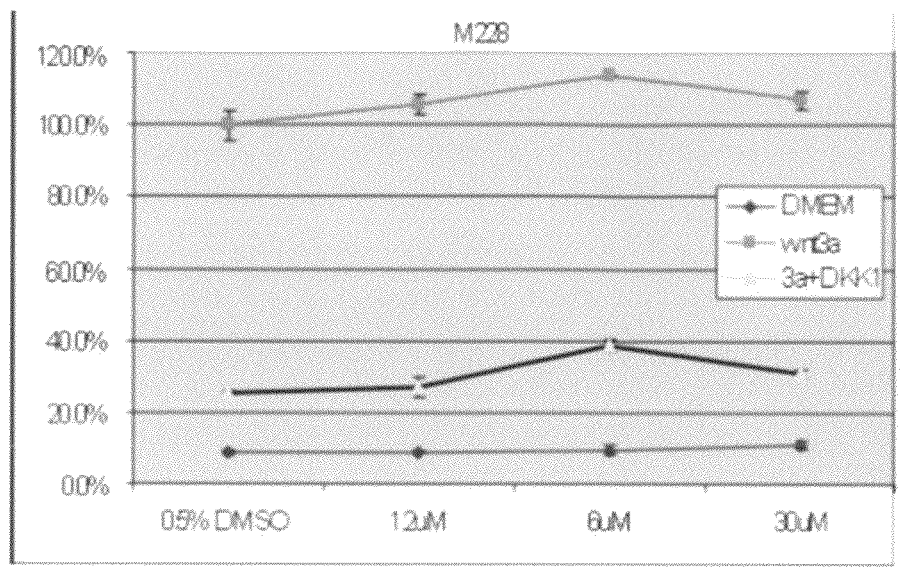
FIG. 21. Assay of effects of M228 and M230.
Figure 21:
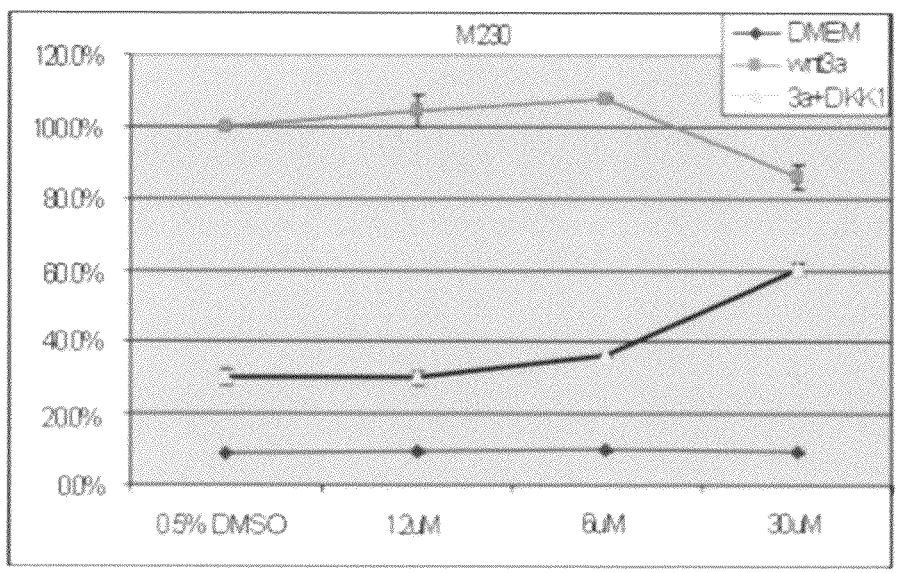

Assay of M228 and M230.
Assays were carried out at as described above and the results with M228 and M230 are shown in FIG. 21. The results in this figure show little effect on Wnt activity or Dkk suppression by M228 and are shown here only because M228 is the precursor for M230. In contrast, M230 shows an inhibition of the suppression of Wnt activity by Dkk. It is also possible that M230 is showing some inhibition of Wnt activity itself at the highest concentration of M230 tested. The only differences between M228 and M230 are the presence of hydroxyl groups in M230 in corresponding positions where M228 has methoxy groups.

EXAMPLE 9

Synthesis and Assays of M251, M333, M335, M338 and M339

Another series of related compounds from Example 1 that provided promising properties as judged by the virtual screening system were M251, M333, M335, M338 and M339. The various steps for the synthesis of these compounds are shown in FIG. 20.

Synthesis of M251, M333, M335 and M338.
A mixture of 400 mg (1 mmole) of bromaminic acid (sodium salt), 10 mg (0.045 nMoles) of copper carbonate, 400 mg (2.5 mMoles) of potassium acetate and 0.04 mMoles of an aniline with the appropriate substitution on the aromatic ring (See FIG. 22 for the individual substituents) in 10 ml DMF was heated at 120° C. overnight. The extent of the reaction was monitored by TLC and when the reaction was essentially complete, the DMF was removed in vacuo. Ten (10) ml of 1N HCl was added to the flask followed by the addition of 10 ml of water. Following filtration, the residue in the funnel was washed with methanol. The solid product gave yields of 152 mg, 24 mg, 150 mg and 86 mg for M251, M333, M335 and M338 respectively.

Synthesis of M339.
A diagram of this reaction is also included in FIG. 20. A mixture of 400 mg (1 mmole) of bromaminic acid (sodium salt), 10 mg (0.045 nmole) copper carbonate, 400 mg (2.5 mMoles) potassium acetate and 2 to 10 mMoles of 1,4-diaminobenzene in 10 ml DMF was heated at 160° C. for one hour. The extent of the reaction was monitored by TLC and after the reaction was essentially complete, the DMF was removed in vacuo. Ten (10) ml of 1N HCl was added to the flask followed by the addition of 10 ml of water. Following filtration, the residue in the funnel was washed with methanol. The reaction yielded 100 mg of solid product.

Figure 22:
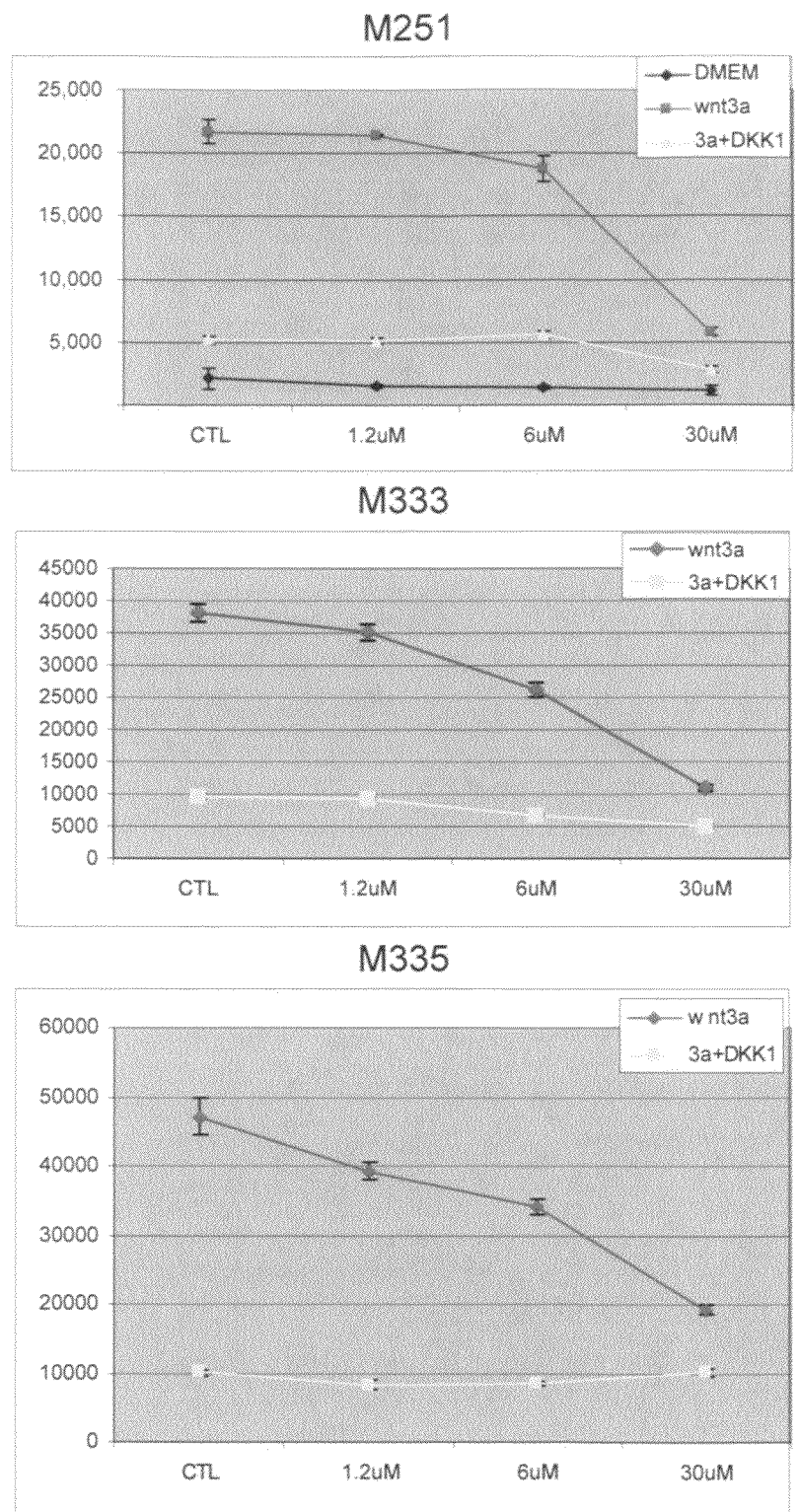
FIG. 22. Assay of effects of M251, M333 and M335.
Figure 23:
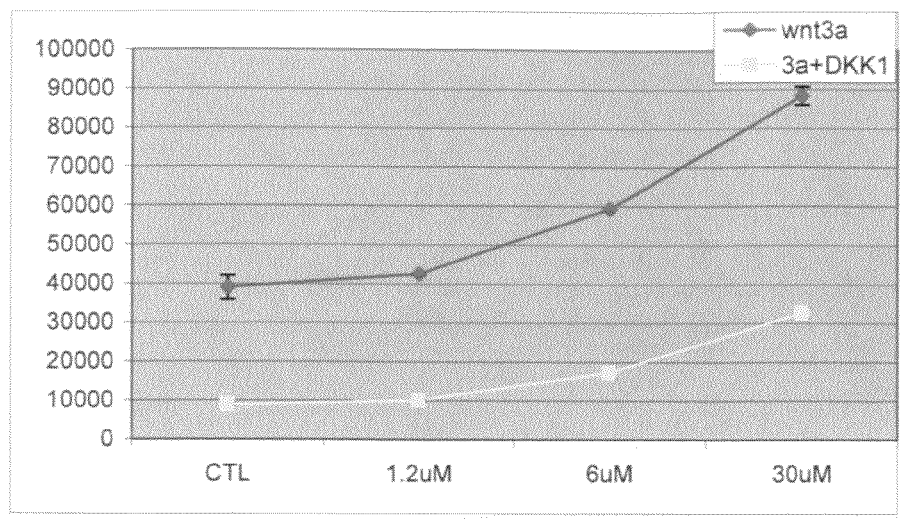
FIG. 23. Assay of effects of M338 and M339.
Figure 23:
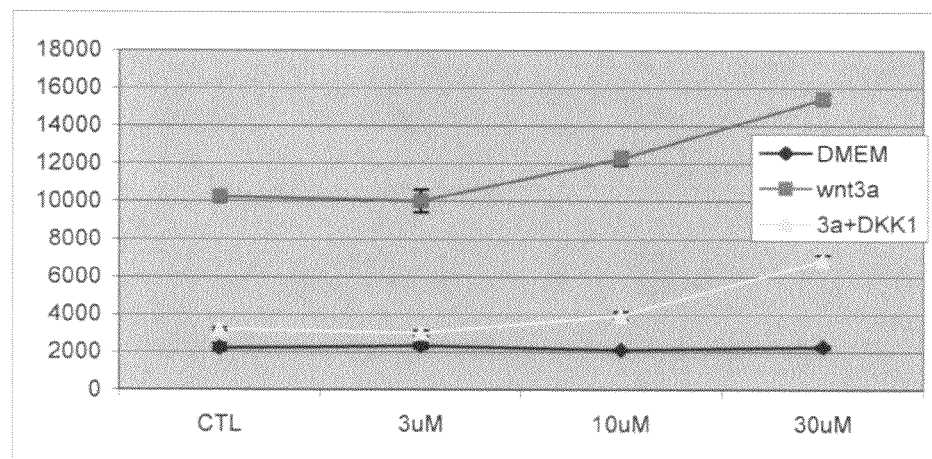

Assays of M251, M333, M335, M338 and M339.
Assays were carried out as described above and the results with M251, M333 and M335 are shown in FIG. 22, while the results for M338 and M339 are shown in FIG. 23. It can be seen that M251, M333 and M335 all induce a loss of Wnt activity. In contrast, M338 and M339 can be seen to stimulate Wnt activity. Furthermore, the increase in activity also seems to be paralleled by a resistance to Dkk suppression.

EXAMPLE 10

Synthesis and Assay of M358

Figure 24:
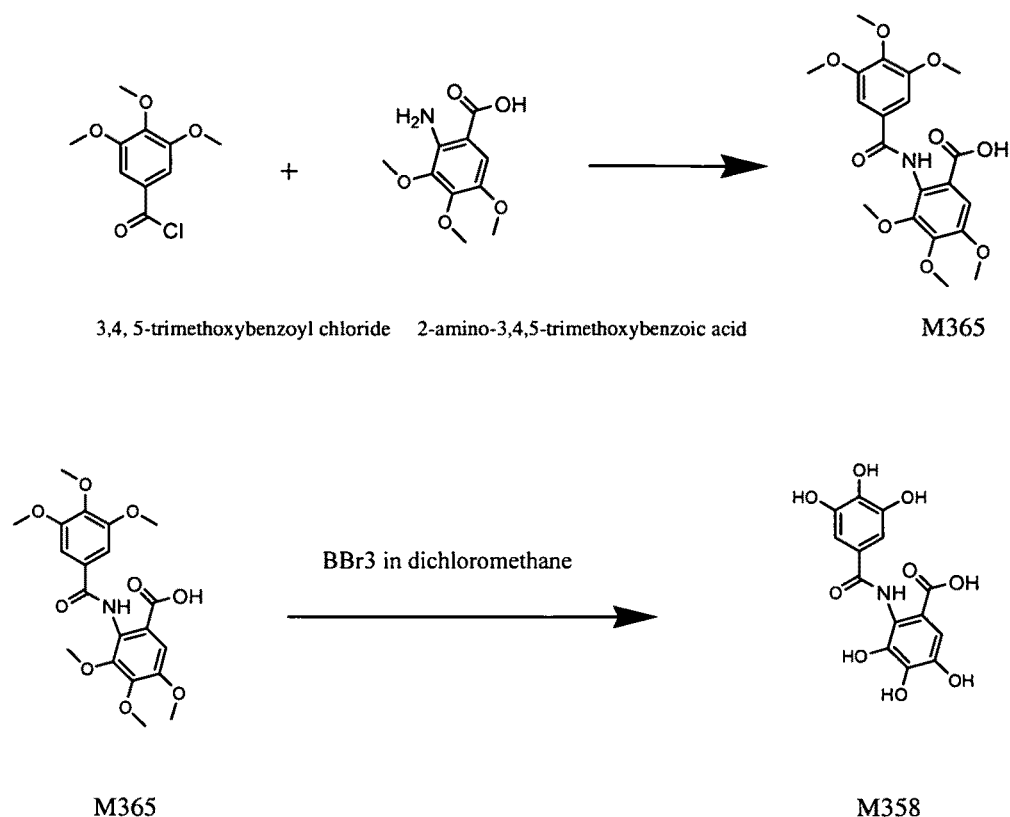
FIG. 24. Synthetic pathway of M358.

As described in related U.S. patent application Ser. No. 11/598,916, dimers and trimers of compounds that affect Wnt activity may have more effectiveness than the monomeric compound itself. One compound that scored well in the virtual screening process was M358, which is basically a dimeric form of gallic acid. The various steps for carrying out the synthesis of M358 are included in FIG. 24. A preliminary step in this process is the synthesis of M365 as a precursor for the next step.

Synthesis of M365.
A mixture of 4.6 g (20 mMoles) of 3,4,5-trimethoxybenzoyl chloride, 4.54 g (20 mMoles) of 2-amino-3,4,5-trimethoxybenzoic acid and a mixture of 3 ml of triethylamine in 30 ml of $CH_2Cl_2$ was stirred overnight at room temperature. After acidification with 1 N HCl, the product was washed with water. The product was purified by a silica gel column and elution performed with 100:1 (v:v) dichloromethane/methanol. The purified M365 was recovered with a yield of 630 mg.

Synthesis of M358.
M365 (240 mg, 0.57 nmol) was treated with 4.45 ml (4.5 mMoles) of $BBr_3$ (1 mol in methylenedichloride) at 0° C. and then stirred at room temperature for 16 hours. One (1) ml of methanol was then added and stirring was continued for 15 min. Twenty (20) ml of ether was then added to precipitate the product. HPLC chromatography demonstrated the presence of 4 peaks. Preparative HPLC was then carried out (FIG. 25) and M358-F1, M358-F2, M358-F3 and M358-F4 were isolated as shown.

Figure 26:
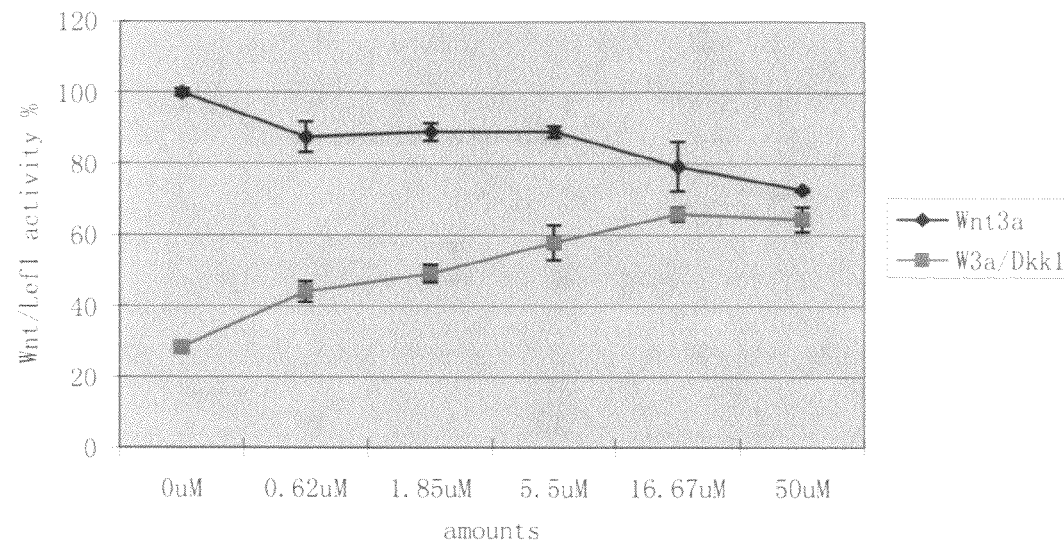
FIG. 26. Assay of effects of M358-pool and M358-F1 on Wnt activity.
Figure 26:
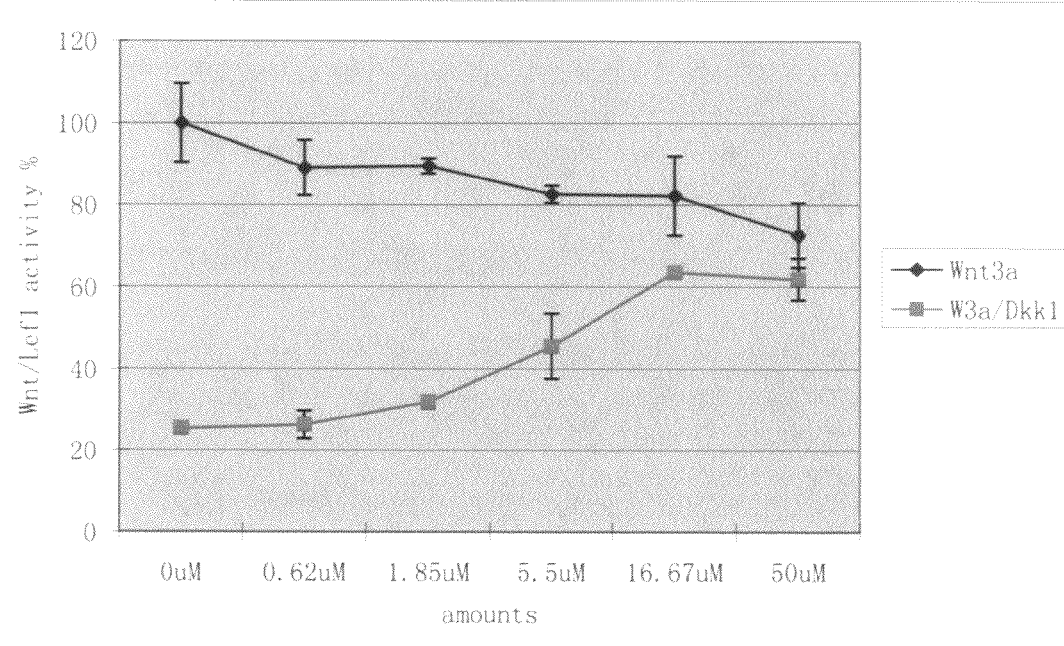
Figure 27:
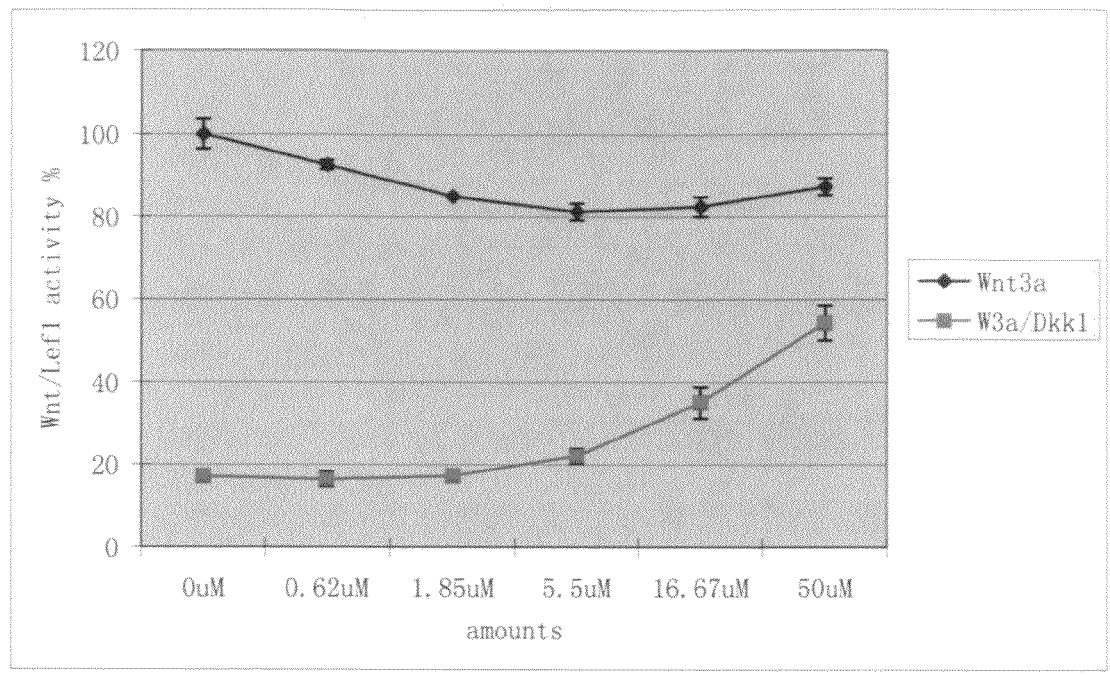
FIG. 27. Assay of effects of M358-F2 and M358-F3 on Wnt activity.
Figure 27:
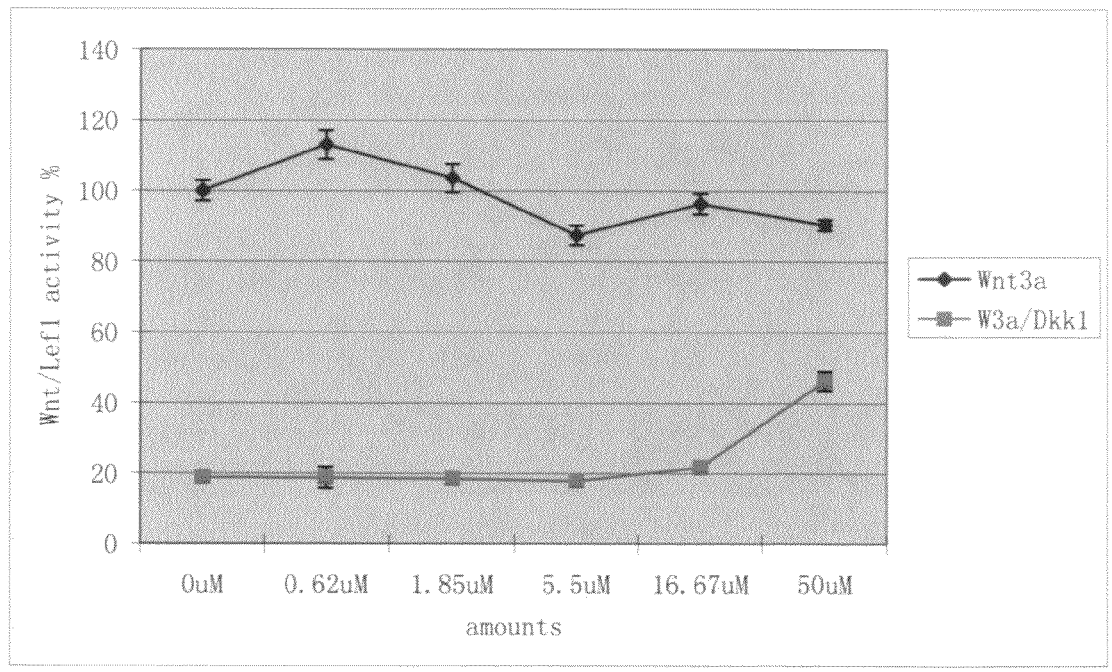

Assay of M358-pool, M358-F1, M358-F2, M358-F3 and M358-F4.
Assays were carried out at as described above and the results with M358-pool (the unfractionated product) and M358-F1 are shown in FIG. 26 while the results of M358-F2 and M358-F3 are shown in FIG. 27. It can be seen that in this group of products, only the M358-F1 compound seems to have activity in terms of suppression of Dkk inhibition. In contrast, the M358-F2 and M358-F3 products seem to show only a minimal amount of blockage of Dkk inhibition even at the highest concentration tested. NMR studies as well as mass spectroscopy analysis demonstrated that the M358-F1 compound corresponded to the expected M358 product, while the other compounds were of an undeterminate nature.

EXAMPLE 11

Synthesis and Assay of M361 DT

Although the M361 compound was evaluated in the virtual screening step as an oligomeric form of three gallic acid moieties held together by a triazine linker, a dimeric version was synthesized and tested using a dimeric form of M376 as the precursor. As such, the terms M361 and M376 have been reassigned to these molecules. In this synthetic route, the third position on the triazine ring was occupied by either a triethylamine moiety (M376T) or a di-isopropylethylamine (M376D) instead of a gallic acid substituent leading to a mixture of the two forms (T and D) as the product, and as such, referred to as M376DT.

mMoles (0.93 g) of M376DT dissolved in 90 ml of dichloromethane. The mixture was stirred overnight at room temperature and the next day, 5 ml of methanol was added with continued stirring. After 30 minutes, 5 ml of water was added and stirred for an additional 30 minutes to destroy excess boron tribromide. The products were concentrated in vacuo and precipitated with ether from a methanol solution to give 0.71 g of product. This was then purified by preparative HPLC and four fractions were resolved and collected as described above.

Assay of M361 DT Fractions.

Figure 29:
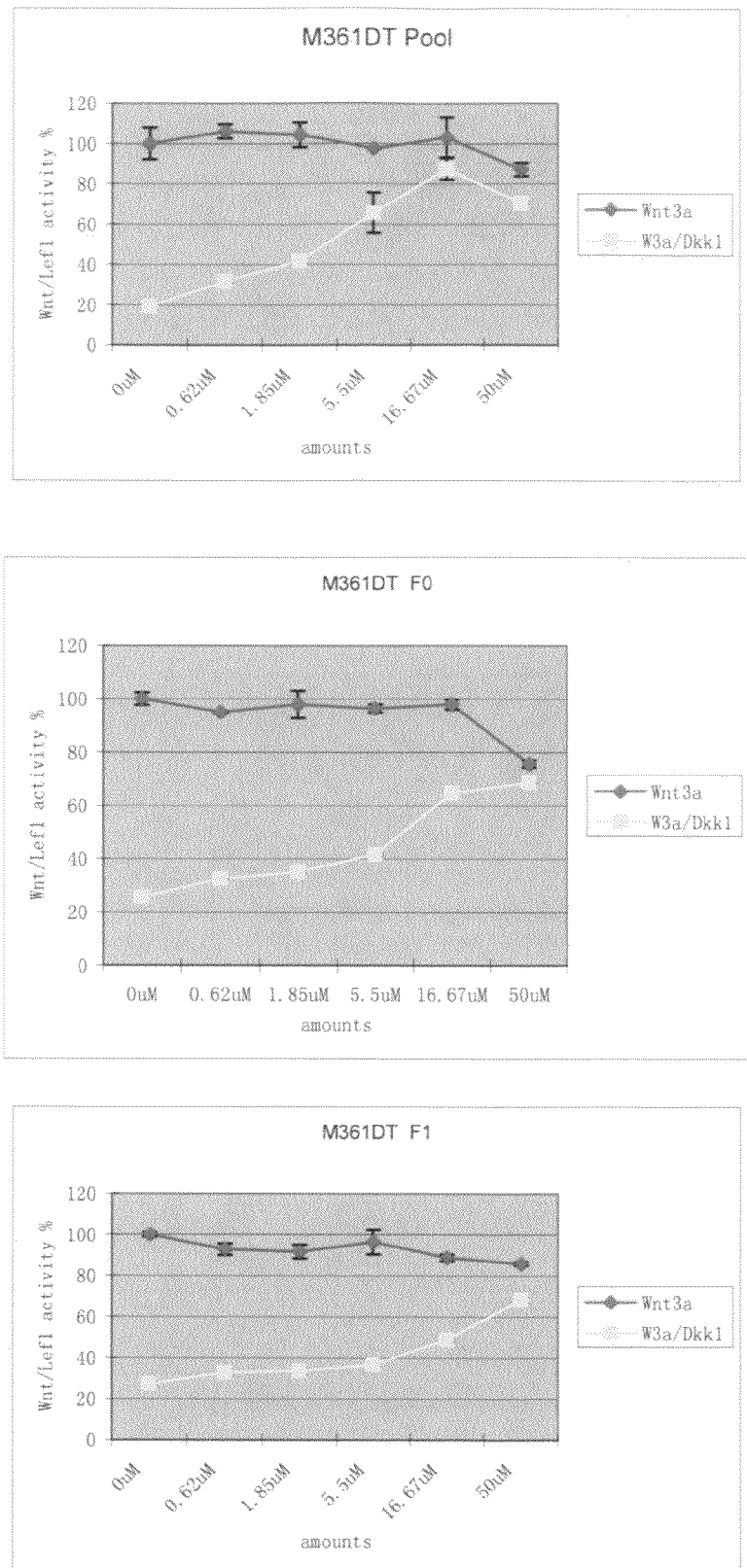
FIG. 29. Assay of effects of M36DT-pool, M36DT-F0 and M361 DT-F1.
Figure 30:
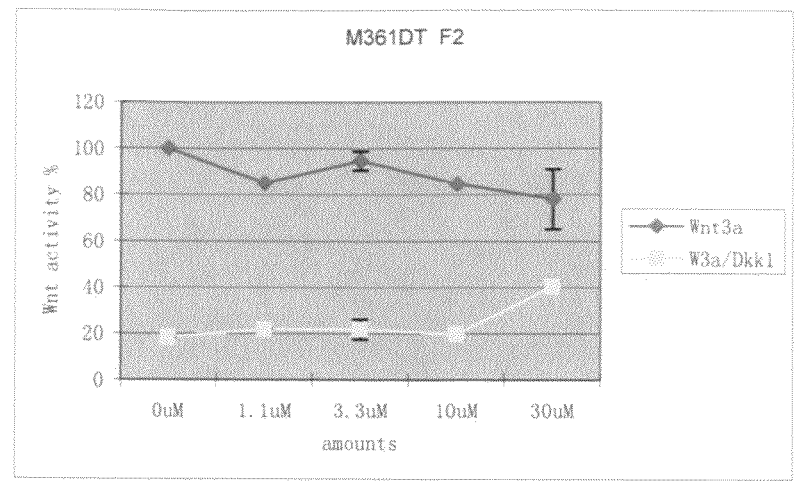
FIG. 30. Assay of effects of M361 DT-F2 and M361 DT-F3 on Wnt activity.
Figure 30:
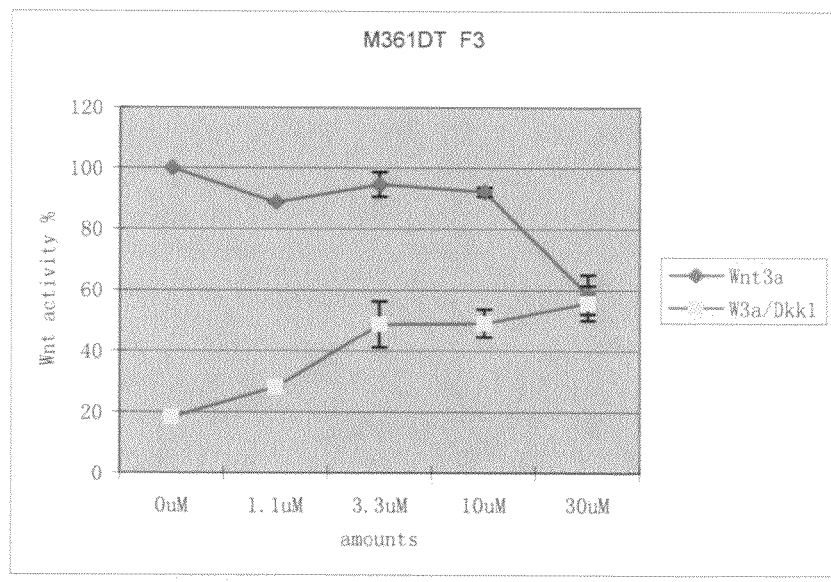

The biological assays of M361 DT-pool, M361 DT-F0, M361DT-F1, M361DT-F2 and M361DT-F3 were carried out as described above and the results from these assays are shown in FIGS. 29 and 30. It can be seen that the highest level of activity is seen with the M361 DT-F1 fraction, with the F1 fraction giving blockage of Dkk suppression only at the higher dosages and F2 providing little or no effects. F3 is

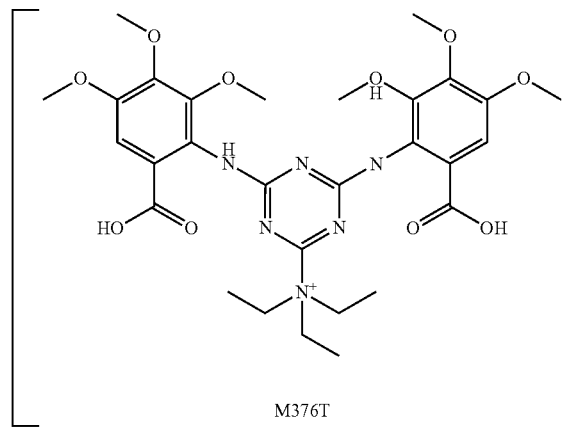
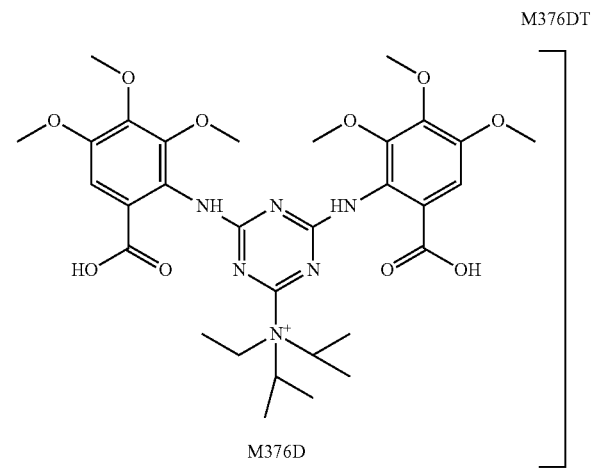

M376DT

M376T

M376D

Figure 25:
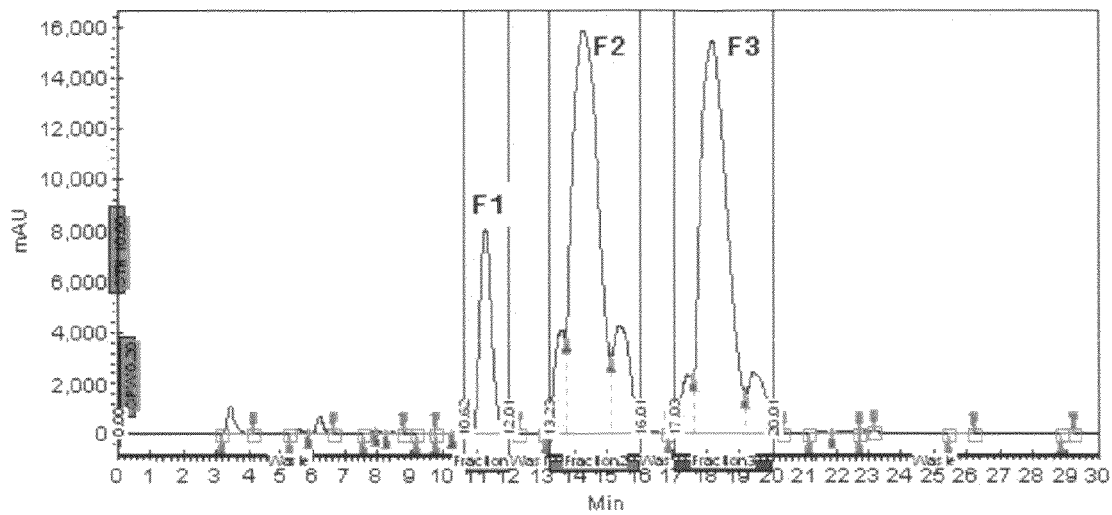
FIG. 25. HPLC profile of M358 and M361.
Figure 25:
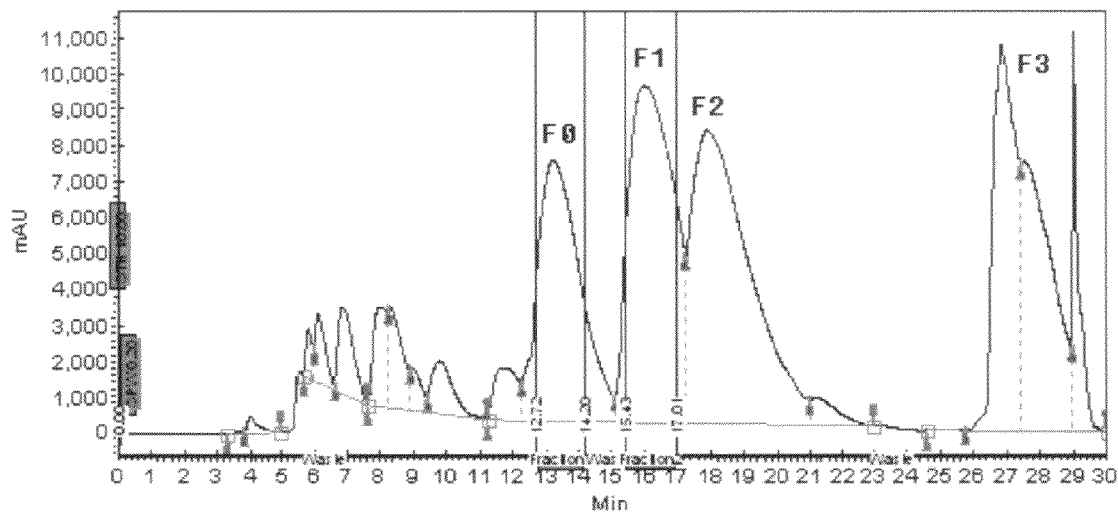
Figure 28:
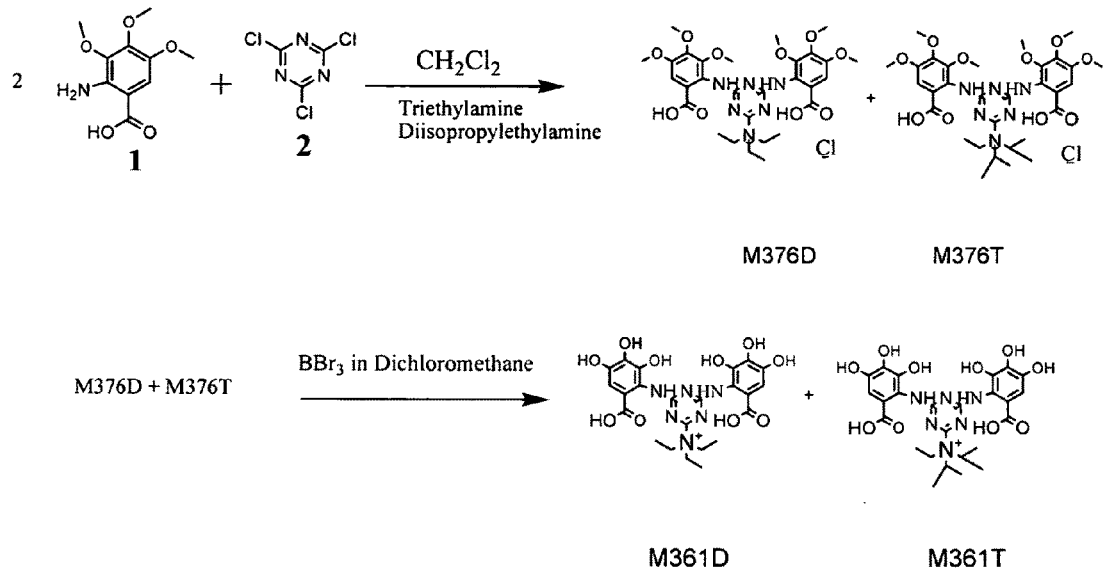
FIG. 28. Synthesis of M76DT, M361DT, M376T and M361T.
Figure 28:
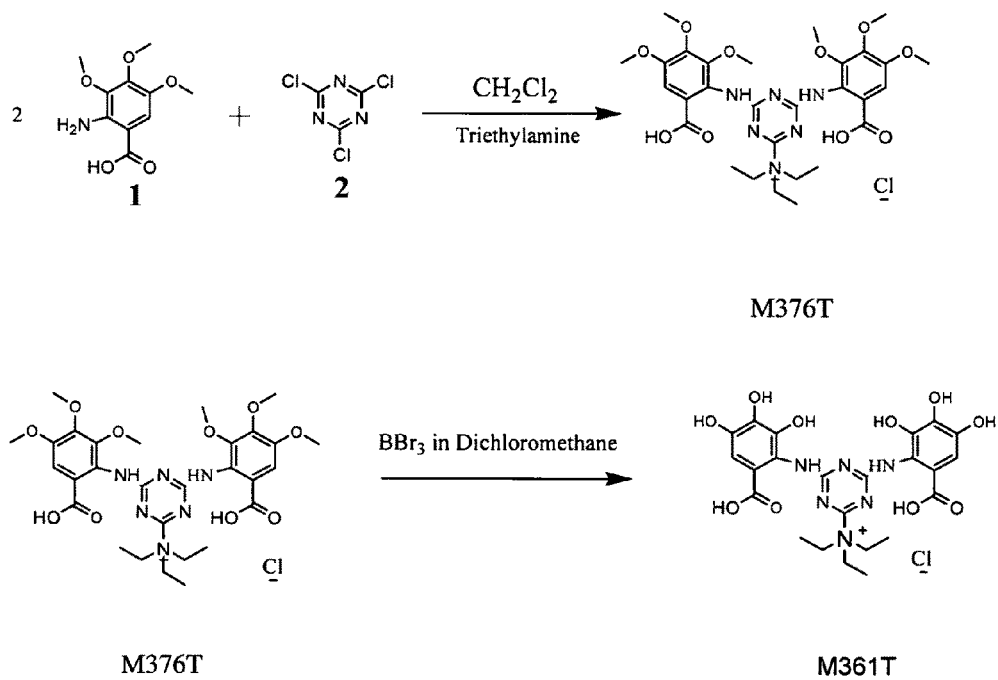

Subsequent steps continued with the M376DT mixture. The final product is now described as M361DT. HPLC analysis showed that as seen with some of the preceding synthetic processes, the product demonstrated multiple peaks that were individually collected. A diagram of the results of the HPLC used for the preparation of the various fractions is shown in FIG. 25 where fractions M361-F0, M361-F1, M361-F2 and M361-F3 were individually collected. It should also be pointed out that although HPLC is capable of separating out chemically different products of the M361 process, this separation does not extend to separation between the M and T forms and only holds for the more chemically distinct forms. The steps that were used to carry out this synthesis are shown in FIG. 28 and described more completely below.

Synthesis of M376DT:

A mixture of 25 g (110 mMoles) of 2-amino-3,4,5-trimethoxybenzoic acid (1), 6.5 g (35 mMoles) of 2,4,6-trichloro-1,3,5-triazine (2) in 500 ml of dichloromethane containing 20 ml of triethylamine and 20 ml of diisopropylethylamine was stirred overnight at room temperature. After concentration in vacuo, the residue was purified by silica gel chromatography (dichloromethane/methanol, 8/2). The purified product yield was 12.55 g and as discussed above, comprised a mixture of M376D and M376T.

Synthesis of M361 DT:

Twenty four (24) ml of a 1M solution (24 mMoles) of $BBr_3$ in dichloromethane were added dropwise to a solution of 1.5 more complicated since it also shows some degree of blockage of Dkk suppression but also displays a stronger degree of inhibition of Wnt activity at the higher dosages. The M361 DT-F0 fraction was subsequently determined to correspond to the expected M361 dimeric form of gallic acid, and the M361DT F1 fraction was an incomplete reaction where not all of the methoxy groups on the M376DT precursor were converted into hydroxyl groups such that a single methoxy group was retained at some position on the compound. The structures of the other byproducts were not established.

EXAMPLE 12

Synthesis and Assay of M361T

Since the interpretation of the M376DT is complicated by each HPLC fraction likely representing a mixture of the D and T forms in Example 11, another synthesis was carried out where the triethylamine/di-isopropylethylamine mixture (used in the step joining the galliocyanine moieties to the triazine ring) was replaced by only triethylamine. Under these conditions, only the T products may be formed. The steps and products of this series of steps are shown in FIG. 28 and described more completely below.

Synthesis of M376T:

A mixture of 25 g (110 mMoles) of 2-amino-3,4,5-trimethoxybenzoic acid (1) and 6.5 g (35 mMoles) of 2,4,6- trichloro-1,3,5-triazine (2) in 500 ml of dichloromethane containing 40 ml of triethylamine was stirred overnight at room temperature. After concentration in vacuo, the residue was purified by silica gel chromatography using dichloromethane:methanol (4:1, v:v). The yield of purified product was 12.15 g.

Synthesis of M361T:

A solution of $BBr_3$ (24 ml [24 mMoles] of 1M $BBr_3$ in dichloromethane) was added dropwise to a solution of M376T (0.93 g, [1.5 mmol] M376T in 90 ml dichloromethane). After stirring overnight at room temperature, 5 ml of methanol was added the next day with continued stirring. After 30 minutes, 5 ml of water was added and stirred for a further 30 minutes to destroy excess boron tribromide. The product ware concentrated in vacuo and precipitated with ether from a methanol solution to give 0.67 g of product. Preparative HPLC was carried out and the first two peaks (equivalent to M361 DT-F0 and M361 DT-F1) were collected with yields of 50 mg for M361T-F0 and 60 mg for M361T-F1.

Assays of M361T-F0 and M361T-F1.

Figure 31:
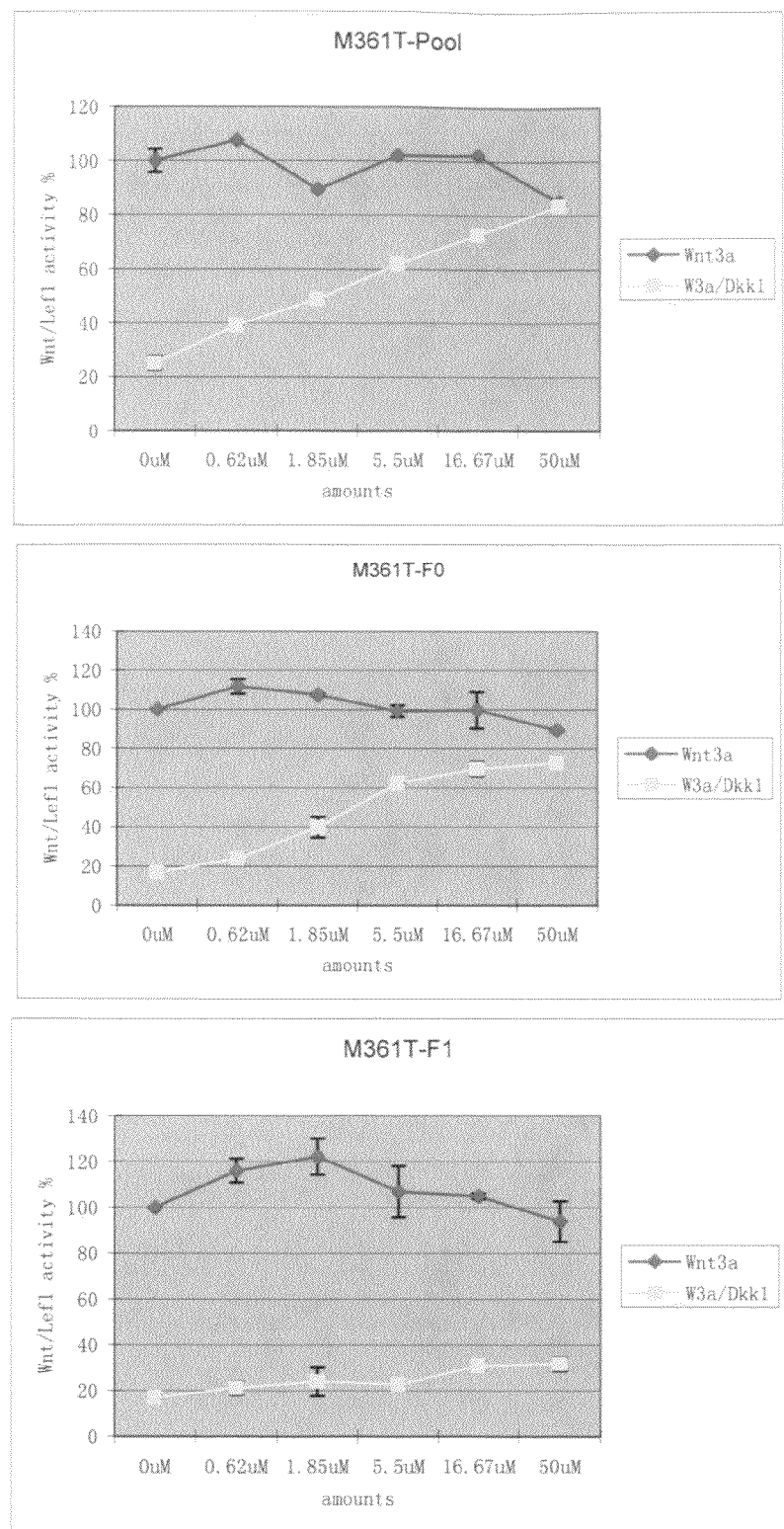
FIG. 31. Assay of effects of M361T on Wnt activity.

The biological assays of M361T-pool, M361T-F0 and M361T-F1, were carried out as described above and the results from these assays are shown in FIG. 31. The results with the M361T-pool are similar to those seen previously for the M361 DT-pool except that it does not show any abatement at the highest dose. This profile of the M361T-F0 is similar to that seen previously for the M361 DT-F0, implying that the D and T forms may be equivalent. On the other hand, the effects of the M361T-F1 are much less pronounced than previously seen for M361 DT-F1 which may be interpreted as only the M361 D-F1 form being active in the DT mixture. Structures were established for both of these compounds and similar to the results with M361 DT, the M361T-F0 was the expected digallic product and the M361T-F1 was again an incomplete reaction product where one of the methoxy groups of the M376T precursor remained unconverted into a hydroxyl group.

EXAMPLE 13

Synthesis and Assay of M380

One of the compounds designed in this series is an analogue of the IC15 described in U.S. patent application Ser. No. 10/849,067 as a Wnt inhibitor. The difference between the IC15 prototype and the M380 compound may be seen in FIG. 32 where it may be seen that IC15 was used as the starting material before conversion into the M380 compound. Briefly, a mixture of 29 mg (0.06 mMoles) of IC15, 10 ml ethanol and 1 ml acetic acid was reacted with 34 μl of 55% hydrazine (0.6 mMoles) for one hour at 100° C. Ten (10) mg of solid product (M380) was recovered by filtration.

Assay of M380.

Figure 33:
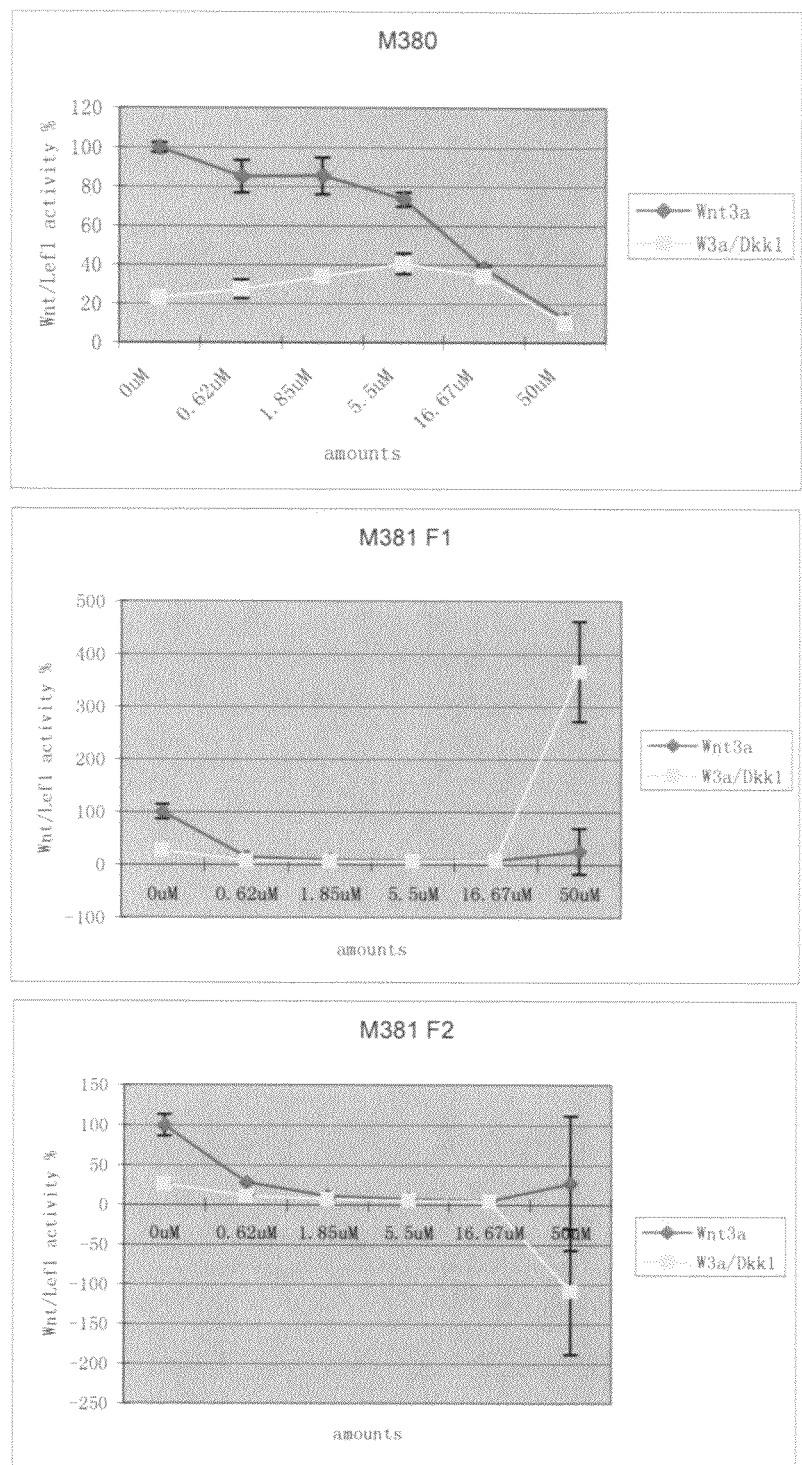
FIG. 33. Assay of M380, M381-F0 and M381-F1 on Wnt activity.

The biological assay of M380 was carried out as described above and the results are shown in FIG. 33 where it can be seen that there is dose dependent inhibition of Wnt activity with the M380 compound.

EXAMPLE 14

Synthesis and Assay of M381

Another analogue of IC15 (designated as M381) was designed where the hydroxyl groups in IC15 were replaced by methoxy groups.

Synthesis of M381.

Figure 32:
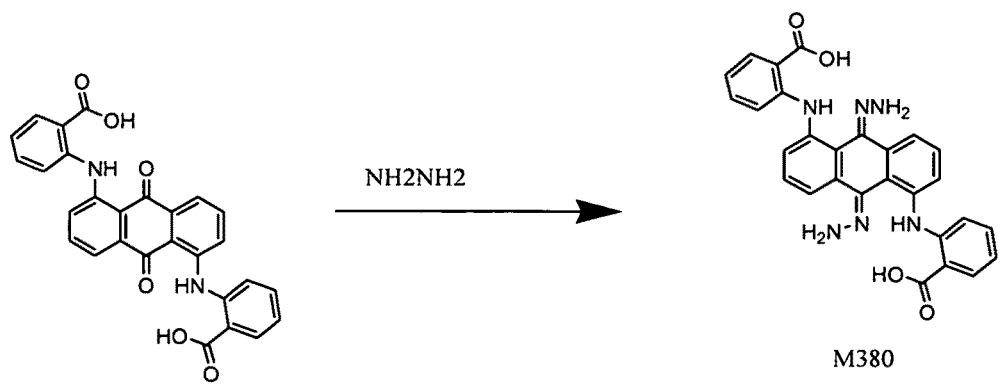
FIG. 32. Synthesis of M380 and M381.
Figure 32:
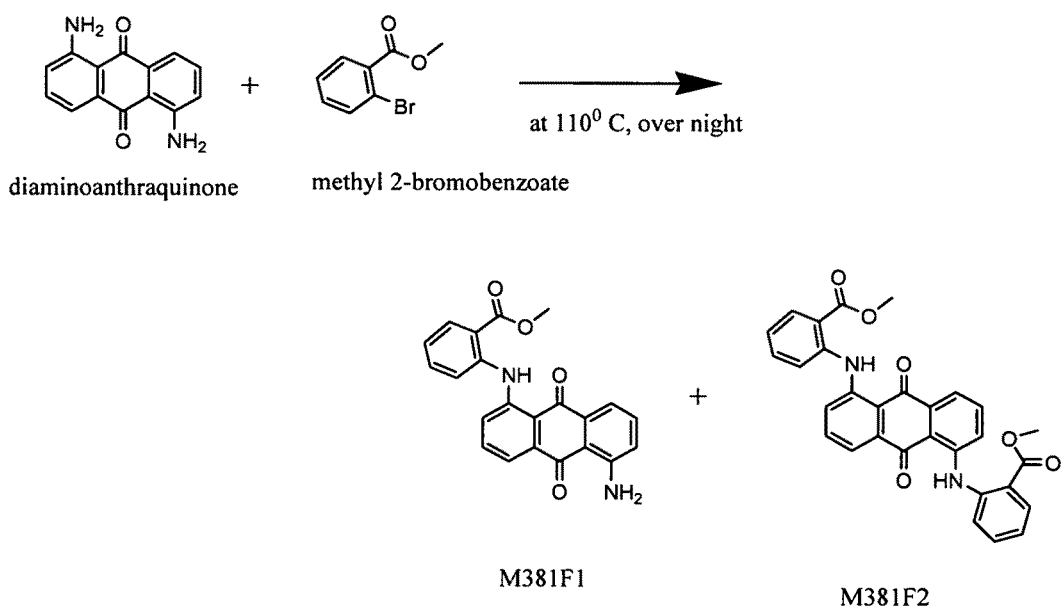

A mixture of 1 g (4 nMoles) of diaminoanthraquinone, 0.1 g of copper carbonate, 3.3 g potassium t-butyl oxide in 30 ml DMF was reacted with 2.3 ml of methyl 2-bromobenzoate (3.4 g, 16 mMoles) at 100° C. overnight. The reaction product was purified by HPLC resulting in the presence of two peaks (data not shown) that were collected as M381-F1 and M381-F2 respectively. As shown in FIG. 32, it is believed that M381-F2 had the intended structure, while M381-F1 was an incomplete reaction where a gallic acid type moiety was attached to only one of the amine groups of the diaminoanthraquinone precursor. Both the mono-substituted (M381-F1) and disubstituted (M381-F2) were separated by preparative HPLC and tested for biological activity.

Assay of M381-F1 and M381-F2.

The biological assays of M381-F1 and M381-F2 were carried out as described above and the results are shown in FIG. 33. The results with these compounds seems to show an almost immediate shutdown of Wnt activity at even the lowest concentrations. There is some question concerning the last data points since one (M381-F1) seems exceedingly high and the other seems exceedingly low (M381-F2). The overall trend is that both of these compounds are potent Wnt inhibitors.

EXAMPLE 15

Selected Compounds and Assays From "Enzo" Series

As described in Example 1, a series of compounds were identified by virtual screening of a physical library obtained from NCI and some commercial sources. After an evaluation of the scores from the screening, selected compounds were obtained from the library sources and tested as described above. In this particular screening, a large number of compounds were identified that were able to inhibit Wnt activity. In addition, a few compounds were found to be able to block suppression of Dkk. It should be noted that although a few different libraries were utilized, due to overlap in representation, the compounds described in this section were able to be obtained from a single source (NCI) and the NCI designations as well as internal code names are given below:

Compounds Inhibiting Wnt Activity:

| Code # | NCI # |
| --- | --- |
| Enzo172 | 205612 |
| Enzo173 | 215556 |
| Enzo174 | 106444 |
| Enzo188 | 8192 |
| Enzo191 | 274903 |
| Enzo192 | 85193 |
| Enzo195 | 49694 |
| Enzo197 | 377384 |
| Enzo198 | 602247 |
| Enzo201 | 664283 |
| Enzo517 | 401145 |
| Enzo525 | 37223 |
| Enzo527 | 37590 |
| Enzo530 | 147482 |
| Enzo531 | 168523 |
| Enzo539 | 95407 |
| Enzo540 | 87511 |
| Enzo551 | 5889 |
| Enzo552 | 8517 |
| Enzo562 | 2805 |

Compounds Blocking Dkk Inhibition of Wnt Activity:

| Code # | NCI # |
|---|---|
| Enzo522 | 297535 |
| Enzo558 | 37180 |
| Enzo560 | 1705 |

Figure 34:
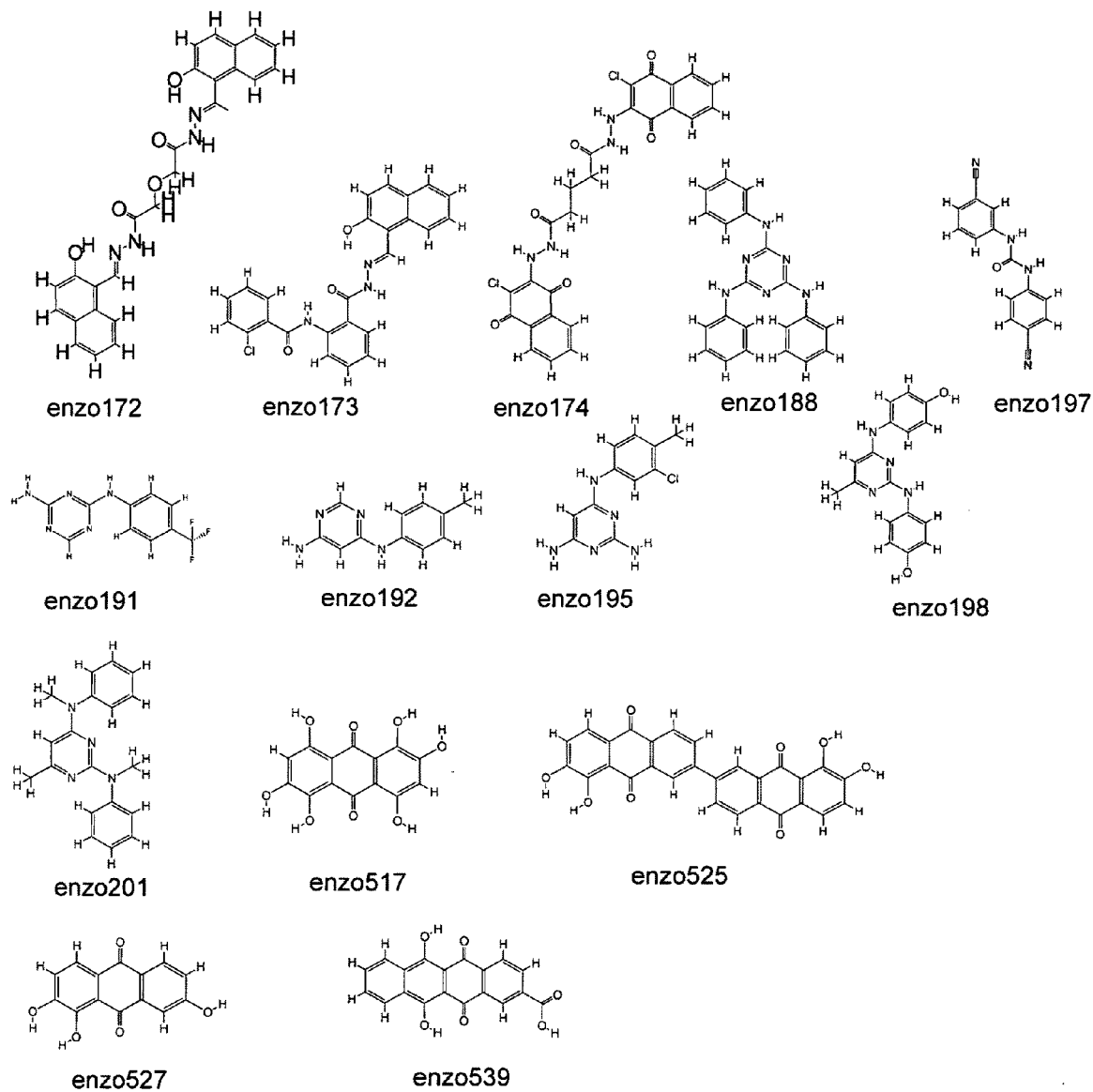
FIG. 34. Structures of various "Enzo" series compounds tested for Wnt activity.
Figure 35:
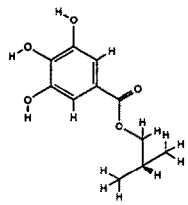
FIG. 35. Structures of various "Enzo" series compounds tested for Wnt activity.
Figure 35:
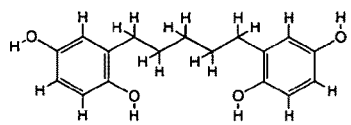
Figure 35:
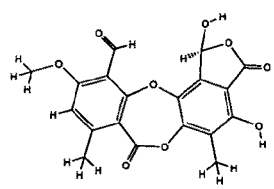
Figure 35:
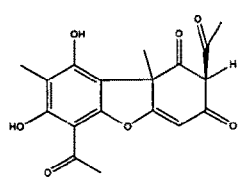
Figure 35:
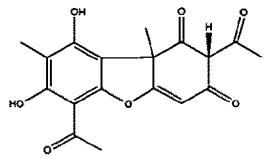
Figure 35:
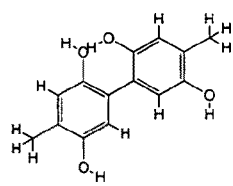
Figure 35:
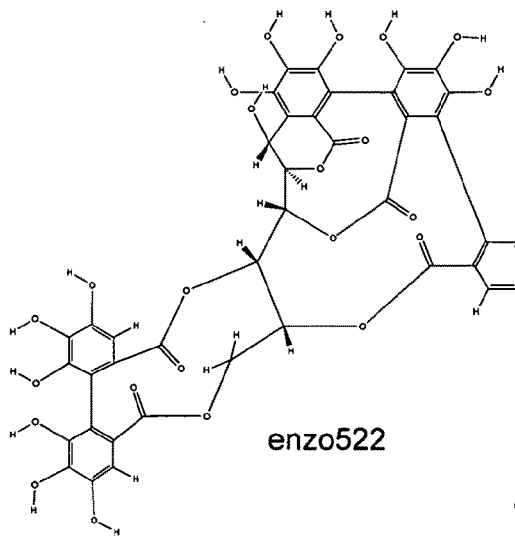
Figure 35:
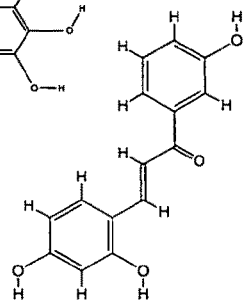
Figure 35:
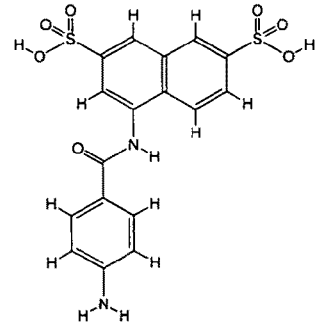
Figure 36:
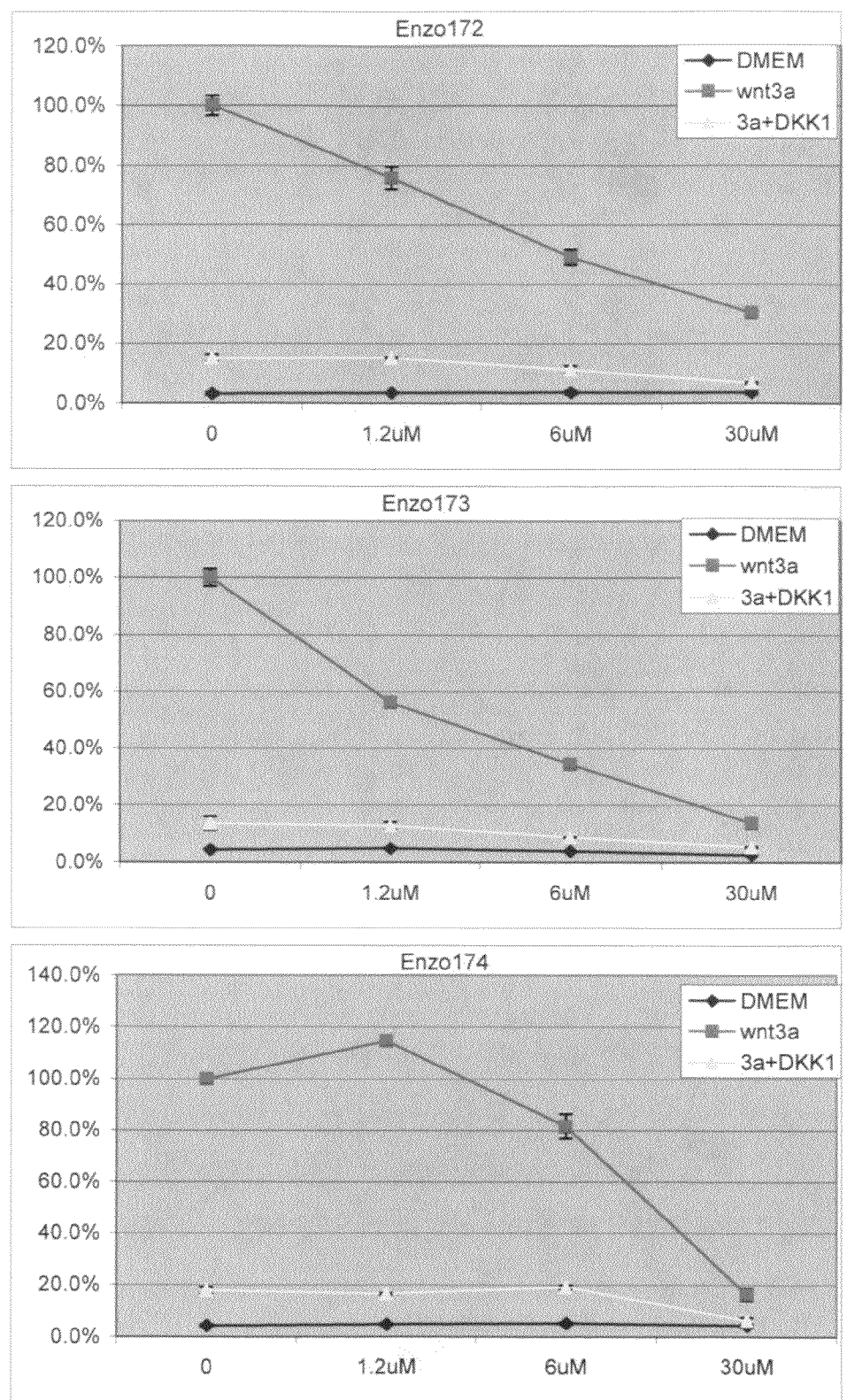
FIG. 36. Assay of enzo172, 173 and 174 on Wnt activity.
Figure 37:
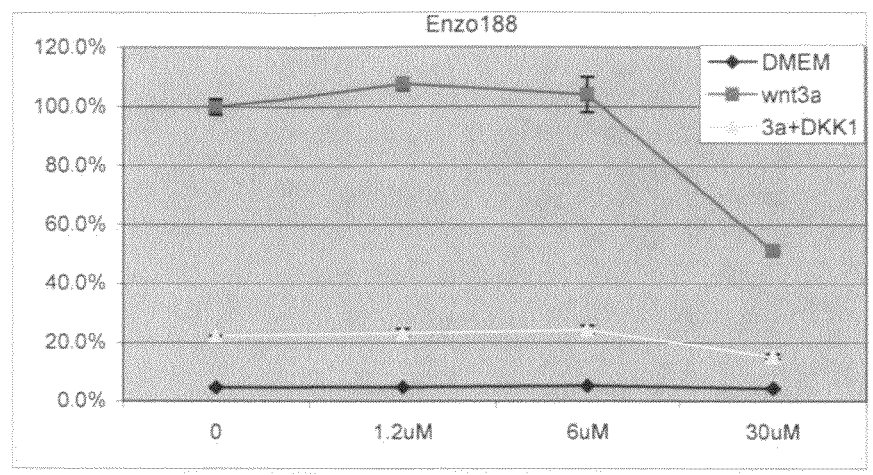
FIG. 37. Assay of enzo188, 191 and 192 on Wnt activity.
Figure 37:
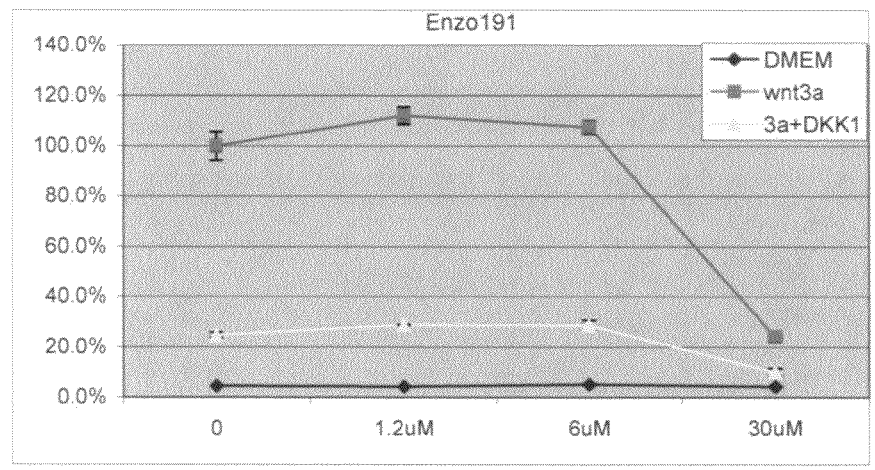
Figure 37:
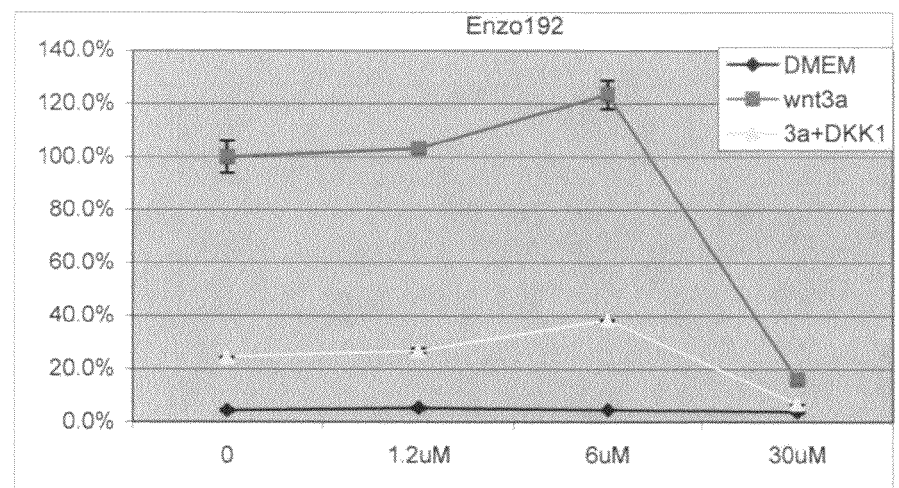
Figure 38:
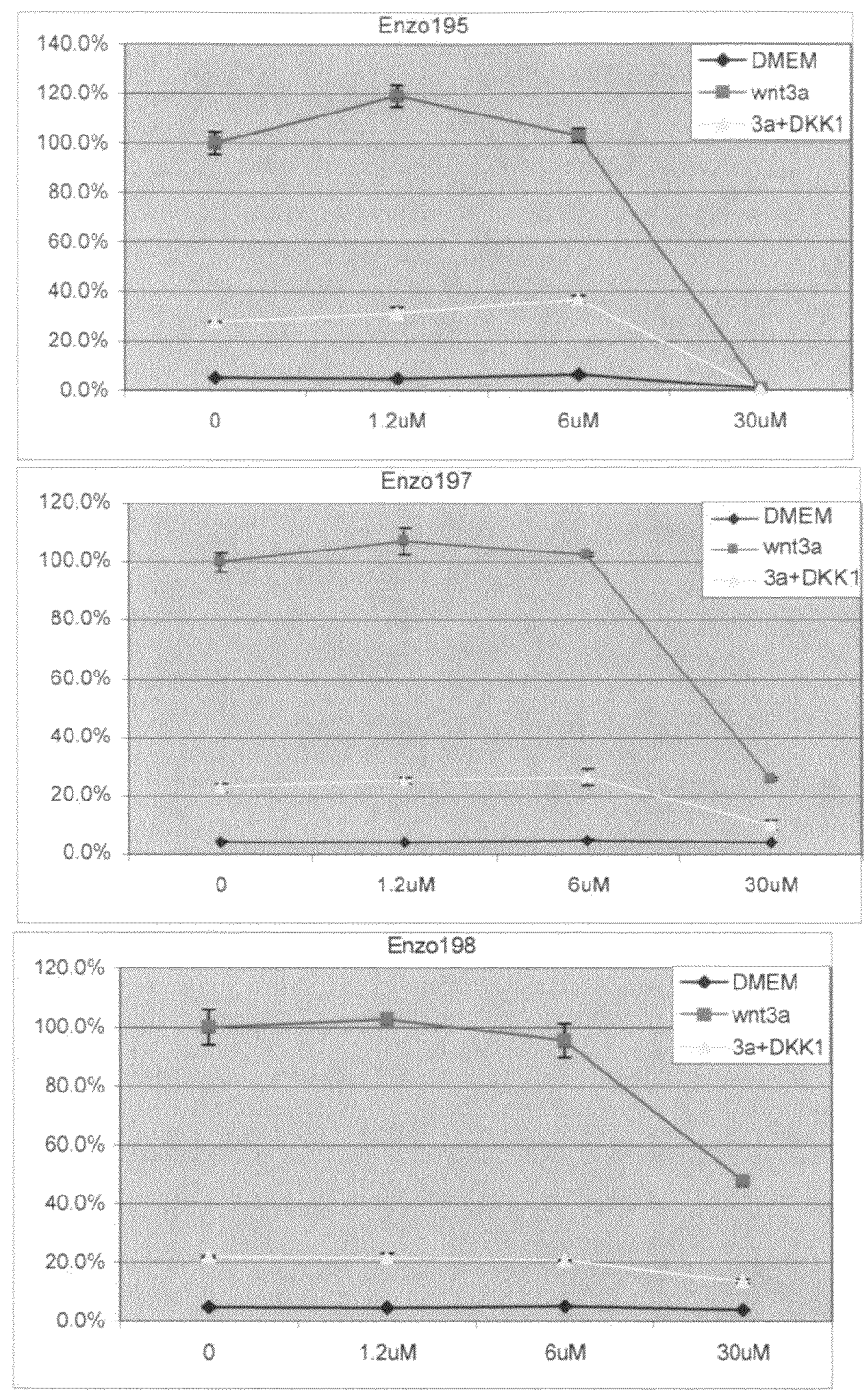
FIG. 38. Assay of enzo195, 197 and 198 on Wnt activity.
Figure 39:
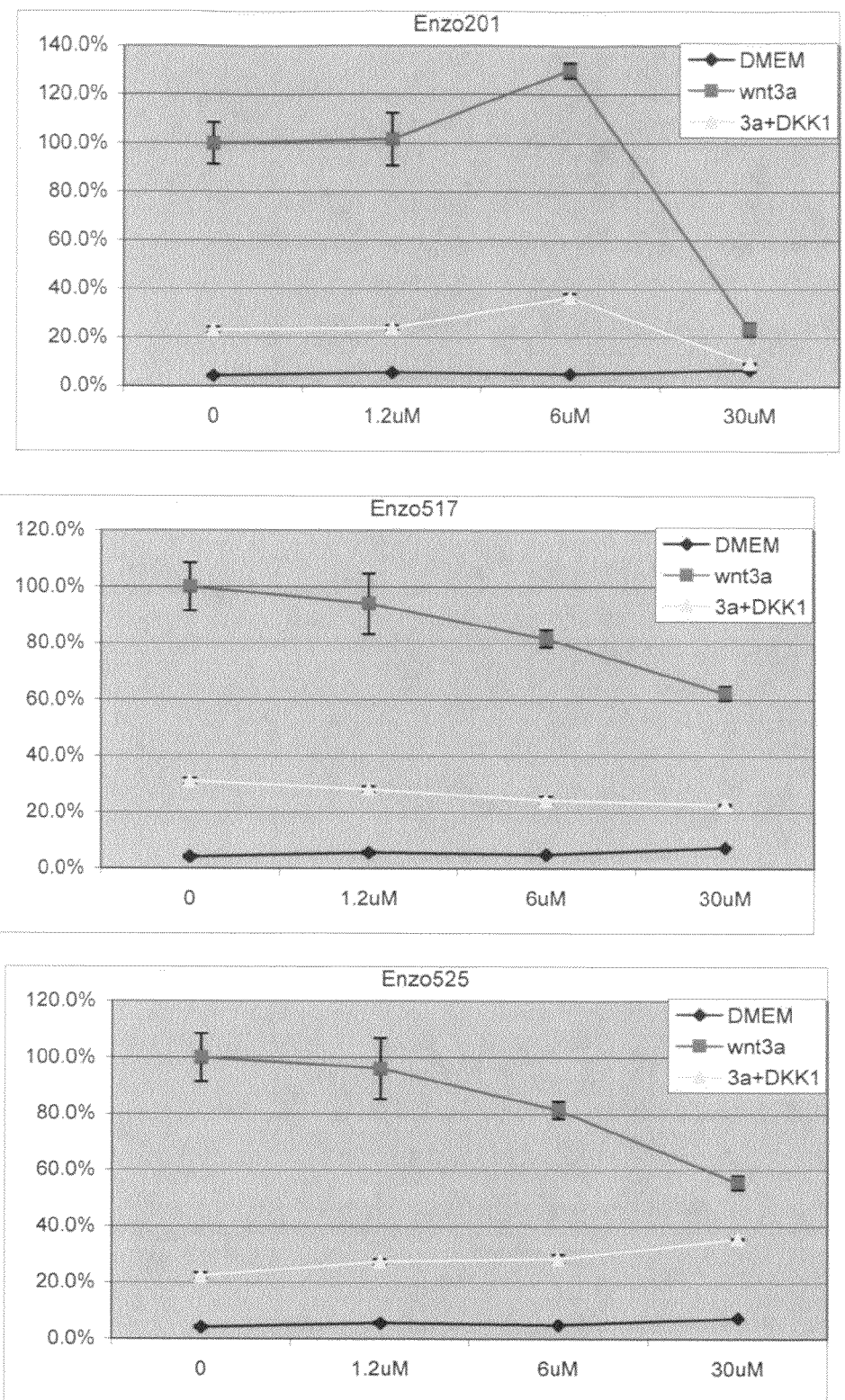
FIG. 39. Assay of enzo201, 517 and 525 on Wnt activity.
Figure 40:
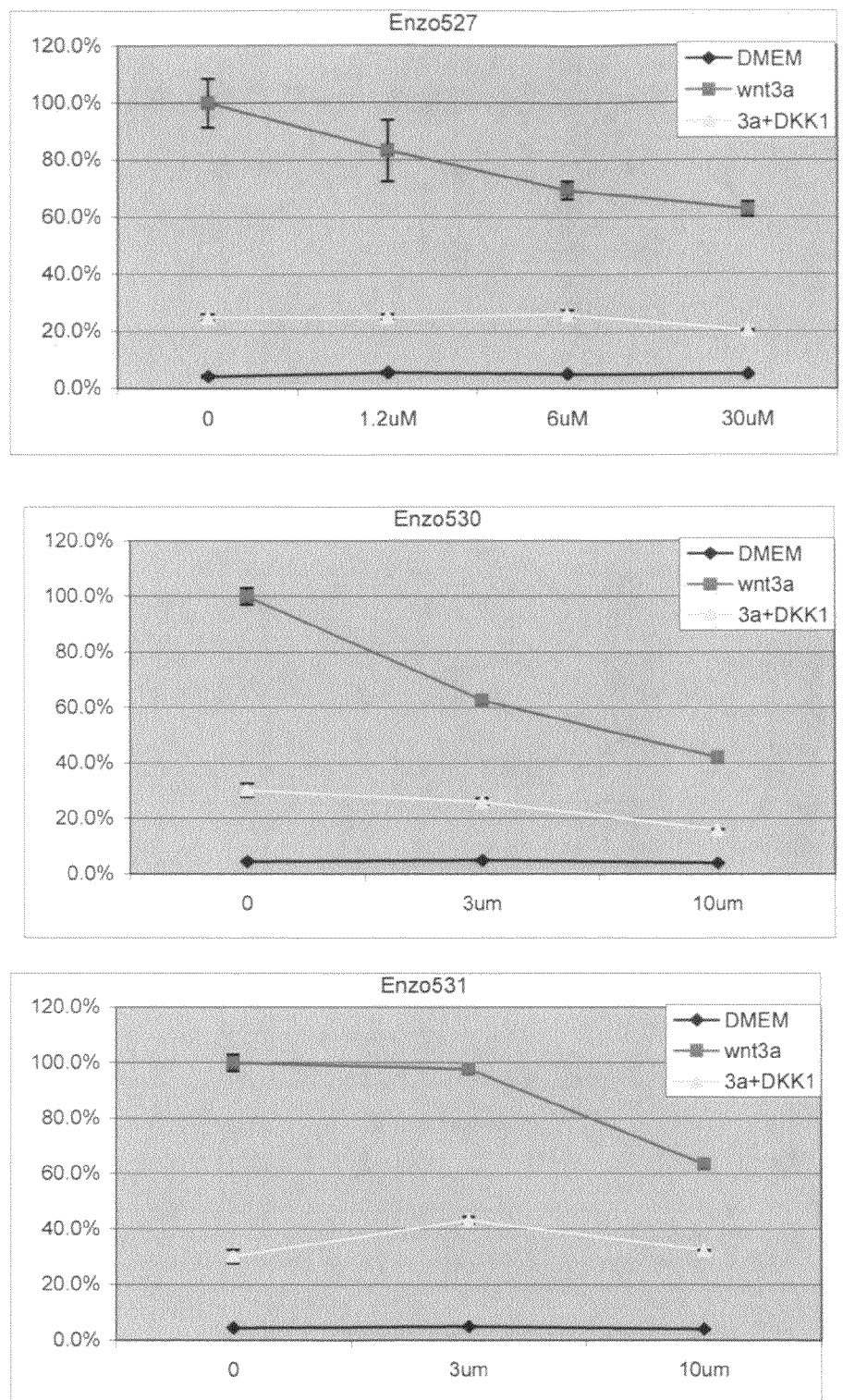
FIG. 40. Assay of enzo527, 528 and 530 on Wnt activity.
Figure 41:
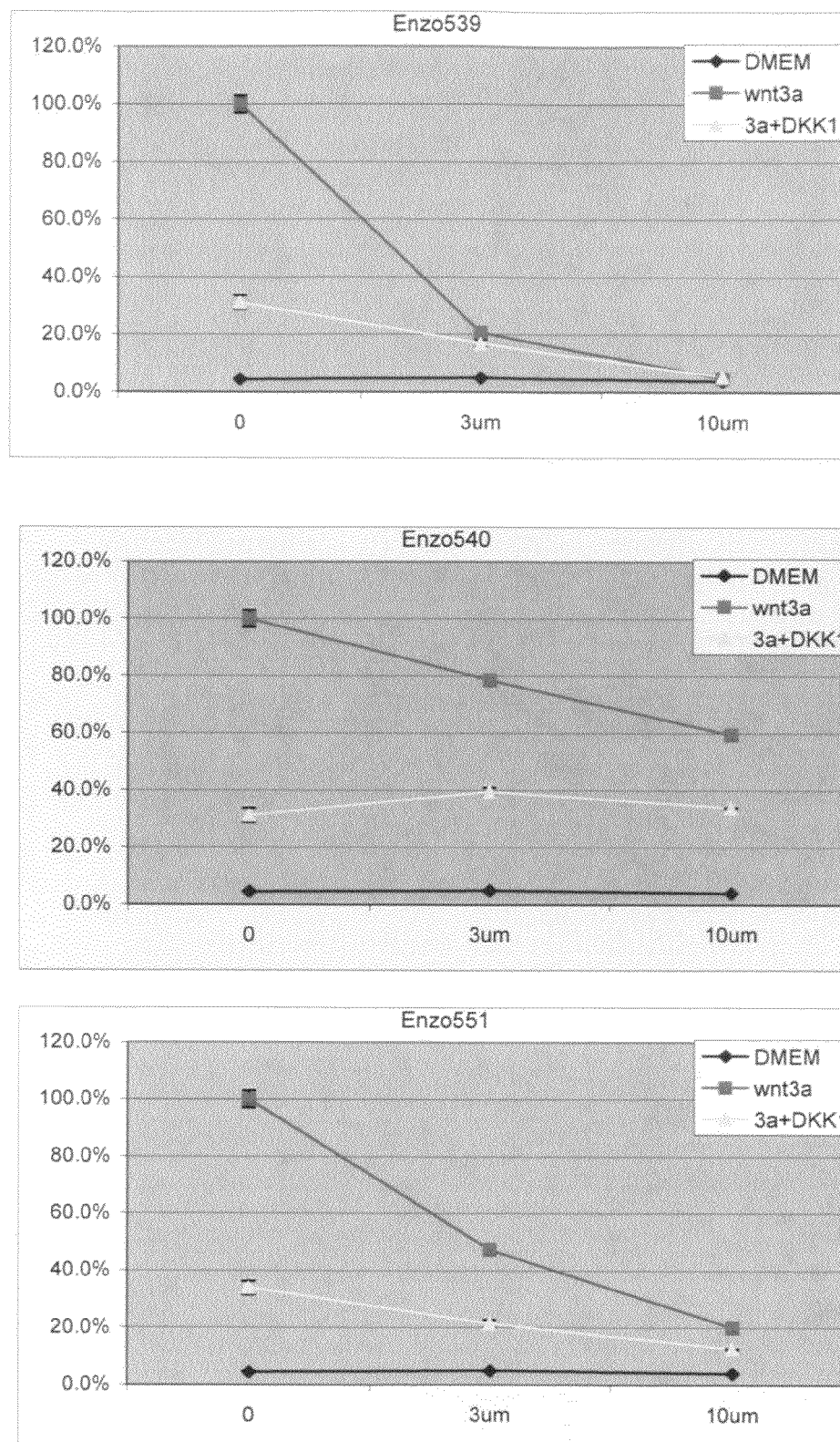
FIG. 41. Assay of enzo531, 539 and 540 on Wnt activity.
Figure 42:
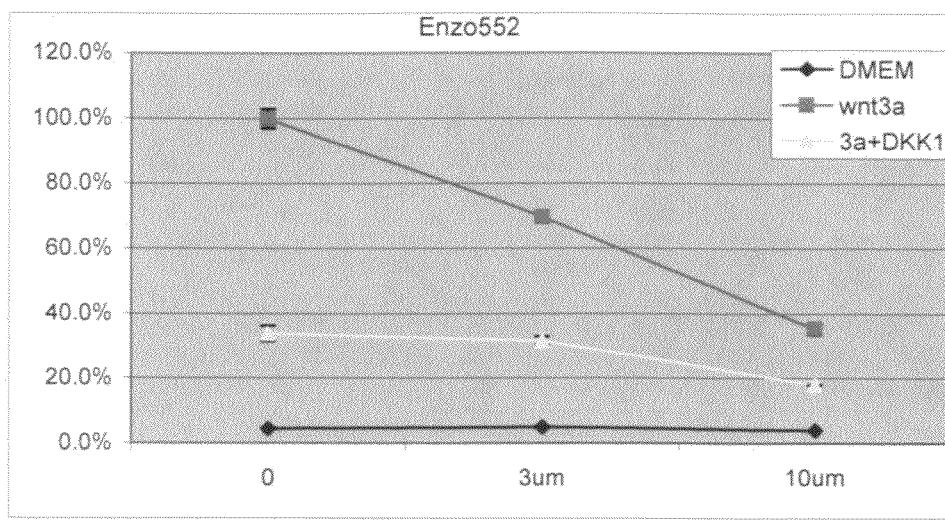
FIG. 42. Assay of enzo551, 552 and 562 on Wnt activity.
Figure 42:
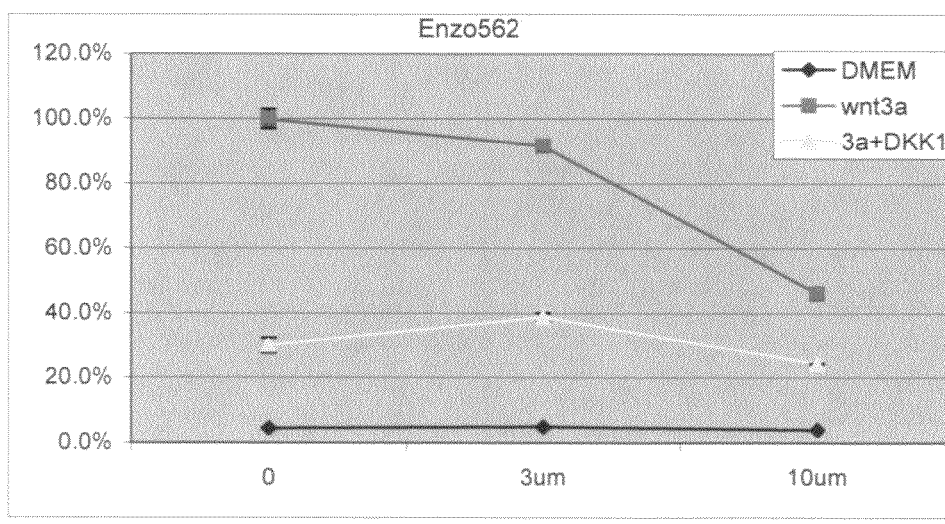
Figure 43:
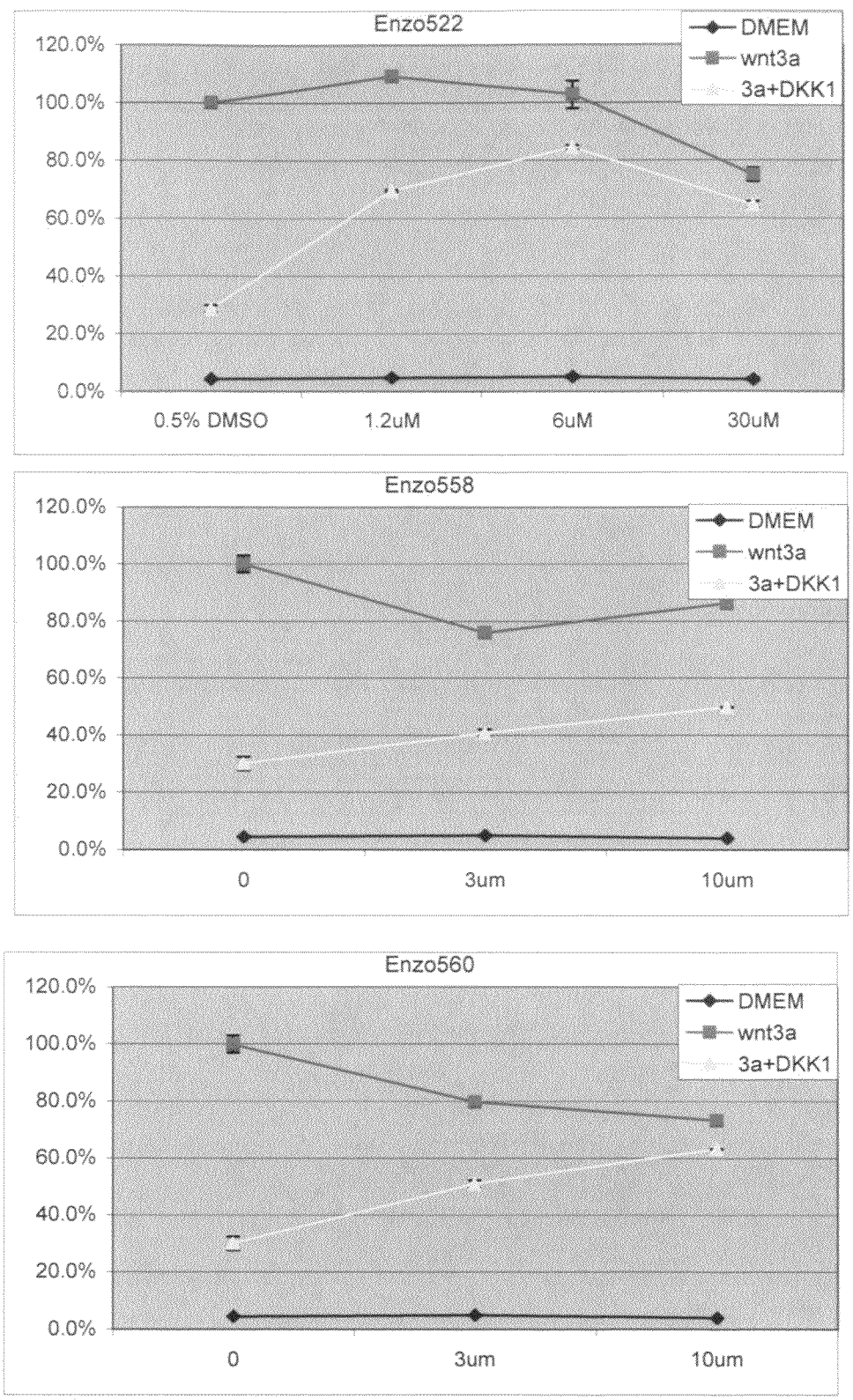
FIG. 43. Assay of enzo522, 558 and 560 on Wnt activity.

The structures of this series of compounds are shown in FIGS. 34 and 35. The assay results of the compounds with Wnt activity inhibition are shown in FIGS. 36-42 while the results with compounds that block Dkk suppression of Wnt activity are given in FIG. 43.

EXAMPLE 16

Synthesis of Biotinylated Gallocyanine

Figure 44:
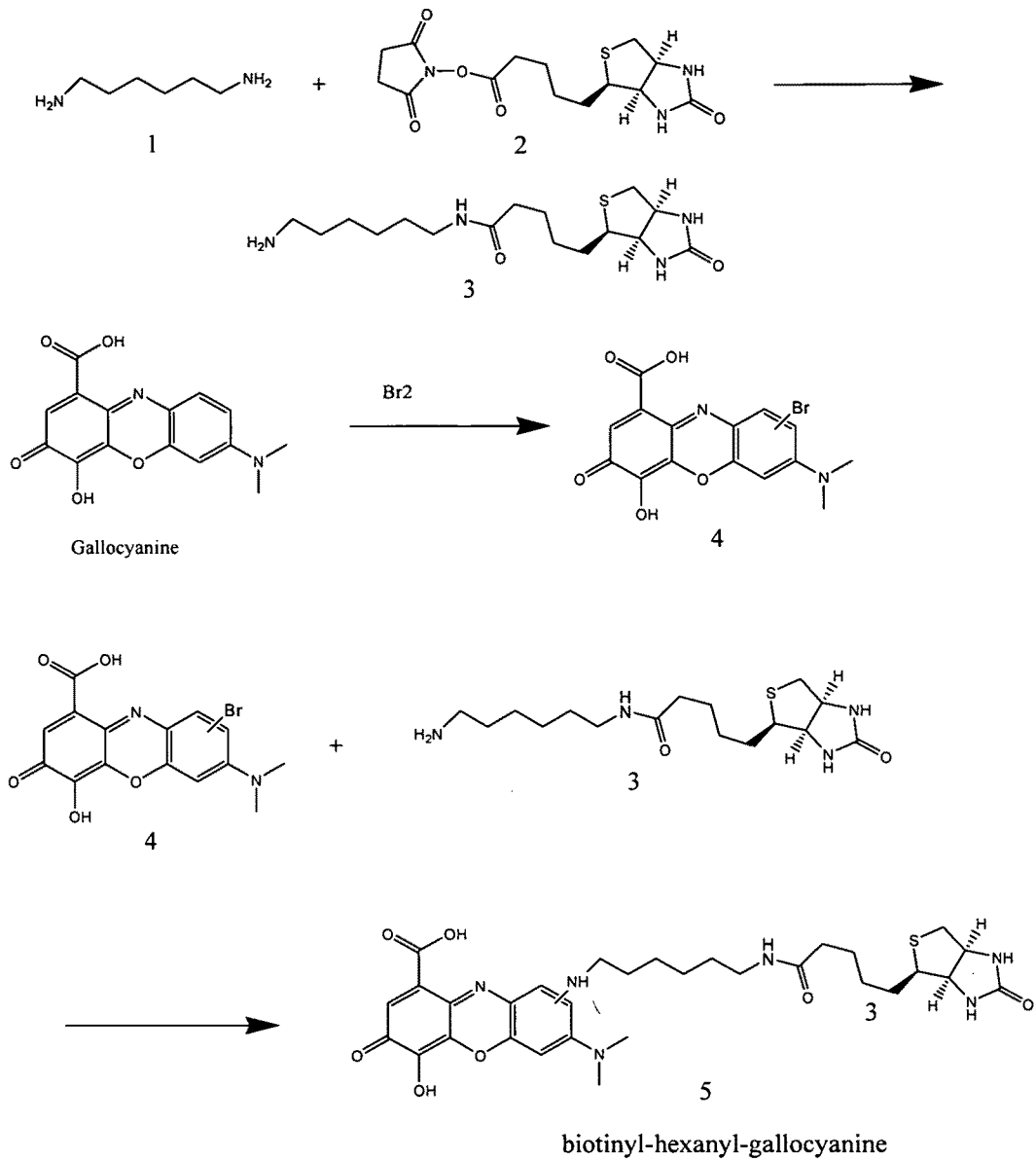
FIG. 44. Synthesis of biotinylated gallocyanine.
Figure 45:
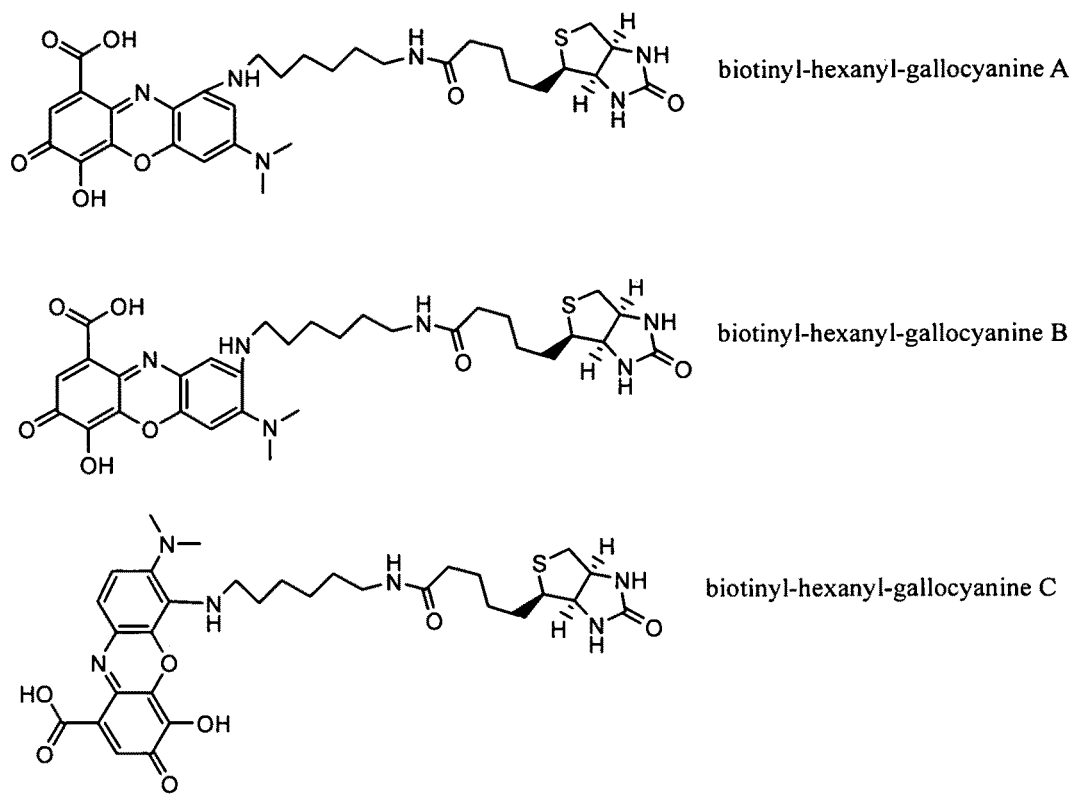
FIG. 45. Structures of various biotinylated gallocyanine products.
Figure 47:
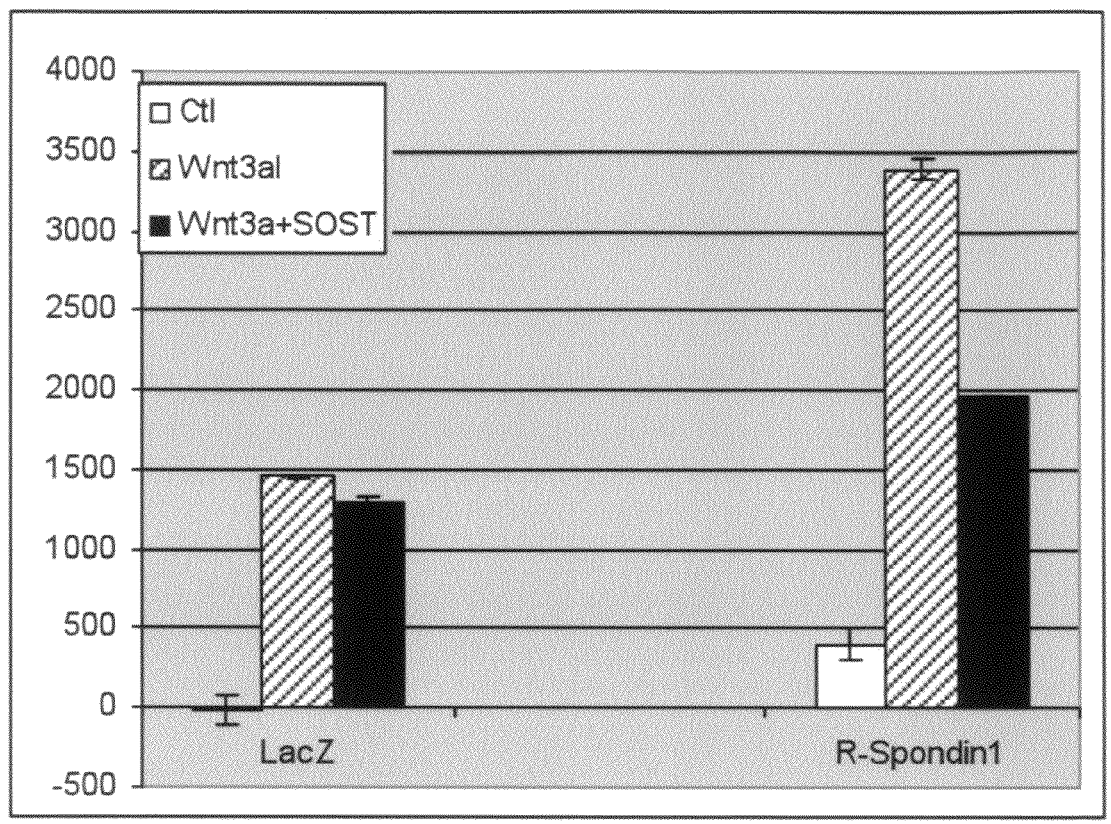
FIG. 47. Assay of Wnt activity and sclerostin suppression in the presence of R-spondin.
Figure 48:
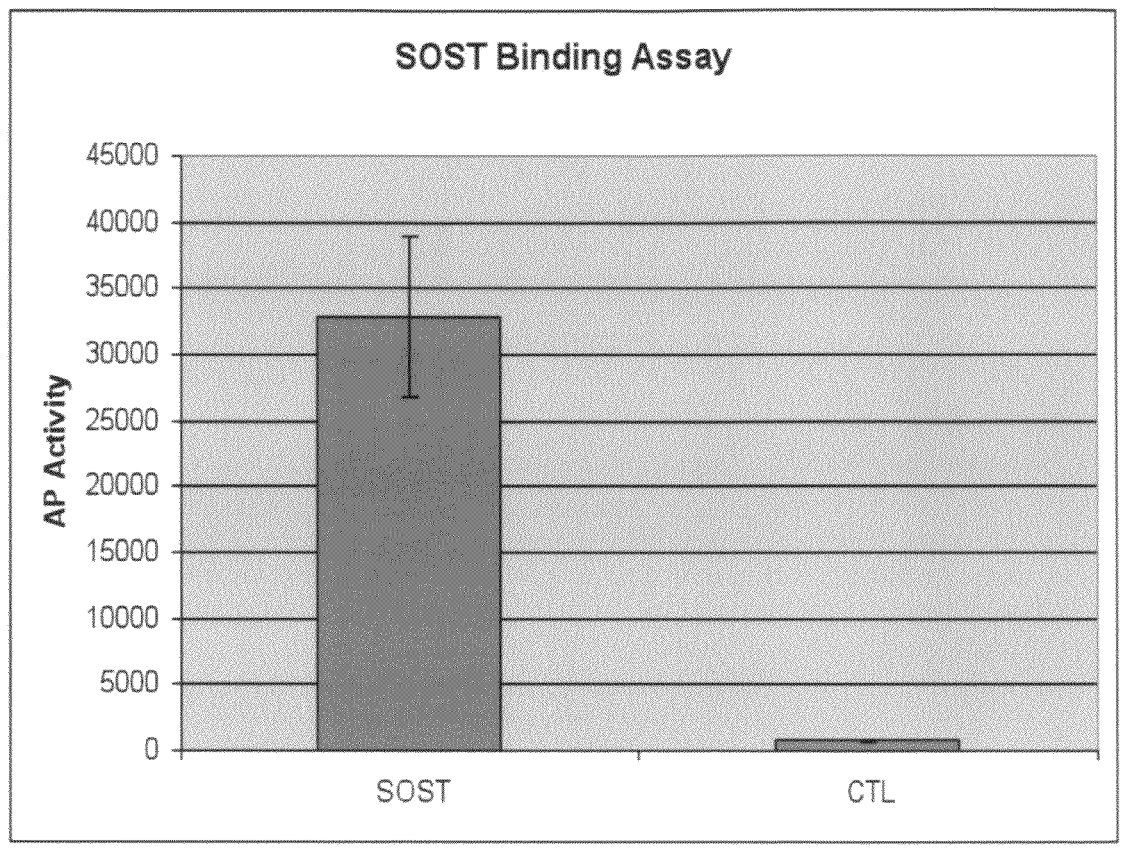
FIG. 48. Sclerostin binding assay.

The various steps of this process are shown in FIG. 44.
Synthesis of Amino-Hexanyl-Biotin, (Compound 3)
4 ml of a solution of Biotin NHS (compound 2, 150 mg, 0.44 mMoles) in DMF was dripped into a 4 ml solution of diaminohexane (compound 1, 134 mg, 1.2 mMoles) in DMF with stirring. After stirring over night, the DMF was removed and the residue was recrystallized from ethanol. A yield of 86 mg of a solid (compound 3) was obtained.
Synthesis of Gallocyanine Bromide (Compound 4)
154 μl, (3 mMoles Bromine) was mixed with 5 ml of pyridine and dropped into a solution of Gallocyanine (0.6 g, 2 mMoles) dissolved in 10 ml of pyridine at room temperature with stirring. The solution was heated to 115° C. and stirred at that temperature overnight. The next day, the solvent was removed in vacuo. The residue was recrystallized from ethanol and 195 mg of solid compound 4 was obtained.
Synthesis of Biotinyl-Hexanyl-Gallocyanine (Compound 5)
A mixture of Gallocyanine Bromide, (compound 4,119 mg, 0.31 mMoles) from Step (i), Copper carbonate (3 mg, 0.0135 mMoles), Potassium acetate (30 mg, 0.3 mMoles) and Amino-Hexanyl-Biotin, (compound 3, 75 mg, 0.21 mMoles) from step (ii) was dissolved in 10 ml of DMF and heated at 80° C. over night.
Purification of Biotinyl-Hexanyl-Gallocyanine, (Compound 5)
The Biotinyl-Hexanyl-Gallocyanine (compound 5) from step (iii) was purified by preparative HPLC where two peaks appeared that were collected with a fraction collector. There are three potential sites on Gallocyanine where Bromination could have taken place during step (ii) and consequently, three different sites where the biotin could be attached (See compounds 5a, 5b and 5c in FIG. 47). It is believed that the presence of the two peaks after HPLC represent the synthesis of two of these products.

EXAMPLE 17

Binding of AlkPhos/LRP to Immobilized Gallocyanine

The biotinylated gallocyanine from Example 16 was tested for the ability to bind to LRP5. 293T cells were transfected with LRP-14, a plasmid expressing a fusion gene comprising the LRP5 extracellular domain (YVVTD repeat domains 1, 2, 3 and 4) fused to alkaline phosphatase resulting in secretion of a soluble form of the fusion protein into the growth medium. 48 hours after transfection, the supernatant of the transfected cells was collected and subsequently referred to as "conditioned medium" (CM). The CM was mixed with or without biotin labeled biotinylated gallocyanine from Example 13 and added to the wells of Reacti-Bind™ NeutrAvidin™ Coated High Binding Capacity (HBC) white 96-well plates (Pierce Biotechnology). After incubating at room temperature for 1 hour, the plate was washed 4 times with PBS/0.5% BSA in with medium. The AP activity in each well was determined using the Tropix Luminescence kit.

Figure 46:
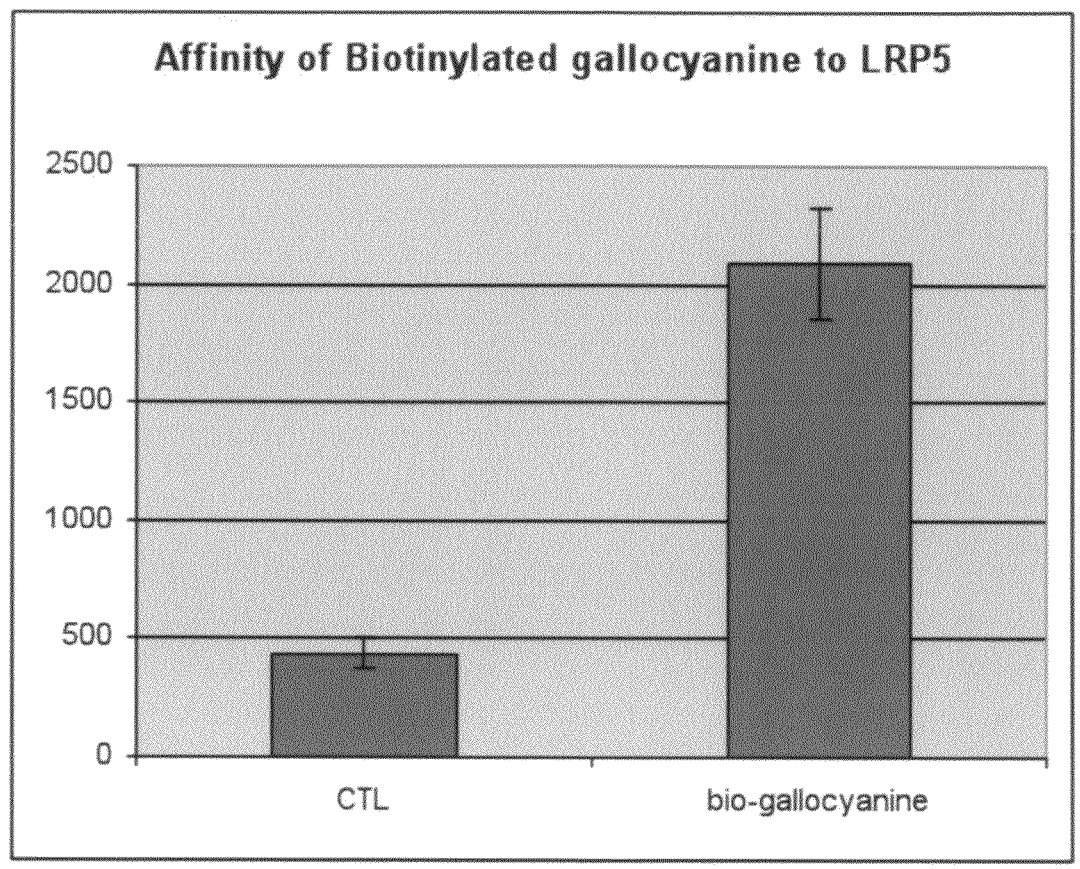
FIG. 46. Binding of AlkPhos-LRP fusion to immobilized biotinylated gallocyanine.

Although all of the biotinylated gallocyanine should be bound to the avidin coated plates, binding of the alkaline phosphatase should only take place through binding of the LRP segment of the fusion protein to the bound gallocyanine. As seen in FIG. 46, a high level of signal from AlkPhos/LRP5 from the conditioned media only takes place when the biotinylated gallocyanine is present on the plate.

EXAMPLE 18

Development of an Assay for Wnt Activity and Sclerostin Inhibition in the Presence of R-Spondin Peak cells were seeded into polylysine coated 24 well plate at $2.5 \times 10^6$ cells/plate. 24 hrs later, the cells in each well were transfected with a mixture of plasmids (0.075 ug of luc, 0.025 ug of lef, 0.05 ug of GFP, and either 0.075 ug of R-Spondin1 or 0.025 ug of lacZ) as described previously in U.S. application Ser. No. 10/849,067. 3 hours after transfection the medium was removed and replaced with 24 hrs after transfection, the medium in each well was replaced with 300 μl of medium with: a) DMEM alone (control medium); b) DMEM+10 μl of Wnt3a conditioned media (prepared as described in the '349 patent application); and c) DMEM+10 μl of Wnt3a conditioned media+1 μl of 100 ng/μl Sclerostin (R&D systems, Minneapolis, Minn.). 6 hrs later, cells were lysed and the luminescence assay was carried out as above.

The results of this Example are seen in FIG. 51 where low activities are seen in the presence of Wnt and LacZ compared to very high levels of Wnt activity seen in the presence of Wnt and R-Spondin. At the same time, under the conditions used in this Example, Wnt activity is still capable of being suppressed by the presence of Sclerostin (SOST). However, even when the suppression took place, it can be seen that there is a much more distinct difference between Wnt and Wnt/Sclerostin when the R-Spondin is present. Thus both for detecting effects on Wnt activity alone or for testing effects of suppression of Wnt activity, this system can be used to investigate the effects of potential pharmacological agents on the Wnt system.

EXAMPLE 19

Development of an Assay for Testing the Effects of Compounds on Binding of Sclerostin to LRP A) Preparation of LRP-AP Fusion Product
An expression vector coding for a protein with the extracellular domains 1 and 2 of LRP5 fused to alkaline phosphatase (LRP12-AP) was made using standard methods. 293T cells were seeded into 9 cm dishes and the next day they were transfected with 12 μg of LRPR12-AP using Lipofectamine Plus (Invitrogen) according to the manufacturer's instructions. Due to the absence of the LRP transmembrane segment, the fusion construct was secreted into the media. 48 hours after transfection, the supernatant was collected as LRP5R12-AP conditioned media (CM) and concentrated 20 fold using a Centricon device (Millipore) and stored at −80° C.

B) Preparation of Binding Plates 96-well C8 white Polysorp plates (NUNC) were coated with 50 µl of 1 µg/ml Sclerostin (SOST) in PBS or with PBS alone (Control) and left overnight at 4° C. Plates were then blocked by the addition of 300 µl of 3% non-fat milk in PBS for two hours at room temperature.

C) Binding Assay

Binding plates from above were washed 3 times with TBST (10 mM Tris/150 mM NaCl/0.05% Tween). The concentrated LRP5R12-AP CM from step (A) was diluted 20 fold with 3% non-fat milk in PBS and 50 µl was added per well. The plates were shaken at room temperature for one hour and then washed 6 times with TBST. After the last wash, 40 µl of AP substrate, CPSD ready-to-use with Sapphire II™ (Tropix) was added into each well. After shaking for 15 minutes at room temperature, the plates were counted on a 1420 Multilabel Counter (Wallac, Victor). The results of this assay are shown in FIG. 50. A series of compounds of interest may be tested by adding them along with the conditioned media and measuring effects on the amount of the LRPR12-AP that binds to the Sclerostin on the plate.

EXAMPLE 20

Stable Cell Line for Identification of Compounds That Effect the Wnt Pathway

A) Subclones

As a preliminary starting point, individual subclones of the 3T3 cells may be tested by transient transfection to identify subclones that have the highest level of Wnt activity. This will insure adequate expression of LRP5/6 or other factors involved in Wnt signaling.

B) Transfection with Transactivator

In the next step, a plasmid expressing the tTA version of the Tet transactivator may be transfected into a chosen suclone using standard reagents such as lipofectamine (Invitrogen, Carlsbad, Calif.). For isolation of a stable transfectant, the transactivator construct also carries a puromycin resistance gene and as such, selection may be carried out by growing the transfected culture in the presence of 3 µg/ml of puromycin.

C) Testing for Transactivator Activity

Individual puromycin-resistant colonies are expanded and a portion is transfected with a plasmid coding for luciferase under the control of tetracycline response element (TRE) promoter. In the absence of tetracycline or DOX, clones that have constitutive expression of the transactivator should permit high levels of luciferase expression from the transfected DNA. 24 hours after transfection, individual cultures may be tested for luciferase activity using standard assays described previously and the identification of stable transfectants expressing the transactivator may be carried out. The remaining untransfected portion of appropriate clones is then used for subsequent steps.

D) Cotransfection with Luciferase and LEF-1

Cell lines selected from step (C) are cotransfected with: (i) a plasmid coding for LEF-1 under the control of TRE promoter and a Neomycin gene under the control of an LTR; (ii) a Wnt responsive plasmid coding for firefly luciferase under the control of a promoter with multiple LEF/TCF sites; and (iii) a plasmid coding for Renilla luciferase under the control of a CMV promoter. If desired, a transfection control may also include a plasmid for GFP as well. Transfected cells are selected by growth in 1 mg/ml of G418 in cell culture medium that also contains 1 µg/ml DOX. Drug resistant colonies are selected and expanded in G418/DOX medium.

E) Selection of Final Clones

Individual cultures are tested for Wnt responsiveness by seeding $1 \times 10^4$ cells into 96 well plates for 24 hours and treating with DMEM and 10% Wnt-conditioned media in the absence of either G418 or DOX for 6 hours. Cells are then tested using Dual Luciferase Reporter Assay (Promega) which separately measures firefly and Renilla luciferase activity. Clones are then selected on a basis of exhibiting high levels of firefly luciferase activity and little or no Renilla luciferase activity.

The invention claimed is:

1. A method for the treatment of osteoporosis in a mammal, the method comprising administering to the mammal the compound:

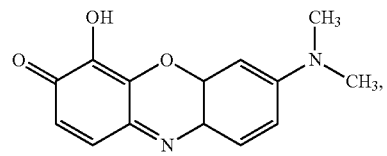 [SMILES: CN(C)C1=CC2OC3=C(O)C(=O)C=CC3=NC2C=C1]

wherein the compound increases Wnt activity in the presence of Dkk1.

* * * * *